United States Patent [19]

Dehesh et al.

[11] Patent Number: 5,850,022
[45] Date of Patent: Dec. 15, 1998

[54] PRODUCTION OF MYRISTATE IN PLANT CELLS

[75] Inventors: Katayoon Dehesh, Vacaville; Toni Voelker, Davis; Deborah Hawkins, Davis, all of Calif.

[73] Assignee: Calgene, Inc., Davis, Calif.

[21] Appl. No.: 460,898

[22] Filed: Jun. 5, 1995

Related U.S. Application Data

[63] Continuation-in-part of Ser. No. 383,756, Feb. 2, 1995, Pat. No. 5,654,495, and Ser. No. 968,971, Oct. 30, 1992, Pat. No. 5,455,167, and a continuation-in-part of Ser. No. 261,695, Jun. 16, 1994, abandoned.

[51] Int. Cl.$^6$ ............................... A01H 5/10; A23D 9/00; C12N 15/52; C12N 15/82
[52] U.S. Cl. ..................... 800/250; 426/607; 435/172.3; 435/320.1; 536/23.2; 536/23.6; 800/255; 800/DIG. 15; 800/205; 800/DIG. 17; 800/DIG. 69
[58] Field of Search .............................. 435/320.1, 240.4, 435/172.3; 536/23.2, 23.6; 800/205, DIG. 17, 250, 255, DIG. 15, DIG. 69; 426/601, 607

[56] References Cited

U.S. PATENT DOCUMENTS

| | | | |
|---|---|---|---|
| 4,410,557 | 10/1983 | Miller | 426/607 |
| 5,455,167 | 10/1995 | Yoelker et al. | 435/172.3 |
| 5,654,495 | 8/1997 | Dehesh et al. | 435/172.3 |

FOREIGN PATENT DOCUMENTS

| | | |
|---|---|---|
| WO 94/10288 | 5/1994 | WIPO . |
| WO 95/06740 | 3/1995 | WIPO . |
| WO 95/13390 | 5/1995 | WIPO . |
| WO 95/27791 | 10/1995 | WIPO . |

OTHER PUBLICATIONS

Slabaugh, et al., "Genetic and Biochemical Studies of Medium Chain Fatty Acid Synthesis in Cuphea", *Plant Lipid Metabolism* (1995) 499–502.

Davies, et al., "Engineering Medium–Chain Fatty Acid Production in Oilseeds", *Seed Oils Future*, (1992) pp. 155–163.

Martini, et al., "Modification of Fatty Acid Composition in the Storage Oil of Transgenic Rapeseed", *Biol. Chem.* (1995) V 376:S5.

Dehesh, et al., "Two Novel Thioesterases Are Key Determinants of the bimodal Distribution of Acyl Chain Length of *Cuphea palustris* Seed Oil", *Plant Physiology*, (1996) vol. 110:203–210.

Yuan, et al., "Modification of the substrate specificity of an acyl–acyl carrier protein thioesterase by protein engineering", *Proc. Natl. Acad. Sci* (1995) vol. 92:10639–10643.

Dehesh, et al., "Unraveling the molecular mechanism determining the fatty acyl composition of *Cuphes palustris* seed oil", *Plant Physiology Supplement*, (1995) vol. 108 No. 2, p. 49 Abstract #183.

Topfer, et al., "Modification of Plant Lipid Synthesis", *Science* (1995) 681–686.

Knau F,V. (1987) Tibtech 5:40–47.

Naggert et al (1987) Biochem J. 243 : 597–601.

Poulose et al. (1985) Journal of Biol. Chem. 260 (29) : 15953–15958.

Gasser, et al. (1989) Science 244 : 1293–1299.

Bayley et al (1989) Tibtech 6 : 1219–1221.

Miyamoto et al (1988) Journal of Biol. Chem. 263 (26) : 13393–13399.

*Primary Examiner*—David T. Fox
*Assistant Examiner*—Amy J. Nelson

[57] ABSTRACT

By this invention, methods to produce C14 fatty acids in plant seed oils are provided. In a first embodiment, this invention relates to particular C14 preferring acyl-ACP thioesterase sequences from *Cuphea palustris*, camphor and nutmeg, and to DNA constructs for the expression of these thioesterases in host cells for production of C14 fatty acids. Other aspects of this invention relate to methods for using other plant medium-chain thioesterases or medium-chain thioesterases from non-plant sources to provide C14 fatty acids in plant cells. In this regard, the production of C14 fatty acids in plant cells as the result of expression from an elm medium chain acyl-ACP thioesterase and a bacterial luxD gene is provided.

14 Claims, 34 Drawing Sheets

```
GCTCTAATAC GACTCACTAT AGGGAAAGCT GGTACGCCTG CAGGTACCGG TCCGGAATTC         60

CCGGGTCGAC CCACGCGTCC GCTGAGTTTG CTGGTTACCA TTTTCCCTGC GAACAAAC         118

ATG GTG GCT GCC GCA GCA AGT GCT GCA TTC TTC TCC GTC GCA ACC CCG         166
Met Val Ala Ala Ala Ala Ser Ala Ala Phe Phe Ser Val Ala Thr Pro
1               5                   10                  15

CGA ACA AAC ATT TCG CCA TCG AGC GTC CCC TTC AAG CCC AAA                 214
Arg Thr Asn Ile Ser Pro Ser Ser Val Pro Phe Lys Pro Lys
        20                  25                  30

TCA AAC CAC AAT GGT GGC TTT CAG GTT AAG GCA AAC GCC AGT GCC CAT         262
Ser Asn His Asn Gly Gly Phe Gln Val Lys Ala Asn Ala Ser Ala His
        35                  40                  45

CCT AAG GCT AAC GGT TCT GCA GTA AGT CTA AAG TCT GGC AGC CTC GAG         310
Pro Lys Ala Asn Gly Ser Ala Val Ser Leu Lys Ser Gly Ser Leu Glu
50                  55                  60

ACT CAG GAG GAC AAA ACT TCA TCG TCG TCC CCT CCT CCT CGG ACT TTC         358
Thr Gln Glu Asp Lys Thr Ser Ser Ser Ser Pro Pro Pro Arg Thr Phe
65                  70                  75                  80
```

FIG. 1A

```
ATT AAC CAG TTG CCC GTC TGG AGT ATG CTT CTG TCT GCA GTC ACG ACT    406
Ile Asn Gln Leu Pro Val Trp Ser Met Leu Leu Ser Ala Val Thr Thr
             85                  90                  95

GTC TTC GGG GTG GCT GAG AAG CAG TGG CCA ATG CTT GAC CGG AAA TCT    454
Val Phe Gly Val Ala Glu Lys Gln Trp Pro Met Leu Asp Arg Lys Ser
            100                 105                 110

AAG AGG CCC GAC ATG CTT GTG GAA CCG CTT GGG GTT GAC AGG ATT GTT    502
Lys Arg Pro Asp Met Leu Val Glu Pro Leu Gly Val Asp Arg Ile Val
            115                 120                 125

TAT GAT GGG GTT AGT TTC AGA CAG AGT TTT TCG ATT AGA TCT TAC GAA    550
Tyr Asp Gly Val Ser Phe Arg Gln Ser Phe Ser Ile Arg Ser Tyr Glu
            130                 135                 140

ATA GGC GCT GAT CGA ACA GCC TCG ATA GAG ACC CTG ATG AAC ATG TTC    598
Ile Gly Ala Asp Arg Thr Ala Ser Ile Glu Thr Leu Met Asn Met Phe
            145                 150                 155                 160

CAG GAA ACA TCT CTT AAT CAT TGT AAG ATT ATC GGT CTT CTC AAT GAC    646
Gln Glu Thr Ser Leu Asn His Cys Lys Ile Ile Gly Leu Leu Asn Asp
            165                 170                 175

GGC TTT GGT CGA ACT CCT GAG ATG TGT AAG AGG GAC CTC ATT TGG GTG    694
Gly Phe Gly Arg Thr Pro Glu Met Cys Lys Arg Asp Leu Ile Trp Val
            180                 185                 190
```

FIG.1B

```
GTC ACG AAA ATG CAG ATC GAG GTG AAT CGC TAT CCT ACT TGG GGT GAT    742
Val Thr Lys Met Gln Ile Glu Val Asn Arg Tyr Pro Thr Trp Gly Asp
    195                 200                 205

ACT ATA GAG GTC AAT ACT TGG GTC TCA GCG TCG GGG AAA CAC GGT ATG    790
Thr Ile Glu Val Asn Thr Trp Val Ser Ala Ser Gly Lys His Gly Met
    210                 215                 220

GGT CGA GAT TGG CTG ATA AGT GAT TGC CAT ACA GGA GAA ATT CTT ATA    838
Gly Arg Asp Trp Leu Ile Ser Asp Cys His Thr Gly Glu Ile Leu Ile
225                 230                 235                 240

AGA GCA ACG AGC GTG TGG GCT ATG ATG AAT CAA AAG ACG AGA AGA TTG    886
Arg Ala Thr Ser Val Trp Ala Met Met Asn Gln Lys Thr Arg Arg Leu
                245                 250                 255

TCG AAA ATT CCA TAT GAG GTT CGA CAG GAG ATA GAG CCT CAG TTT GTG    934
Ser Lys Ile Pro Tyr Glu Val Arg Gln Glu Ile Glu Pro Gln Phe Val
            260                 265                 270

GAC TCT GCT CCT GTC ATT GTA GAC GAT CGA AAA TTT CAC AAG CTT GAT    982
Asp Ser Ala Pro Val Ile Val Asp Asp Arg Lys Phe His Lys Leu Asp
        275                 280                 285
```

FIG.1C

```
TTG AAG ACC GGT GAT TCC ATT TGC AAT GGT CTA ACT CCA AGG TGG ACT    1030
Leu Lys Thr Gly Asp Ser Ile Cys Asn Gly Leu Thr Pro Arg Trp Thr
        290             295             300

GAC TTG GAT GTC AAT CAG CAC GTT AAC AAT GTG AAA TAC ATC GGG TGG    1078
Asp Leu Asp Val Asn Gln His Val Asn Asn Val Lys Tyr Ile Gly Trp
305             310             315             320

ATT CTC CAG AGT GTT CCC ACA GAA GTT TTC GAG ACG CAG GAG CTA TGT    1126
Ile Leu Gln Ser Val Pro Thr Glu Val Phe Glu Thr Gln Glu Leu Cys
        325             330             335

GGC CTC ACC CTT GAG TAT AGG CGA GAA TGC GGA AGG GAC AGT GTG CTG    1174
Gly Leu Thr Leu Glu Tyr Arg Arg Glu Cys Gly Arg Asp Ser Val Leu
340             345             350

GAG TCC GTG ACC ATG GAT CCA TCA AAA GAG GGA GAC CGG TCT CTT        1222
Glu Ser Val Thr Met Asp Pro Ser Lys Glu Gly Asp Arg Ser Leu
        355             360             365

TAC CAG CAC CTT CTC CGA CTC GAG GAC GGG GCT GAT ATC GTC AAG GGG    1270
Tyr Gln His Leu Leu Arg Leu Glu Asp Gly Ala Asp Ile Val Lys Gly
370             375             380
```

FIG.1D

```
AGA ACC GAG TGG CGG CCG AAG AAT GCA GGA GCC AAG GGA GCA ATA TTA    1318
Arg Thr Glu Trp Arg Pro Lys Asn Ala Gly Ala Lys Gly Ala Ile Leu
385                     390                 395                 400

ACC GGA AAG ACC TCA AAT GGA AAC TCT ATA TCT TAGAAGGAGG AAGGGACCTT  1371
Thr Gly Lys Thr Ser Asn Gly Asn Ser Ile Ser
        405                 410

TCCGAGTTGT GTGTTTATTT GCTTTGCTTT GATTCACTCC ATTGTATAAT AATACTACGG  1431

TCAGCCGTCT TTGTATTTGC TAAGACAAAT AGCACAGTCA TTAAGTTAAA AAAAAAAAAA  1491

AAGGGCGGCC GCTCTAGAGG ATCCAAGCTT ACGTACGCGT GCATGCCGACG TCATAGCTCT  1551

TCTATAGTGT CACCTAAATT CAATTCACTG                                   1581
```

FIG. 1E

```
CCG GAT TGG AGC ATG CTT CTT GCA GCA ATC ACA ACC ATC TTC TTG GCA    48
Pro Asp Trp Ser Met Leu Leu Ala Ala Ile Thr Thr Ile Phe Leu Ala
 1               5                  10                  15

GCC GAG AAG CAG TGG ACG AAT CTT GAC TGG ACG AAG CCC AGG AGG CCT GAC    96
Ala Glu Lys Gln Trp Thr Asn Leu Asp Trp Thr Lys Pro Arg Arg Pro Asp
            20                  25                  30

ATG CTC GTC GAC TTT GAC CCT TTT AGT CTG GGG AGG TTC GTT CAG GAT   144
Met Leu Val Asp Phe Asp Pro Phe Ser Leu Gly Arg Phe Val Gln Asp
        35                  40                  45

GGG TTG ATT TTC AGG CAG AAT TTC TCC ATC AGG TCT TAT GAG ATT GGC   192
Gly Leu Ile Phe Arg Gln Asn Phe Ser Ile Arg Ser Tyr Glu Ile Gly
    50                  55                  60

GCG GAT CGG ACG GCA TCC ATA GAG ACG TTA ATG AAT CAT CTA CAG GAA   240
Ala Asp Arg Thr Ala Ser Ile Glu Thr Leu Met Asn His Leu Gln Glu
65                  70                  75                  80

ACG GCC CTA AAC CAT GTA AGG TGT ATA GGG CTC CTC GAT GAT GGT TTT   288
Thr Ala Leu Asn His Val Arg Cys Ile Gly Leu Leu Asp Asp Gly Phe
                85                  90                  95
```

FIG.2A

| GGT | TCG | ACG | CCT | GAG | ATG | ACT | AGG | AGA | GAT | CTG | ATA | TGG | GTG | GTT | ACA | 336 |
| Gly | Ser | Thr | Pro | Glu | Met | Thr | Arg | Arg | Asp | Leu | Ile | Trp | Val | Val | Thr | |
| | | | 100 | | | | | 105 | | | | | 110 | | | |

| AGG | ATG | CAG | GTT | CTG | GTG | GAT | CGC | TAT | CCT | TCC | TGG | GGG | GAT | GTC | ATT | 384 |
| Arg | Met | Gln | Val | Leu | Val | Asp | Arg | Tyr | Pro | Ser | Trp | Gly | Asp | Val | Ile | |
| | | 115 | | | | | 120 | | | | | 125 | | | | |

| GAA | GTA | GAC | TCC | TGG | GTT | ACT | CCA | TCT | GGA | AAG | AAT | GGG | ATG | AAA | CGT | 432 |
| Glu | Val | Asp | Ser | Trp | Val | Thr | Pro | Ser | Gly | Lys | Asn | Gly | Met | Lys | Arg | |
| | 130 | | | | | 135 | | | | | 140 | | | | | |

| GAA | TGG | TTT | CTC | CGT | GAT | TGC | AAG | ACA | GGC | GAA | ATC | CTG | ACA | CGA | GCT | 480 |
| Glu | Trp | Phe | Leu | Arg | Asp | Cys | Lys | Thr | Gly | Glu | Ile | Leu | Thr | Arg | Ala | |
| 145 | | | | | 150 | | | | | 155 | | | | | 160 | |

| ACC | AGT | GTT | TGG | GTG | ATG | ATG | AAT | AAA | CGG | ACA | CGG | AGG | TTG | TCC | AAA | 528 |
| Thr | Ser | Val | Trp | Val | Met | Met | Asn | Lys | Arg | Thr | Arg | Arg | Leu | Ser | Lys | |
| | | | 165 | | | | | 170 | | | | | 175 | | | |

| ATC | CCT | GAA | GAA | GTT | AGA | GTC | GAA | ATA | GAG | CCT | TAT | TTT | GTG | GAG | CAT | 576 |
| Ile | Pro | Glu | Glu | Val | Arg | Val | Glu | Ile | Glu | Pro | Tyr | Phe | Val | Glu | His | |
| | | 180 | | | | | 185 | | | | | 190 | | | | |

FIG.2B

```
GGA GTC TTG GAT GAG GAC AGC AGA AAA CTA CCA AAG CTC AAT GAC AAC    624
Gly Val Leu Asp Glu Asp Ser Arg Lys Leu Pro Lys Leu Asn Asp Asn
            195                 200                 205

ACT GCA AAT TAC ATC AGA AGA GGC CTA GCT CCT CGG TGG AGT GAT TTA    672
Thr Ala Asn Tyr Ile Arg Arg Gly Leu Ala Pro Arg Trp Ser Asp Leu
        210                 215                 220

GAT GTC AAT CAG CAT GTG AAC AAT GTC AAA TAC ATT GGC TGG ATT CTT    720
Asp Val Asn Gln His Val Asn Asn Val Lys Tyr Ile Gly Trp Ile Leu
    225                 230                 235                 240

GAG AGC GTG CCA TCT TCA CTG TTG GAG AGT CAT GAG AGT GGT TTG CAA TCC    768
Glu Ser Val Pro Ser Ser Leu Leu Glu Ser His Glu Ser Gly Leu Gln Ser
                245                 250                 255

ACA CTT GAG TAT AGG AAG GAG TGT GGA AAG GAC GGT TTG CTG CAA TCC    816
Thr Leu Glu Tyr Arg Lys Glu Cys Gly Lys Asp Gly Leu Leu Gln Ser
        260                 265                 270

CTG ACT GCT GTT GCC AGT GAT TAT GGG GGT GGA TCC CTT GAA GCT GGC    864
Leu Thr Ala Val Ala Ser Asp Tyr Gly Gly Gly Ser Leu Glu Ala Gly
    275                 280                 285
```

FIG.2C

```
GTT GAG TGT GAC CAC CTT CTT CGC CTT GAA GAT GGG AGT GAG ATT ATG   912
Val Glu Cys Asp His Leu Leu Arg Leu Glu Asp Gly Ser Glu Ile Met
290                     295                 300

AGG GGA AAG ACG GAA TGG AGG CCC AAG CGT GCC GCC AAC ACT ACC TAC   960
Arg Gly Lys Thr Glu Trp Arg Pro Lys Arg Ala Ala Asn Thr Thr Tyr
305                     310                 315                 320

TTT GGA AGC GTT GAT GAT ATT CCT CCC CAC CCA ATA TAT ATA TAT ATA  1008
Phe Gly Ser Val Asp Asp Ile Pro Pro His Pro Ile Tyr Ile Tyr Ile
            325                 330                 335

TAT ATA TAT ATA TAT ATA TAT TGG GTG GGG AGC AGC TGC AGC         1056
Tyr Ile Tyr Ile Tyr Ile Tyr Trp Val Gly Ser Ser Cys Ser
        340                 345                 350

GGC AGC ACG ACA ATG TCG AGG ACA CGA TGACGATCAG TATGTTTCGT       1106
Gly Ser Ser Thr Thr Met Ser Arg Thr Arg
355                     360

GCGGTATTTA GCAATTCCGT ATGTAGAAATC CTGCGTGTAC TGGCAGATAA TTTTTTGATT 1166

TGTTCTTTTC GTTTACGAGG GGAACCCGTG TAATTAGTTC AACTGTATT TCTGTTTCTT 1226
```

FIG.2D

```
CCTTAAGTGT TTCAACACCC CTCTCTCTCT CGCGGCGGCG CGTGCGGCTCA CATTTTCCAT 1286

TCCTTTTCTT TTTATTCTAG TTGTACGAGT GGGAGTTCAT TTGCACTAAA TTGTTGAAAA 1346

ATCTCGTTGC TTGG                                                  1360
```

FIG.2E

```
GGAGAGCCGC CTCTTCAGCC CACCACCACC TCTAAAACAA CAGGCCCAAA ACTCCCTCCT     60

TTCTCTGTCC CTTTCCGGTG CTTCCCCCTC TATTTTAGAC CTCCTCCTTT ATATTTCCCA    120

ACGTAGAATA ATACCAAAAC CCTAAACCGA GAAGAAGATA AAAGAAAGAG GAGAGAGAAA    180

CAGAAAGAGA TAGAGAGAGA AAAAAAAATCG GTCTTCTCTC TCTTTCTCTG TCGCTGCGAA    240

GGAGCGGCCG TGAAATTTGG TCATTTGCTA TGAGAAATAT TCCTTCTGTG ATGCTTGATT    300

TCTAATTTAA CGAGTCTGTA TCGTAATTTT CTCATC ATG GTT GCC ACA TCT GCT     354
                                     Met Val Ala Thr Ser Ala
                                      1                   5

GCC TCC GCT TTC TTC CCG GTT GCC TCT CCG TCT CCA GTG AAG CCT TCG     402
Ala Ser Ala Phe Phe Pro Val Ala Ser Pro Ser Pro Val Lys Pro Ser
            10                  15                  20

ATG ATG CTC GGT GGT GGA GGT GGT GGG TCG GAT AAT CTC GAC GCC CGT GGG  450
Met Met Leu Gly Gly Gly Gly Gly Gly Ser Asp Asn Leu Asp Ala Arg Gly
         25                  30                  35

ATC AAA TCC CGC CCT GCC TCC TCT GGT GGC CTT CAA GTA AAG GCC AAT     498
Ile Lys Ser Arg Pro Ala Ser Ser Gly Gly Leu Gln Val Lys Ala Asn
         40                  45                  50
```

FIG.3A

```
GCT CAT ACT GTT CCC AAG ATC AAT GGT AAC AAG GCG GGC CTT TTG ACG        546
Ala His Thr Val Pro Lys Ile Asn Gly Asn Lys Ala Gly Leu Leu Thr
 55                  60                  65                  70

CCT ATG GAG AGC ACT AAG GAC GAG ATC GTG GCT GCC CCA ACG GTT            594
Pro Met Glu Ser Thr Lys Asp Glu Ile Val Ala Ala Pro Thr Val
             75                  80                  85

GCT CCT AAG AGG ACT TTC ATC AAC CAG CTG CCG GAT TGG AGC ATG CTT        642
Ala Pro Lys Arg Thr Phe Ile Asn Gln Leu Pro Asp Trp Ser Met Leu
             90                  95                 100

CTT GCA GCA ATC ACA ACC ATC TTC TTG GCA GCC GAG AAG CAG TGG ACG        690
Leu Ala Ala Ile Thr Thr Ile Phe Leu Ala Ala Glu Lys Gln Trp Thr
            105                 110                 115

AAT CTT GAC TGG AAG CCC AGG AGG CCT GAC ATG CTC GTC GAC TTT GAC        738
Asn Leu Asp Trp Lys Pro Arg Arg Pro Asp Met Leu Val Asp Phe Asp
            120                 125                 130

CCT TTT AGT CTG GGG AGG TTC GTT CAG GAT GGG TTG ATT TTC AGG CAG        786
Pro Phe Ser Leu Gly Arg Phe Val Gln Asp Gly Leu Ile Phe Arg Gln
            135                 140                 145         150

AAT TTC TCC ATC AGG TCT TAT GAG ATT GGC GCG GAT CGG ACG GCA TCC        834
Asn Phe Ser Ile Arg Ser Tyr Glu Ile Gly Ala Asp Arg Thr Ala Ser
            155                 160                 165
```

FIG.3B

```
ATA GAG ACG TTA ATG AAT CAT CTA CAG GAA ACG GCC CTA AAC CAT GTA    882
Ile Glu Thr Leu Met Asn His Leu Gln Glu Thr Ala Leu Asn His Val
170                     175                     180

AGG TGT ATA GGG CTC CTC GAT GAT GGT TTT GGT TCG ACG CCT GAG ATG    930
Arg Cys Ile Gly Leu Leu Asp Asp Gly Phe Gly Ser Thr Pro Glu Met
        185                     190                     195

ACT AGG AGA GAT CTG ATA TGG GTG GTT ACA AGG ATG CAG GTT CTG GTG    978
Thr Arg Arg Asp Leu Ile Trp Val Val Thr Arg Met Gln Val Leu Val
200                     205                     210

GAT CGC TAT CCT TCC TGG GGG GAT GTC ATT GAA GTA GAC TCC TGG GTT   1026
Asp Arg Tyr Pro Ser Trp Gly Asp Val Ile Glu Val Asp Ser Trp Val
215                     220                     225                230

ACT CCA TCT GGA AAG AAT GGG ATG AAA CGT GAA TGG TTT CTC CGT GAT   1074
Thr Pro Ser Gly Lys Asn Gly Met Lys Arg Glu Trp Phe Leu Arg Asp
        235                     240                     245

TGC AAG ACA GGC GAA ATC CTG ACA CGA GCT ACC AGT GTT TGG GTG ATG   1122
Cys Lys Thr Gly Glu Ile Leu Thr Arg Ala Thr Ser Val Trp Val Met
250                     255                     260

ATG AAT AAA CGG ACA CGG AGG TTG TCC AAA ATC CCT GAA GAA GTT AGA   1170
Met Asn Lys Arg Thr Arg Arg Leu Ser Lys Ile Pro Glu Glu Val Arg
265                     270                     275
```

FIG.3C

```
GTC GAA ATA GAG CCT TAT TTT GTG GAG CAT GGA GTC TTG GAT GAG GAC     1218
Val Glu Ile Glu Pro Tyr Phe Val Glu His Gly Val Leu Asp Glu Asp
    280                 285                 290

AGC AGA AAA CTA CCA AAG CTC AAT GAC AAC ACT GCA AAT TAC ATC AGA     1266
Ser Arg Lys Leu Pro Lys Leu Asn Asp Asn Thr Ala Asn Tyr Ile Arg
295                 300                 305                 310

AGA GGC CTA GCT CCT CGG TGG AGT GAT TTA GAT GTC AAT CAG CAT GTG     1314
Arg Gly Leu Ala Pro Arg Trp Ser Asp Leu Asp Val Asn Gln His Val
        315                 320                 325

AAC AAT GTC AAA TAC ATT GGC TGG ATT CTT GAG AGC GTG CCA TCT TCA     1362
Asn Asn Val Lys Tyr Ile Gly Trp Ile Leu Glu Ser Val Pro Ser Ser
330                 335                 340

CTG TTG GAG AGT CAT GAG CTG TAT GGG ATG ACA CTT GAG TAT AGG AAG     1410
Leu Leu Glu Ser His Glu Leu Tyr Gly Met Thr Leu Glu Tyr Arg Lys
    345                 350                 355

GAG TGT GGA AAG GAC GGT TTG CAA TCC CTG ACT GCT GTT GCC AGT         1458
Glu Cys Gly Lys Asp Gly Leu Gln Ser Leu Thr Ala Val Ala Ser
360                 365                 370

GAT TAT GGG GGT GGA TCC CTT GAA GCT GGC GTT GAG TGT GAC CAC CTT     1506
Asp Tyr Gly Gly Gly Ser Leu Glu Ala Gly Val Glu Cys Asp His Leu
    375                 380                 385                 390
```

FIG.3D

```
CTT CGC CTT GAA GAT GGG AGT GAG ATT ATG AGG GGA AAG ACG GAA TGG   1554
Leu Arg Leu Glu Asp Gly Ser Glu Ile Met Arg Gly Lys Thr Glu Trp
                 395                     400                 405

AGG CCC AAG CGT GCC GCC AAC ACT ACC TAC TTT GGA AGC GTT GAT GAT   1602
Arg Pro Lys Arg Ala Ala Asn Thr Thr Tyr Phe Gly Ser Val Asp Asp
             410                     415                 420

ATT CCT CCA GCA AAT AAT GCA TAGCCAAAAT GTATATATAT ATATATATAT      1653
Ile Pro Pro Ala Asn Asn Ala
         425

ATATATATAT ATATATATAT ATTGGGTGGG GAGCAGCTGC AGCGGCAGCA            1713

GCACGACAAT GTCGAGGACA CGATGACGAT CAGTATGTTT CGTGCGGTAT TTAGCAATTC 1773

CGTATGTAGA ATCCTGCGTG TACTGGCAGA TAATTTTTTG ATTTGTTCTT TTCGTTTACG 1833

AGGGGAACCC GTGTAATTAG TTCAACTGTA TTTTCTGTTT CTTCCTTAAG TGTTTCAACA 1893

CCCCTCTCTC TCTCGCGCGC GCGCGTGCGC TCACATTTC CATTCCTTTT CTTTTTATTC  1953

TAGTTGTACG AGTGGGAGTT CATTTGCACT                                  1983
```

FIG.3E

```
T CTA GAG TGG AAG CCG AAG CCA AAT CCA CCC CAG TTG CTT GAT GAC CAT    49
  Leu Glu Trp Lys Pro Lys Pro Asn Pro Pro Gln Leu Leu Asp Asp His
  1                   5                       10                  15

TTT GGG CCG CAT GGG TTA GTT TTC AGG CGC ACC TTT GCC ATC AGA TCG      97
Phe Gly Pro His Gly Leu Val Phe Arg Arg Thr Phe Ala Ile Arg Ser
                20                      25                      30

TAT GAG GTG GGA CCT GAC CGC TCC ACA TCT ATA GTG GCT GTT ATG AAT     145
Tyr Glu Val Gly Pro Asp Arg Ser Thr Ser Ile Val Ala Val Met Asn
            35                      40                      45

CAC TTG CAG GAG GCT GCA CTT AAT CAT GCG AAG AGT GTG GGA ATT CTA     193
His Leu Gln Glu Ala Ala Leu Asn His Ala Lys Ser Val Gly Ile Leu
        50                      55                      60

GGA GAT GGA TTC GGT ACG ACG CTA GAG ATG AGT AAG AGA GAT CTG ATA     241
Gly Asp Gly Phe Gly Thr Thr Leu Glu Met Ser Lys Arg Asp Leu Ile
65                      70                      75                  80

TGG GTT GTG AAA CGC ACG CAT GTT GCT GTG GAA CGG TAC CCT GCT TGG     289
Trp Val Val Lys Arg Thr His Val Ala Val Glu Arg Tyr Pro Ala Trp
                85                      90                      95

GGT GAT ACT GTT GAA GTA GAG TGC TGG GTT GGT GCA TCG GGA AAT AAT     337
Gly Asp Thr Val Glu Val Glu Cys Trp Val Gly Ala Ser Gly Asn Asn
                100                     105                     110
```

FIG.4A

```
GGC AGG CGC CAT GAT TTC CTT GTC CGG GAC TGC AAA ACA GGC GAA ATT    385
Gly Arg Arg His Asp Phe Leu Val Arg Asp Cys Lys Thr Gly Glu Ile
        115                 120                 125

CTT ACA AGA TGT ACC AGT CTT TCG GTG ATG ATG AAT ACA AGG ACA AGG    433
Leu Thr Arg Cys Thr Ser Leu Ser Val Met Met Asn Thr Arg Thr Arg
        130                 135                 140

AGG TTG TCC AAA ATC CCT GAA GAA GTT AGA GGG GAG ATA GGG CCT GCA    481
Arg Leu Ser Lys Ile Pro Glu Glu Val Arg Gly Glu Ile Gly Pro Ala
        145                 150                 155                 160

TTC ATT GAT AAT GTG GCT GTC AAA GAC GAG GAA ATT AAG AAA CCA CAG    529
Phe Ile Asp Asn Val Ala Val Lys Asp Glu Glu Ile Lys Lys Pro Gln
        165                 170                 175

AAG CTC AAT GAC AGC ACT GCA GAT TAC ATC CAA GGA GGA TTG ACT CCT    577
Lys Leu Asn Asp Ser Thr Ala Asp Tyr Ile Gln Gly Gly Leu Thr Pro
        180                 185                 190

CGA TGG AAT GAT TTG GAT ATC AAT CAG CAC GTT AAC AAC ATC AAA TAC    625
Arg Trp Asn Asp Leu Asp Ile Asn Gln His Val Asn Asn Ile Lys Tyr
        195                 200                 205

GTT GAC TGG ATT CTT GAG ACT GTC CCA GAC TCA ATC TTT GAG AGT CAT    673
Val Asp Trp Ile Leu Glu Thr Val Pro Asp Ser Ile Phe Glu Ser His
        210                 215                 220
```

FIG.4B

```
CAT ATT TCC AGC TTC ACT ATT GAA TAC AGG AGA GAG TGC ACG AGG GAT    721
His Ile Ser Ser Phe Thr Ile Glu Tyr Arg Arg Glu Cys Thr Arg Asp
225                 230                 235                 240

AGC GTG CTG CAG TCC CTG ACC ACT GTC TCC GGT GGC TCG TCG GAA GCT    769
Ser Val Leu Gln Ser Leu Thr Thr Val Ser Gly Gly Ser Ser Glu Ala
        245                 250                 255

GGG TTA GTG TGC GAG CAC TTG CTC CAG CTT GAA GGT GGG TCT GAG GTA    817
Gly Leu Val Cys Glu His Leu Leu Gln Leu Glu Gly Gly Ser Glu Val
            260                 265                 270

TTG AGG GCA AAA ACA GAG TGG AGG CCT AAG CTT ACC GAT AGT TTC AGA    865
Leu Arg Ala Lys Thr Glu Trp Arg Pro Lys Leu Thr Asp Ser Phe Arg
                275                 280                 285

GGG ATT AGT GTG ATA CCC GCA GAA TCG AGT GTC TAACTAACGA AGAAGCATC   918
Gly Ile Ser Val Ile Pro Ala Glu Ser Ser Val
                    290                 295

TGATGAAGTT TCTCCCTGTGC TGTTGTTCGT GAGGATGCTT TTTAGAAGCT GCAGTTTGCA   978

TTGCTTGTGC AGAATCATGG CCTGTGGTTT TAGATATATA TTCAAAATTG TCCTATAGTC  1038

AAGAAACTTA ATATCAGAAA AATAACTCAA TGAGTCAAGG TTATCGAAGT AGTCATGTAA  1098

GCTTTGAAAT ATGTTGTGTA TTCCTCGGCT TTATGTAATC TGTAAGCTCT TTCTCTTGC   1157
```

FIG.4C

| | | | | | | | | | | | | | | | |
|---|---|---|---|---|---|---|---|---|---|---|---|---|---|---|---|
| GAA | TTC | GGC | ACG | AGG | GGC | TCC | GGT | GCT | TTG | CAG | GTG | AAG | GCA | AGT | TCC | 48 |
| Glu | Phe | Gly | Thr | Arg | Gly | Ser | Gly | Ala | Leu | Gln | Val | Lys | Ala | Ser | Ser | |
| | | | 5 | | | | | | 10 | | | | | 15 | | |
| CAA | GCT | CCA | CCA | AAG | CTC | AAT | GGT | TCC | AAT | GTG | GGT | TTG | GTT | AAA | TCT | 96 |
| Gln | Ala | Pro | Pro | Lys | Leu | Asn | Gly | Ser | Asn | Val | Gly | Leu | Val | Lys | Ser | |
| | | 20 | | | | | 25 | | | | | | 30 | | | |
| AGC | CAA | ATT | GTG | AAG | AAG | GGT | GAT | GAC | ACC | ACA | TCT | CCT | GCA | AGA | | 144 |
| Ser | Gln | Ile | Val | Lys | Lys | Gly | Asp | Asp | Thr | Thr | Ser | Pro | Ala | Arg | | |
| | 35 | | | | | 40 | | | | | 45 | | | | | |
| ACT | TTC | ATC | AAC | CAA | TTG | CCT | GAT | TGG | AGC | ATG | CTT | CTT | GCT | GCT | ATC | 192 |
| Thr | Phe | Ile | Asn | Gln | Leu | Pro | Asp | Trp | Ser | Met | Leu | Leu | Ala | Ala | Ile | |
| 50 | | | | | 55 | | | | | 60 | | | | | | |
| ACA | ACC | CTG | TTC | TTG | GCT | GCA | GAG | AAG | CAG | TGG | ATG | CTT | GAT | TGG | | 240 |
| Thr | Thr | Leu | Phe | Leu | Ala | Ala | Glu | Lys | Gln | Trp | Met | Leu | Asp | Trp | | |
| 65 | | | | 70 | | | | | 75 | | | | | 80 | | |
| AAA | CCC | AAA | AGG | CCT | GAC | ATG | CTT | GTT | GAT | CCA | TTT | GGT | CTT | GGA | AGG | 288 |
| Lys | Pro | Lys | Arg | Pro | Asp | Met | Leu | Val | Asp | Pro | Phe | Gly | Leu | Gly | Arg | |
| | | 85 | | | | | 90 | | | | | 95 | | | | |
| TTT | GTT | CAG | GAT | GGT | CTT | GTT | TTC | CGC | AAC | AAC | TTT | TCA | ATT | CGA | TCA | 336 |
| Phe | Val | Gln | Asp | Gly | Leu | Val | Phe | Arg | Asn | Asn | Phe | Ser | Ile | Arg | Ser | |
| | | 100 | | | | | 105 | | | | | 110 | | | | |

FIG. 5A

| | | | | | | | | | | | | | | | | |
|---|---|---|---|---|---|---|---|---|---|---|---|---|---|---|---|---|
| TAT | GAA | ATA | GGG | GCT | GAT | CGA | ACG | GCT | TCT | ATA | GAA | ACG | TTA | ATG | AAT | 384 |
| Tyr | Glu | Ile | Gly | Ala | Asp | Arg | Thr | Ala | Ser | Ile | Glu | Thr | Leu | Met | Asn | |
| | | 115 | | | | | 120 | | | | | 125 | | | | |
| CAT | CTG | CAG | GAA | ACA | GCT | CTT | AAT | CAT | GTG | AAG | TCT | GTT | GGG | CTT | CTT | 432 |
| His | Leu | Gln | Glu | Thr | Ala | Leu | Asn | His | Val | Lys | Ser | Val | Gly | Leu | Leu | |
| 130 | | | | | 135 | | | | | 140 | | | | | | |
| GAG | GAT | GGC | CTA | GGT | TCG | ACT | CGA | GAG | ATG | TCC | TTG | AGG | AAC | CTG | ATA | 480 |
| Glu | Asp | Gly | Leu | Gly | Ser | Thr | Arg | Glu | Met | Ser | Leu | Arg | Asn | Leu | Ile | |
| 145 | | | | 150 | | | | | 155 | | | | | 160 | | |
| TGG | GTT | GTC | ACT | AAA | ATG | CAG | GTT | GCG | GTT | GAT | CGC | TAT | CCA | ACT | TGG | 528 |
| Trp | Val | Val | Thr | Lys | Met | Gln | Val | Ala | Val | Asp | Arg | Tyr | Pro | Thr | Trp | |
| | 165 | | | | | 170 | | | | | 175 | | | | | |
| GGA | GAT | GAA | GTT | CAG | GTA | TCC | TCT | TGG | GCT | ACT | GCA | ATT | GGA | AAG | AAT | 576 |
| Gly | Asp | Glu | Val | Gln | Val | Ser | Ser | Trp | Ala | Thr | Ala | Ile | Gly | Lys | Asn | |
| | | 180 | | | | | 185 | | | | | 190 | | | | |
| GGA | ATG | CGT | GAA | TGG | ATA | GTC | ACT | GAT | TTT | AGA | ACT | GGT | GAA | ACT | | 624 |
| Gly | Met | Arg | Glu | Trp | Ile | Val | Thr | Asp | Phe | Arg | Thr | Gly | Glu | Thr | | |
| | 195 | | | | | 200 | | | | | 205 | | | | | |
| CTA | TTA | AGA | GCC | ACC | AGT | GTT | TGG | GTG | ATG | ATG | AAT | AAA | CTG | ACG | AGG | 672 |
| Leu | Leu | Arg | Ala | Thr | Ser | Val | Trp | Val | Met | Met | Asn | Lys | Leu | Thr | Arg | |
| 210 | | | | | 215 | | | | | 220 | | | | | | |

FIG. 5B

```
AGG ATA TCC AAA ATC CCA GAA GAG GTT TGG CAC GAA ATA GGC CCC TCT         720
Arg Ile Ser Lys Ile Pro Glu Glu Val Trp His Glu Ile Gly Pro Ser
225                 230                 235                 240

TTC ATT GAT GCT CCT CCT CTT CCC ACC GTG GAA GAT GGT GAT AGA AAG         768
Phe Ile Asp Ala Pro Pro Leu Pro Thr Val Glu Asp Gly Asp Arg Lys
            245                 250                 255

CTG ACA AGG TTT GAT GAA AGT TCT GCA GAC TTT ATC CGC NCT GGT TTA         816
Leu Thr Arg Phe Asp Glu Ser Ser Ala Asp Phe Ile Arg Xxx Gly Leu
        260                 265                 270

ACT CCT AGG TGG AGT GAT TTG GAC TTG GAC ATC AAC CAG CAT GTC AAC AAT GTG 864
Thr Pro Arg Trp Ser Asp Leu Asp Leu Asp Ile Asn Gln His Val Asn Asn Val
    275                 280                 285

AAG TAC ATT GGC CTC CTT GAG AGT GCT CCG CCG GAG ATC CAC GAG             912
Lys Tyr Ile Gly Leu Leu Glu Ser Ala Pro Pro Glu Ile His Glu
290                 295                 300

AGT CAC GAG ATA GCG TCT CTG ACT CTG GAG TAC AGG AGG GAG TGT GGA         960
Ser His Glu Ile Ala Ser Leu Thr Leu Glu Tyr Arg Arg Glu Cys Gly
305                 310                 315                 320

AGG GAC AGC GTG CTG AAC TCC GCG ACC AAG GTC TCT GAC TCC TCT CAA        1008
Arg Asp Ser Val Leu Asn Ser Ala Thr Lys Val Ser Asp Ser Ser Gln
            325                 330                 335
```

FIG. 5C

```
CTG GGA AAG TCT GCT GTG GAG TGT AAC CAC TTG GTT CGT CTC CAG AAT   1056
Leu Gly Lys Ser Ala Val Glu Cys Asn His Leu Val Arg Leu Gln Asn
                340                 345                 350

GGT GGG GAG ATT GTG AAG GGA AGG ACT GTG TGG AGG CCC AAA CGT CCT   1104
Gly Gly Glu Ile Val Lys Gly Arg Thr Val Trp Arg Pro Lys Arg Pro
                355                 360                 365

CTT TAC AAT GAT GGT GCT GTT GTG GAC GTG NAA GCT AAA ACC TCT       1149
Leu Tyr Asn Asp Gly Ala Val Val Asp Val Xxx Ala Lys Thr Ser
                370                 375                 380

TAAGTCTTAT AGTCCAAGTG AGGAGGAGTT CTATGTATCA GGAAGTTGCT AGGATTCTCA 1209

ATCGCATGTG TCCATTTCTT GTGTGGAATA CTGCTCGTGT TTCTAGACTC GCTATATGTT 1269

TGTTCTTTTA TATATATATA TATATATATA TCTCTCTCTT CCCCCCACCT CTCTCTCTCT 1329

CTCTATATAT ATATATGTTT TATGTAAGTT TTCCCCTTAG TTTCCTTTCC TAAGTAATGC 1389

CATTGTAAAT TACTTCAAAA AAAAAAAAAA AAAAAAAACT CGAG                  1433
```

FIG. 5D

```
GGCACGAGAA ACATGGTGGC TGCCGCAGCA AGTTCTGCAT TCTTCTCCGT TCCAACCCCG    60

GGAATCTCCC CTAAACCCGG GAAGTTCGGT AATGGTGGCT TTCAGGTTAA GGCAAACGCC   120

AATGCCCATC CTAGTCTAAA GTCTGGCAGC CTCGAGACTG AAGATGACAC TTCATCGTCG   180

TCCCCTCCTC CTCGGACTTT CATTAACCAG TTGCCCGACT GGAGTATGCT TCTGTCCGCA   240

ATCACGACTA TCTTCGGGGC AGCTGAGAAG CAGTGGATGA TGCTTGATAG GAAATCTAAG   300

NAGACCCGAC ATGCTCATGG CAACCGTTTG GGGTTGACAG TATTGTTCAG GATGGGGTTT   360

TTTTCAGACA GAGTTTTTCG ATTAGATCTT ACGAAATAGG CGCTGATCGA ACAACCTCAA   420

TAGAGACGCT GATGAACATG TTCCAGGAAA CGTCTTTGAA TCATTGTAAG AGTAACGGTC   480

TTCTCAATGA CGGCTTTGGT CGCACTCCTG AGATGTGTAA GAAGGGCCTC ATTTGGGTGG   540

TTACGAAAAT GCAGGTCGAG GTGAATCGCT ATCCTATTTG GSGTGATTCT ATCGAAGTCA   600

ATACTTGGGT CTCCGAGTCG GGGNAAAANC GGTATGGGTC GTGATTGGCT GATAAGTGAT   660
```

FIG.6A

```
TGCAGTACAG GAGNAAATTC TTGTAAGAGC AACGAGCGTG TGGGCTATGA TGAATCAAAA   720

GACGAGAAGA TTGTCAAAAT TTCCATTTGA GGTTCGACAA GAGATAGCGC CTAATTTTGT   780

CGACTCTGTT CCTGTCATTG AAGACGATCG AAAATTACAC AAGCTTGATG TGAAGACGGG   840

TGATTCCATT CACAATGGTC TAACTCCAAG GTGGAATGAC TTGGATGTCA ATCAGCACGT   900

TAACAATGTG AAATACATTG GGTGGATTCT CAAGAGTGTT CCAACAGATG TTTTTGGGGC   960

CCAGGAGCTA TGTGGA                                                    976
```

FIG.6B

```
GGCGCGCCGG TACCTCTAGA CCTGGGCGATT CAACGTGGTC GGATCATGAC GCTTCCAGAA   60

AACATCGAGC AAGCTCTCAA AGCTGACCTC TTTCGGATCG TACTGAACCC GAACAATCTC  120

GTTATGTCCC GTCGTCTCCG AACAGACATC CTCGTAGCTC GGATTATCGA CGAATCCATG  180

GCTATACCCA ACCTCCGTCT TCGTCACGCC TGGAACCCTC TGGTACGCCA ATTCCGCTCC  240

CCAGAAGCAA CCGGCGCCGA ATTGCGCGAA TTGCTGACCT GGAGACGGAA CATCGTCGTC  300

GGGTCCTTGC GCGATTGCGG CGGAAGCCGG GTCGGGTTGG GGACGAGACC CGAATCCGAG  360

CCTGGTGAAG AGGTTGTTCA TCGGAGATTT ATAGACGGAG ATGGATCGAG CGGTTTTGGG  420

GAAAGGGGAA GTGGGTTTGG CTCTTTTGGA TAGAGAGAGT GCAGCTTTGG AGAGAGACTG  480

GAGAGGTTTA GAGAGAGACG CGGCGGATAT TACCGGAGGA GAGGCCGACGA GAGATAGCAT  540

TATCGAAGGG GAGGGAGAAA GAGTGACGTG GAGAAATAAG AAACCGTTAA GAGTCGGATA  600
```

FIG. 7A

```
TTTATCATAT TAAAAGCCCA ATGGGCCTGA ACCCATTTAA ACAAGACAGA TAAATGGGCC  660
GTGTGTTAAG TTAACAGAGT GTTAACGTTC GGTTTCAAAT GCCAACGCCA TAGGAACAAA  720
ACAAACGTGT CCTCAAGTAA ACCCCTGCCG TTTACACCTC AATGGCTGCA TGGTGAAGCC  780
ATTAACACGT GGCGTAGGAT GCATGACGAC GCCATTGACA CCTGACTCTC TTCCCTTCTC  840
TTCATATATC TCTAATCAAT TCAACTACTC ATTGTCATAG CTATTCGGAA AATACATACA  900
CATCCTTTTC TCTTCGATCT CTCTCAATTC ACAAGAAGCA AAGTCGACGG ATCCCCTGCAG  960
TAAATTACGC CATGACTATT TTCATAGTCC AATAAGGCTG ATGTCGGGAG TCCAGTTTAT 1020
GAGCAATAAG GTGTTTAGAA TTTGATCAAT GTTTATAATA AAAGGGGGAA GATGATATCA 1080
CAGTCTTTTG TTCTTTTTGG CTTTTGTTAA ATTTGTGTGT TTCTATTTGT AAACCTCCTG 1140
TATATGTTGT ACTTCTTTCC CTTTTTAAGT GGTATCGTCT ATATGGTAAA ACGTTATGTT 1200
```

FIG. 7B

| | | | | | |
|---|---|---|---|---|---|
| TGGTCTTTCC | TTTTCTCTGT | TTAGGATAAA | AAGACTGCAT | GTTTTATCTT | TAGTTATATT | 1260
| ATGTTGAGTA | AATGAACTTT | CATAGATCTG | GTTCCGTAGA | GTAGACTAGC | AGCCGAGCTG | 1320
| AGCTGAACTG | AACAGCTGGC | AATGTGAACA | CTGGATGCAA | GATCAGATGT | GAAGATCTCT | 1380
| AATATGGTGG | TGGGATTGAA | CATATCCGTGT | CTATATTTTT | GTTGGCATTA | AGCTCTTAAC | 1440
| ATAGATATAA | CTGATGCAGT | CATTGGTTCA | TACACATATA | TAGTAAGGAA | TTACAATGGC | 1500
| AACCCAAACT | TCAAAAACAG | TAGGCCACCT | GAATTGCCTT | ATCGAATAAG | AGTTTGTTTC | 1560
| CCCCCACTTC | ATGGGATGTA | ATACATGGGA | TTTGGGAGTT | TGAATGAACG | TTGAGACATG | 1620
| GCAGAACCTC | TAGAGGTACC | GGCGCGC | | | | 1647

FIG. 7C

| SAMPLE | % 8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 3854-3 | 0.00 | 1.84 | 0.03 | 0.07 | 4.54 | 0.21 | 2.62 | 69.78 | 17.22 | 1.34 | 0.78 | 1.16 | 0.04 | 0.38 | 0.00 | 0.00 |
| 3854-3 | 0.00 | 1.53 | 0.12 | 7.63 | 21.94 | 0.25 | 7.00 | 44.67 | 12.99 | 1.00 | 1.65 | 0.65 | 0.01 | 0.57 | 0.00 | 0.00 |
| 3854-3 | 0.00 | 0.15 | 0.27 | 16.40 | 31.31 | 0.45 | 7.02 | 25.70 | 15.12 | 0.91 | 1.78 | 0.36 | 0.00 | 0.51 | 0.00 | 0.00 |
| 3854-3 | 0.00 | 0.80 | 0.22 | 14.53 | 29.02 | 0.37 | 7.05 | 29.67 | 14.58 | 0.96 | 1.81 | 0.45 | 0.01 | 0.54 | 0.00 | 0.00 |
| 3854-3 | 0.00 | 1.46 | 0.30 | 18.86 | 32.21 | 0.31 | 7.50 | 22.53 | 12.67 | 0.85 | 2.26 | 0.33 | 0.01 | 0.71 | 0.00 | 0.00 |
| 3854-3 | 0.00 | 3.94 | 0.28 | 15.46 | 28.46 | 0.49 | 7.09 | 26.38 | 14.72 | 0.92 | 1.58 | 0.29 | 0.00 | 0.38 | 0.00 | 0.00 |
| 3854-3 | 0.00 | 2.15 | 0.24 | 19.46 | 33.03 | 0.20 | 6.19 | 23.09 | 11.66 | 0.93 | 2.06 | 0.31 | 0.00 | 0.68 | 0.00 | 0.01 |
| 3854-3 | 0.00 | 3.81 | 0.12 | 16.79 | 32.73 | 0.35 | 7.69 | 23.07 | 10.83 | 0.96 | 2.54 | 0.26 | 0.02 | 0.86 | 0.00 | 0.00 |
| 3854-3 | 0.00 | 6.40 | 0.38 | 20.90 | 30.38 | 0.41 | 6.27 | 21.28 | 10.61 | 0.90 | 1.79 | 0.22 | 0.00 | 0.40 | 0.00 | 0.00 |
| 3854-3 | 0.00 | 6.28 | 0.45 | 23.89 | 37.77 | 0.37 | 9.59 | 13.52 | 4.02 | 0.23 | 2.47 | 0.60 | 0.02 | 0.81 | 0.00 | 0.00 |
| 3854-3 | 0.00 | 1.04 | 0.04 | 0.09 | 4.49 | 0.11 | 2.31 | 69.29 | 18.94 | 1.42 | 0.75 | 1.19 | 0.02 | 0.31 | 0.00 | 0.00 |
| 3854-3 | 0.00 | 3.04 | 0.18 | 19.35 | 32.37 | 0.31 | 7.35 | 22.76 | 10.24 | 0.98 | 2.35 | 0.29 | 0.00 | 0.76 | 0.00 | 0.00 |
| 3854-11 | 0.00 | 1.39 | 0.33 | 17.95 | 30.29 | 0.66 | 6.77 | 23.35 | 15.37 | 1.03 | 1.87 | 0.35 | 0.01 | 0.62 | 0.00 | 0.00 |
| 3854-11 | 0.00 | 1.93 | 0.36 | 21.31 | 31.37 | 0.34 | 6.09 | 22.92 | 12.38 | 1.05 | 1.96 | 0.06 | 0.02 | 0.20 | 0.01 | 0.01 |
| 3854-11 | 0.00 | 1.22 | 0.27 | 18.75 | 31.33 | 0.50 | 6.91 | 25.50 | 13.08 | 0.89 | 1.12 | 0.31 | 0.01 | 0.11 | 0.00 | 0.01 |
| 3854-11 | 0.00 | 1.53 | 0.23 | 17.30 | 33.28 | 0.56 | 1.25 | 29.63 | 14.07 | 0.41 | 0.90 | 0.30 | 0.01 | 0.49 | 0.00 | 0.04 |
| 3854-11 | 0.00 | 0.50 | 0.03 | 0.04 | 3.93 | 0.07 | 2.92 | 76.55 | 12.30 | 0.99 | 0.95 | 1.27 | 0.02 | 0.42 | 0.00 | 0.00 |
| 3854-11 | 0.00 | 0.91 | 0.35 | 16.96 | 30.43 | 0.45 | 7.67 | 25.02 | 15.14 | 0.85 | 1.57 | 0.31 | 0.00 | 0.34 | 0.01 | 0.00 |
| 3854-11 | 0.00 | 1.44 | 0.38 | 23.03 | 33.37 | 0.45 | 7.07 | 19.31 | 11.50 | 0.98 | 1.73 | 0.23 | 0.00 | 0.52 | 0.01 | 0.00 |
| 3854-11 | 0.00 | 2.17 | 0.30 | 18.27 | 32.78 | 0.43 | 7.17 | 24.74 | 10.03 | 0.82 | 2.30 | 0.29 | 0.01 | 0.70 | 0.01 | 0.00 |
| 3854-11 | 0.00 | 1.73 | 0.29 | 21.83 | 32.82 | 0.30 | 7.41 | 20.85 | 11.18 | 0.71 | 2.07 | 0.19 | 0.00 | 0.61 | 0.01 | 0.00 |
| 3854-11 | 0.00 | 1.50 | 0.42 | 23.00 | 32.88 | 0.42 | 6.86 | 17.89 | 13.69 | 0.86 | 1.74 | 0.23 | 0.00 | 0.50 | 0.01 | 0.00 |
| 3854-11 | 0.00 | 2.16 | 0.34 | 21.37 | 36.03 | 0.27 | 8.12 | 19.29 | 8.56 | 0.60 | 2.25 | 0.25 | 0.00 | 0.75 | 0.01 | 0.00 |
| 3854-11 | 0.00 | 2.71 | 0.32 | 20.56 | 33.43 | 0.79 | 7.70 | 20.91 | 10.42 | 0.88 | 1.66 | 0.17 | 0.01 | 0.44 | 0.00 | 0.00 |

FIGURE 8

| SAMPLE | % 8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 5233-6 | 0.00 | 0.19 | 1.60 | 15.35 | 13.19 | 0.53 | 1.33 | 41.03 | 14.00 | 11.85 | 0.15 | 0.76 | 0.00 | 0.00 | 0.00 | 0.03 |
| 5233-6 | 0.00 | 0.00 | 1.37 | 15.02 | 13.03 | 0.53 | 1.57 | 42.48 | 12.42 | 12.59 | 0.30 | 0.68 | 0.00 | 0.00 | 0.00 | 0.02 |
| 5233-6 | 0.00 | 0.00 | 1.32 | 13.77 | 12.79 | 0.41 | 1.26 | 42.40 | 14.19 | 12.80 | 0.27 | 0.80 | 0.00 | 0.00 | 0.00 | 0.00 |
| 5233-6 | 0.00 | 0.00 | 1.37 | 14.16 | 12.64 | 0.30 | 1.39 | 43.59 | 13.27 | 12.30 | 0.29 | 0.60 | 0.02 | 0.01 | 0.00 | 0.03 |
| 5233-6 | 0.00 | 0.00 | 2.05 | 18.99 | 14.48 | 0.41 | 1.22 | 37.18 | 13.57 | 11.46 | 0.14 | 0.47 | 0.03 | 0.00 | 0.00 | 0.00 |
| 5233-6 | 0.00 | 0.00 | 0.75 | 8.54 | 12.62 | 0.43 | 1.37 | 46.23 | 18.76 | 10.22 | 0.39 | 0.66 | 0.00 | 0.00 | 0.00 | 0.04 |
| 5233-6 | 0.00 | 0.00 | 0.18 | 2.53 | 9.04 | 0.19 | 1.53 | 52.87 | 17.70 | 14.68 | 0.33 | 0.92 | 0.00 | 0.02 | 0.00 | 0.00 |
| 5233-6 | 0.00 | 0.00 | 0.15 | 2.93 | 10.02 | 0.26 | 1.28 | 49.86 | 21.85 | 12.61 | 0.28 | 0.78 | 0.00 | 0.00 | 0.00 | 0.00 |
| 5233-6 | 0.00 | 0.00 | 1.95 | 17.52 | 13.40 | 0.55 | 1.54 | 40.26 | 12.87 | 10.98 | 0.25 | 0.66 | 0.02 | 0.00 | 0.00 | 0.00 |
| 5233-6 | 0.00 | 0.00 | 0.00 | 0.13 | 7.85 | 0.19 | 1.46 | 54.44 | 19.60 | 15.01 | 0.31 | 0.91 | 0.05 | 0.07 | 0.00 | 0.00 |
| 5233-6 | 0.00 | 0.00 | 1.25 | 12.71 | 12.78 | 0.53 | 1.06 | 42.38 | 15.85 | 12.75 | 0.20 | 0.39 | 0.04 | 0.04 | 0.00 | 0.00 |
| 5233-6 | 0.00 | 0.00 | 1.61 | 16.02 | 13.44 | 0.49 | 1.43 | 40.44 | 13.83 | 11.73 | 0.32 | 0.70 | 0.00 | 0.00 | 0.00 | 0.00 |
| 5233-6 | 0.00 | 0.28 | 0.48 | 5.65 | 10.20 | 0.32 | 1.61 | 50.49 | 16.71 | 13.30 | 0.19 | 0.76 | 0.00 | 0.02 | 0.00 | 0.00 |
| 5233-6 | 0.00 | 0.13 | 1.55 | 15.42 | 13.48 | 0.41 | 1.40 | 40.74 | 13.95 | 11.79 | 0.29 | 0.79 | 0.02 | 0.00 | 0.00 | 0.00 |
| 5233-6 | 0.00 | 0.00 | 1.06 | 10.96 | 12.39 | 0.53 | 1.54 | 42.30 | 16.35 | 13.76 | 0.30 | 0.77 | 0.02 | 0.03 | 0.00 | 0.00 |
| 5233-6 | 0.00 | 0.00 | 1.59 | 15.50 | 13.40 | 0.44 | 1.31 | 39.72 | 15.62 | 11.50 | 0.19 | 0.67 | 0.00 | 0.03 | 0.00 | 0.00 |
| 5233-6 | 0.00 | 0.00 | 2.62 | 21.42 | 14.67 | 0.42 | 1.32 | 35.45 | 12.71 | 10.61 | 0.17 | 0.57 | 0.03 | 0.06 | 0.00 | 0.00 |
| 5233-6 | 0.00 | 0.00 | 1.46 | 14.23 | 12.72 | 0.44 | 1.31 | 42.86 | 13.86 | 12.19 | 0.25 | 0.58 | 0.10 | 0.02 | 0.00 | 0.00 |
| 5233-6 | 0.99 | 0.00 | 2.47 | 20.66 | 14.57 | 0.47 | 1.25 | 34.24 | 13.72 | 10.78 | 0.15 | 0.56 | 0.08 | 0.00 | 0.01 | 0.00 |
| 5233-6 | 0.00 | 0.36 | 0.00 | 0.22 | 7.73 | 0.18 | 1.35 | 53.50 | 20.65 | 15.16 | 0.16 | 0.71 | 0.00 | 0.03 | 0.00 | 0.05 |
| 5233-6 | 0.22 | 1.00 | 0.40 | 5.08 | 9.95 | 0.25 | 1.26 | 50.05 | 16.93 | 13.69 | 0.21 | 0.87 | 0.02 | 0.00 | 0.03 | 0.00 |
| 5233-6 | 0.00 | 0.00 | 2.73 | 20.62 | 14.73 | 0.52 | 1.50 | 35.20 | 14.55 | 9.33 | 0.22 | 0.55 | 0.00 | 0.05 | 0.00 | 0.00 |
| 5233-6 | 0.53 | 0.32 | 1.60 | 14.10 | 12.18 | 0.51 | 1.39 | 43.88 | 12.56 | 12.27 | 0.30 | 0.34 | 0.03 | 0.00 | 0.00 | 0.00 |
| 5233-6 | 2.04 | 0.21 | 0.07 | 0.53 | 8.51 | 0.13 | 0.82 | 48.89 | 22.20 | 15.42 | 0.39 | 0.52 | 0.06 | 0.05 | 0.11 | 0.06 |
| 5233-6 | 0.29 | 0.45 | 1.66 | 15.50 | 12.49 | 0.33 | 0.27 | 44.04 | 12.90 | 11.39 | 0.07 | 0.52 | 0.04 | 0.02 | 0.02 | 0.03 |

FIGURE 9A

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 5233-5 | 0.00 | 0.00 | 1.01 | 10.88 | 12.07 | 0.45 | 1.63 | 45.12 | 15.93 | 12.05 | 0.22 | 0.66 | 0.00 | 0.00 | 0.00 | 0.00 |
| 5233-5 | 0.00 | 0.00 | 0.62 | 6.78 | 10.89 | 0.42 | 1.52 | 48.26 | 16.45 | 14.04 | 0.31 | 0.71 | 0.00 | 0.00 | 0.00 | 0.00 |
| 5233-5 | 0.00 | 0.00 | 0.32 | 5.22 | 11.15 | 0.62 | 1.33 | 46.32 | 19.06 | 14.81 | 0.38 | 0.79 | 0.00 | 0.00 | 0.00 | 0.00 |
| 5233-5 | 0.00 | 0.00 | 1.10 | 11.92 | 13.11 | 0.48 | 1.17 | 41.16 | 18.63 | 12.06 | 0.08 | 0.22 | 0.06 | 0.00 | 0.00 | 0.00 |
| 5233-5 | 0.00 | 0.00 | 0.47 | 6.39 | 12.06 | 0.49 | 1.55 | 44.78 | 20.34 | 13.11 | 0.16 | 0.62 | 0.00 | 0.05 | 0.05 | 0.00 |
| 5233-5 | 0.00 | 0.00 | 1.60 | 14.96 | 13.99 | 0.46 | 1.26 | 38.28 | 16.52 | 12.19 | 0.09 | 0.61 | 0.00 | 0.00 | 0.03 | 0.03 |
| 5233-5 | 0.00 | 0.00 | 1.74 | 15.07 | 12.96 | 0.46 | 1.48 | 40.24 | 15.80 | 11.54 | 0.08 | 0.54 | 0.00 | 0.00 | 0.00 | 0.00 |
| 5233-5 | 0.00 | 0.00 | 1.21 | 12.56 | 12.78 | 0.48 | 1.48 | 43.93 | 14.62 | 11.86 | 0.33 | 0.76 | 0.00 | 0.00 | 0.00 | 0.04 |
| 5233-5 | 0.00 | 0.00 | 0.97 | 11.85 | 14.12 | 0.56 | 1.23 | 41.07 | 17.69 | 11.87 | 0.08 | 0.49 | 0.00 | 0.04 | 0.00 | 0.00 |
| 5233-5 | 0.00 | 0.00 | 0.83 | 8.97 | 12.39 | 0.42 | 1.58 | 48.28 | 16.85 | 9.56 | 0.34 | 0.69 | 0.04 | 0.00 | 0.00 | 0.00 |
| 5233-5 | 0.00 | 0.00 | 0.93 | 10.31 | 12.40 | 0.48 | 1.79 | 47.27 | 14.61 | 11.15 | 0.33 | 0.67 | 0.00 | 0.00 | 0.00 | 0.00 |
| 5233-5 | 1.84 | 0.00 | 0.08 | 0.13 | 7.23 | 0.17 | 1.62 | 53.76 | 19.19 | 14.81 | 0.31 | 0.85 | 0.00 | 0.00 | 0.00 | 0.03 |
| 5233-5 | 0.00 | 0.00 | 1.08 | 11.33 | 11.69 | 0.41 | 1.37 | 48.20 | 13.69 | 11.39 | 0.25 | 0.57 | 0.00 | 0.04 | 0.00 | 0.00 |
| 5233-5 | 0.00 | 0.00 | 0.92 | 11.49 | 13.95 | 0.63 | 1.15 | 39.54 | 18.18 | 13.09 | 0.24 | 0.68 | 0.08 | 0.01 | 0.00 | 0.00 |
| 5233-5 | 0.00 | 0.00 | 0.63 | 8.78 | 12.57 | 0.33 | 1.10 | 43.92 | 18.31 | 13.42 | 0.19 | 0.67 | 0.07 | 0.00 | 0.00 | 0.00 |
| 5233-5 | 0.00 | 0.00 | 1.80 | 17.17 | 14.47 | 0.54 | 1.23 | 38.34 | 15.29 | 10.44 | 0.14 | 0.56 | 0.00 | 0.00 | 0.00 | 0.01 |
| 5233-5 | 0.00 | 0.00 | 1.95 | 17.01 | 14.57 | 0.70 | 1.29 | 35.66 | 17.51 | 10.43 | 0.21 | 0.64 | 0.02 | 0.00 | 0.00 | 0.00 |
| 5233-5 | 0.00 | 0.00 | 0.87 | 11.22 | 13.23 | 0.40 | 1.29 | 40.45 | 18.98 | 12.75 | 0.16 | 0.54 | 0.00 | 0.09 | 0.00 | 0.03 |
| 5233-5 | 0.00 | 0.00 | 1.03 | 11.39 | 12.29 | 0.41 | 1.70 | 44.98 | 14.84 | 11.99 | 0.43 | 0.83 | 0.02 | 0.03 | 0.02 | 0.00 |
| 5233-5 | 0.00 | 0.00 | 0.76 | 8.93 | 13.19 | 0.20 | 1.26 | 41.27 | 19.80 | 14.12 | 0.07 | 0.34 | 0.00 | 0.00 | 0.08 | 0.00 |
| 5233-5 | 0.00 | 0.00 | 1.10 | 11.90 | 11.95 | 0.46 | 1.68 | 45.86 | 13.59 | 12.37 | 0.32 | 0.72 | 0.00 | 0.04 | 0.00 | 0.00 |
| 5233-5 | 0.00 | 0.00 | 1.05 | 10.72 | 12.43 | 0.44 | 1.49 | 43.90 | 15.96 | 13.12 | 0.15 | 0.70 | 0.00 | 0.05 | 0.00 | 0.00 |
| 5233-5 | 0.00 | 0.00 | 1.04 | 11.64 | 12.34 | 0.44 | 1.66 | 45.20 | 14.22 | 12.35 | 0.31 | 0.69 | 0.04 | 0.07 | 0.00 | 0.00 |
| 5233-5 | 0.00 | 0.37 | 0.45 | 4.76 | 11.20 | 0.12 | 0.94 | 45.76 | 21.36 | 14.10 | 0.09 | 0.83 | 0.00 | 0.02 | 0.02 | 0.00 |
| 5233-5 | 0.00 | 0.00 | 1.51 | 15.42 | 14.10 | 0.53 | 1.48 | 39.41 | 14.68 | 12.21 | 0.08 | 0.58 | 0.00 | 0.00 | 0.02 | 0.00 |

FIGURE 9B

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 3863-10 | 0.00 | 0.00 | 0.23 | 36.72 | 21.59 | 0.17 | 1.66 | 20.65 | 16.21 | 1.38 | 0.65 | 0.46 | 0.02 | 0.25 | 0.01 | 0.01 |
| 3863-10 | 0.00 | 0.00 | 0.33 | 42.87 | 18.70 | 0.30 | 1.72 | 18.86 | 14.79 | 1.36 | 0.57 | 0.40 | 0.02 | 0.05 | 0.01 | 0.01 |
| 3863-10 | 0.00 | 0.00 | 0.24 | 36.56 | 19.03 | 0.29 | 1.76 | 22.75 | 16.47 | 1.74 | 0.58 | 0.39 | 0.02 | 0.15 | 0.01 | 0.01 |
| 3863-10 | 0.00 | 0.00 | 0.32 | 42.65 | 19.06 | 0.33 | 2.26 | 18.58 | 14.01 | 1.43 | 0.68 | 0.33 | 0.03 | 0.27 | 0.02 | 0.03 |
| 3863-10 | 0.00 | 0.00 | 0.33 | 42.48 | 19.74 | 0.40 | 2.34 | 18.72 | 13.55 | 1.38 | 0.66 | 0.27 | 0.05 | 0.06 | 0.01 | 0.02 |
| 3863-10 | 0.00 | 0.00 | 0.33 | 42.88 | 18.88 | 0.30 | 1.95 | 17.73 | 15.44 | 1.44 | 0.64 | 0.27 | 0.04 | 0.08 | 0.02 | 0.01 |
| 3863-10 | 0.00 | 0.00 | 0.22 | 40.89 | 20.63 | 0.24 | 1.81 | 17.77 | 15.76 | 1.39 | 0.65 | 0.35 | 0.06 | 0.22 | 0.01 | 0.01 |
| 3863-10 | 0.00 | 0.00 | 0.20 | 29.49 | 17.06 | 0.24 | 1.86 | 28.63 | 19.46 | 1.68 | 0.58 | 0.66 | 0.05 | 0.06 | 0.01 | 0.02 |
| 3863-10 | 0.00 | 0.00 | 0.39 | 41.52 | 18.34 | 0.32 | 2.15 | 19.57 | 15.19 | 1.54 | 0.56 | 0.31 | 0.03 | 0.07 | 0.00 | 0.02 |
| 3863-10 | 0.00 | 0.00 | 0.30 | 37.55 | 20.00 | 0.23 | 1.79 | 23.58 | 13.87 | 1.47 | 0.59 | 0.51 | 0.03 | 0.05 | 0.02 | 0.02 |
| 3863-10 | 0.00 | 0.00 | 0.13 | 21.84 | 17.17 | 0.25 | 2.50 | 37.17 | 17.07 | 1.80 | 0.75 | 0.80 | 0.12 | 0.38 | 0.02 | 0.02 |
| 3863-10 | 0.00 | 0.00 | 0.14 | 25.13 | 17.66 | 0.23 | 2.00 | 31.52 | 20.07 | 1.42 | 0.65 | 0.81 | 0.05 | 0.29 | 0.01 | 0.00 |
| 3863-7 | 0.00 | 0.00 | 0.18 | 21.00 | 15.58 | 0.42 | 2.80 | 37.13 | 18.53 | 2.66 | 0.87 | 0.47 | 0.07 | 0.23 | 0.04 | 0.02 |
| 3863-7 | 0.00 | 0.00 | 0.14 | 16.64 | 14.67 | 0.38 | 2.99 | 38.90 | 21.75 | 2.91 | 0.81 | 0.56 | 0.08 | 0.13 | 0.03 | 0.02 |
| 3863-7 | 0.00 | 0.00 | 0.12 | 18.54 | 15.25 | 0.37 | 3.11 | 39.03 | 19.32 | 2.58 | 0.88 | 0.58 | 0.05 | 0.12 | 0.04 | 0.02 |
| 3863-7 | 0.00 | 0.00 | 0.12 | 18.55 | 14.81 | 0.38 | 3.16 | 37.62 | 20.65 | 3.20 | 0.82 | 0.42 | 0.02 | 0.19 | 0.03 | 0.02 |
| 3863-7 | 0.00 | 0.00 | 0.02 | 0.16 | 6.07 | 0.35 | 3.12 | 63.30 | 22.03 | 2.68 | 0.96 | 1.06 | 0.03 | 0.15 | 0.02 | 0.05 |
| 3863-7 | 0.00 | 0.00 | 0.14 | 16.90 | 14.90 | 0.41 | 2.97 | 40.23 | 20.11 | 2.83 | 0.79 | 0.63 | 0.05 | 0.02 | 0.01 | 0.02 |
| 3863-7 | 0.00 | 0.00 | 0.15 | 12.57 | 13.66 | 0.57 | 3.48 | 44.45 | 20.42 | 3.07 | 0.98 | 0.48 | 0.02 | 0.10 | 0.03 | 0.02 |
| 3863-7 | 0.00 | 0.00 | 0.11 | 10.22 | 12.64 | 0.58 | 3.83 | 46.53 | 20.86 | 3.35 | 1.14 | 0.46 | 0.03 | 0.19 | 0.03 | 0.04 |
| 3863-7 | 0.00 | 0.00 | 0.09 | 15.48 | 14.28 | 0.83 | 3.00 | 39.64 | 21.56 | 3.77 | 0.76 | 0.39 | 0.04 | 0.04 | 0.05 | 0.05 |
| 3863-7 | 0.00 | 0.00 | 0.08 | 10.89 | 12.79 | 0.54 | 3.00 | 46.69 | 21.23 | 3.54 | 0.76 | 0.29 | 0.04 | 0.03 | 0.09 | 0.03 |
| 3863-7 | 0.00 | 0.00 | 0.14 | 9.77 | 12.73 | 0.51 | 3.74 | 46.96 | 20.90 | 3.37 | 1.02 | 0.50 | 0.04 | 0.26 | 0.04 | 0.01 |
| 3863-7 | 0.00 | 0.00 | 0.16 | 15.86 | 14.25 | 0.51 | 3.46 | 41.12 | 19.50 | 3.32 | 0.89 | 0.60 | 0.07 | 0.17 | 0.03 | 0.04 |
| 3863-4 | 0.00 | 0.00 | 0.17 | 15.69 | 14.91 | 1.21 | 2.32 | 31.36 | 29.72 | 3.01 | 0.85 | 0.49 | 0.05 | 0.14 | 0.05 | 0.02 |
| 3863-4 | 0.00 | 0.00 | 0.23 | 38.63 | 19.96 | 0.29 | 1.41 | 20.94 | 15.70 | 1.39 | 0.62 | 0.54 | 0.03 | 0.25 | 0.01 | 0.01 |

FIGURE 10A

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 3863-4 | 0.00 | 0.00 | 0.00 | 25.75 | 33.27 | 0.11 | 8.98 | 7.98 | 3.42 | 0.06 | 2.33 | 17.44 | 0.08 | 0.18 | 0.13 | 0.27 |
| 3863-4 | 0.00 | 0.00 | 0.17 | 30.59 | 19.06 | 0.26 | 1.70 | 27.57 | 17.30 | 1.41 | 0.76 | 0.74 | 0.04 | 0.38 | 0.01 | 0.01 |
| 3863-4 | 0.00 | 0.00 | 0.16 | 28.93 | 17.51 | 0.27 | 2.25 | 28.14 | 19.06 | 1.87 | 0.78 | 0.59 | 0.04 | 0.39 | 0.01 | 0.01 |
| 3863-4 | 0.00 | 0.00 | 0.19 | 31.48 | 18.44 | 0.21 | 2.06 | 28.98 | 15.77 | 1.37 | 0.71 | 0.65 | 0.03 | 0.09 | 0.01 | 0.01 |
| 3863-4 | 0.00 | 0.00 | 0.18 | 38.07 | 21.62 | 0.22 | 1.55 | 22.37 | 13.14 | 1.11 | 0.79 | 0.52 | 0.03 | 0.39 | 0.01 | 0.00 |
| 3863-4 | 0.00 | 0.00 | 0.18 | 29.22 | 18.35 | 0.34 | 2.02 | 29.70 | 16.70 | 1.58 | 0.74 | 0.79 | 0.06 | 0.29 | 0.01 | 0.01 |
| 3863-4 | 0.00 | 0.00 | 0.23 | 34.61 | 19.74 | 0.17 | 1.70 | 24.07 | 16.55 | 1.21 | 0.70 | 0.65 | 0.04 | 0.31 | 0.01 | 0.01 |
| 3863-4 | 0.00 | 0.00 | 0.18 | 30.56 | 18.47 | 0.19 | 2.08 | 28.61 | 16.81 | 1.50 | 0.68 | 0.63 | 0.04 | 0.24 | 0.01 | 0.01 |
| 3863-4 | 0.00 | 0.00 | 0.21 | 37.45 | 21.35 | 0.19 | 1.61 | 23.60 | 12.97 | 1.07 | 0.71 | 0.54 | 0.03 | 0.25 | 0.01 | 0.01 |
| 3863-4 | 0.00 | 0.00 | 0.18 | 29.70 | 18.98 | 0.19 | 2.03 | 29.00 | 16.70 | 1.36 | 0.77 | 0.73 | 0.00 | 0.36 | 0.01 | 0.01 |
| 3863-4 | 0.00 | 0.00 | 0.22 | 37.87 | 20.27 | 0.23 | 1.93 | 22.06 | 14.51 | 1.31 | 0.77 | 0.48 | 0.02 | 0.31 | 0.01 | 0.01 |
| 3863-4 | 0.00 | 0.00 | 0.21 | 39.14 | 21.36 | 0.19 | 1.64 | 21.46 | 13.42 | 1.13 | 0.69 | 0.37 | 0.09 | 0.30 | 0.01 | 0.00 |
| 3863-4 | 0.00 | 0.00 | 0.20 | 38.94 | 20.69 | 0.25 | 1.38 | 18.57 | 17.11 | 1.37 | 0.67 | 0.39 | 0.04 | 0.36 | 0.01 | 0.01 |
| 3863-4 | 0.00 | 0.00 | 0.01 | 0.21 | 5.81 | 0.32 | 4.29 | 65.31 | 18.68 | 2.19 | 1.38 | 1.19 | 0.01 | 0.59 | 0.01 | 0.01 |
| 3863-4 | 0.00 | 0.00 | 0.07 | 0.17 | 8.14 | 0.61 | 4.97 | 54.61 | 25.74 | 3.28 | 1.50 | 0.67 | 0.05 | 0.14 | 0.04 | 0.02 |
| 3863-4 | 0.00 | 0.00 | 0.16 | 30.31 | 19.06 | 0.26 | 1.92 | 27.23 | 17.65 | 1.58 | 0.76 | 0.72 | 0.03 | 0.32 | 0.00 | 0.01 |
| 3863-4 | 0.00 | 0.00 | 0.20 | 32.77 | 18.77 | 0.23 | 1.92 | 27.37 | 15.76 | 1.35 | 0.66 | 0.67 | 0.02 | 0.26 | 0.01 | 0.01 |
| 3863-4 | 0.00 | 0.00 | 0.28 | 37.97 | 19.58 | 0.34 | 1.74 | 21.75 | 15.46 | 1.60 | 0.66 | 0.46 | 0.03 | 0.10 | 0.00 | 0.01 |
| 3863-4 | 0.00 | 0.00 | 0.25 | 39.54 | 19.76 | 0.26 | 1.79 | 19.97 | 15.78 | 1.50 | 0.63 | 0.39 | 0.01 | 0.10 | 0.00 | 0.01 |
| 3863-4 | 0.00 | 0.00 | 0.19 | 31.46 | 18.50 | 0.17 | 2.00 | 30.06 | 14.81 | 1.30 | 0.75 | 0.66 | 0.01 | 0.07 | 0.00 | 0.01 |
| 3863-4 | 0.00 | 0.00 | 0.23 | 34.79 | 19.64 | 0.38 | 1.96 | 22.66 | 17.04 | 1.78 | 0.85 | 0.49 | 0.03 | 0.10 | 0.02 | 0.01 |
| 3863-4 | 0.00 | 0.00 | 0.21 | 31.55 | 18.70 | 0.23 | 2.16 | 27.97 | 15.73 | 1.44 | 0.83 | 0.70 | 0.04 | 0.40 | 0.01 | 0.01 |
| 3863-4 | 0.00 | 0.00 | 0.18 | 29.27 | 18.66 | 0.25 | 2.22 | 31.60 | 14.42 | 1.74 | 0.79 | 0.76 | 0.04 | 0.08 | 0.01 | 0.00 |
| 3863-4 | 0.00 | 0.00 | 0.58 | 50.92 | 32.69 | 0.46 | 4.72 | 5.73 | 2.75 | 0.16 | 1.17 | 0.39 | 0.06 | 0.28 | 0.05 | 0.05 |
| 3863-4 | 0.00 | 0.00 | 0.28 | 40.26 | 19.58 | 0.20 | 1.48 | 20.62 | 15.20 | 1.24 | 0.58 | 0.48 | 0.04 | 0.05 | 0.01 | 0.00 |
| 3863-4 | 0.00 | 0.00 | 0.20 | 32.09 | 18.27 | 0.17 | 2.03 | 28.26 | 15.99 | 1.43 | 0.71 | 0.74 | 0.04 | 0.05 | 0.01 | 0.01 |

FIGURE 10B

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 3863-4 | 0.00 | 0.00 | 0.04 | 0.38 | 4.65 | 0.26 | 3.07 | 62.89 | 24.59 | 1.83 | 0.85 | 1.12 | 0.01 | 0.26 | 0.04 | 0.01 |
| 3863-4 | 0.00 | 0.00 | 0.19 | 30.34 | 18.77 | 0.28 | 1.83 | 25.81 | 19.41 | 1.46 | 0.73 | 0.77 | 0.03 | 0.36 | 0.01 | 0.02 |
| 3863-4 | 0.00 | 0.00 | 0.03 | 0.38 | 5.07 | 0.29 | 3.36 | 64.47 | 22.34 | 1.91 | 0.95 | 1.09 | 0.05 | 0.04 | 0.00 | 0.01 |
| 3863-4 | 0.00 | 0.00 | 0.22 | 37.53 | 20.33 | 0.30 | 1.87 | 21.73 | 15.14 | 1.30 | 0.80 | 0.46 | 0.03 | 0.29 | 0.01 | 0.01 |
| 3863-4 | 0.00 | 0.00 | 0.00 | 0.38 | 5.09 | 0.31 | 3.37 | 66.30 | 20.02 | 1.78 | 1.03 | 1.17 | 0.02 | 0.52 | 0.01 | 0.01 |
| 3863-4 | 0.00 | 0.00 | 0.02 | 0.38 | 4.79 | 0.23 | 3.87 | 68.32 | 17.76 | 1.98 | 1.07 | 1.16 | 0.01 | 0.37 | 0.02 | 0.01 |
| 3863-4 | 0.00 | 0.00 | 0.17 | 25.22 | 18.00 | 0.35 | 2.59 | 34.34 | 15.42 | 1.65 | 0.99 | 0.74 | 0.02 | 0.47 | 0.02 | 0.02 |
| 3863-4 | 0.00 | 0.00 | 0.17 | 29.76 | 18.99 | 0.21 | 2.32 | 31.59 | 13.69 | 1.20 | 0.86 | 0.78 | 0.04 | 0.38 | 0.01 | 0.01 |
| 3863-4 | 0.00 | 0.00 | 0.03 | 0.43 | 4.99 | 0.28 | 3.24 | 64.01 | 22.34 | 2.08 | 0.98 | 1.16 | 0.03 | 0.41 | 0.01 | 0.01 |
| 3863-4 | 0.00 | 0.00 | 0.02 | 0.10 | 5.32 | 0.31 | 3.67 | 61.45 | 24.35 | 2.55 | 0.96 | 1.14 | 0.02 | 0.09 | 0.01 | 0.02 |
| 3863-8 | 0.00 | 0.00 | 0.03 | 0.10 | 5.94 | 0.38 | 3.09 | 56.78 | 28.77 | 2.79 | 0.89 | 0.99 | 0.04 | 0.15 | 0.03 | 0.01 |
| 3863-8 | 0.00 | 0.00 | 0.04 | 0.14 | 5.78 | 0.36 | 3.44 | 64.06 | 21.60 | 2.45 | 0.91 | 1.02 | 0.02 | 0.15 | 0.02 | 0.02 |
| 3863-8 | 0.00 | 0.00 | 0.04 | 0.09 | 5.37 | 0.33 | 3.45 | 63.65 | 22.77 | 2.20 | 0.90 | 0.99 | 0.04 | 0.15 | 0.01 | 0.01 |
| 3863-8 | 0.00 | 0.00 | 0.08 | 0.09 | 6.57 | 0.45 | 4.04 | 58.85 | 24.60 | 3.22 | 1.00 | 0.84 | 0.04 | 0.19 | 0.02 | 0.02 |
| 3863-8 | 0.00 | 0.00 | 0.03 | 0.07 | 5.61 | 0.32 | 3.45 | 60.39 | 25.33 | 2.63 | 1.02 | 1.02 | 0.04 | 0.07 | 0.02 | 0.02 |
| 3863-8 | 0.00 | 0.00 | 0.02 | 0.12 | 5.80 | 0.42 | 3.87 | 66.16 | 18.67 | 2.47 | 1.03 | 0.89 | 0.10 | 0.40 | 0.01 | 0.02 |
| 3863-8 | 0.00 | 0.00 | 0.03 | 0.09 | 5.52 | 0.33 | 3.26 | 61.36 | 24.50 | 2.43 | 0.93 | 1.07 | 0.03 | 0.45 | 0.01 | 0.01 |
| 3863-8 | 0.00 | 0.00 | 0.02 | 0.15 | 5.25 | 0.25 | 3.14 | 62.11 | 24.32 | 2.41 | 0.85 | 1.08 | 0.04 | 0.36 | 0.01 | 0.01 |
| 3863-8 | 0.00 | 0.00 | 0.04 | 0.19 | 6.47 | 0.43 | 4.15 | 56.05 | 27.43 | 2.97 | 1.12 | 0.84 | 0.02 | 0.25 | 0.02 | 0.02 |
| 3863-8 | 0.00 | 0.00 | 0.03 | 0.16 | 6.13 | 0.38 | 3.48 | 59.94 | 24.95 | 2.68 | 0.97 | 0.86 | 0.05 | 0.33 | 0.02 | 0.02 |
| 3863-8 | 0.00 | 0.00 | 0.03 | 0.09 | 5.65 | 0.36 | 3.71 | 61.34 | 24.00 | 2.58 | 0.98 | 1.00 | 0.08 | 0.18 | 0.01 | 0.02 |
| 3863-2 | 0.00 | 0.00 | 0.22 | 26.95 | 17.05 | 0.28 | 2.31 | 32.94 | 15.90 | 2.37 | 0.84 | 0.64 | 0.11 | 0.36 | 0.02 | 0.01 |
| 3863-2 | 0.00 | 0.00 | 0.09 | 0.81 | 8.05 | 0.74 | 3.06 | 58.33 | 22.87 | 3.86 | 0.94 | 0.82 | 0.04 | 0.29 | 0.06 | 0.03 |
| 3863-2 | 0.00 | 0.00 | 0.13 | 19.27 | 15.52 | 0.42 | 2.89 | 40.66 | 16.82 | 2.47 | 0.91 | 0.68 | 0.02 | 0.17 | 0.02 | 0.01 |
| 3863-2 | 0.00 | 0.00 | 0.15 | 24.15 | 17.73 | 0.32 | 2.18 | 36.80 | 14.75 | 1.69 | 0.85 | 0.84 | 0.04 | 0.47 | 0.01 | 0.01 |
| 3863-2 | 0.00 | 0.00 | 0.19 | 25.37 | 17.25 | 0.25 | 2.66 | 32.97 | 17.44 | 1.67 | 0.94 | 0.78 | 0.01 | 0.45 | 0.00 | 0.01 |

FIGURE 10C

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 |
|---|---|---|---|---|---|---|---|---|---|---|---|---|---|---|---|---|
| 3863-2 | 0.00 | 0.00 | 0.04 | 0.59 | 7.21 | 0.67 | 2.91 | 56.35 | 26.68 | 2.99 | 1.06 | 0.92 | 0.07 | 0.44 | 0.02 | 0.05 |
| 3863-2 | 0.00 | 0.00 | 0.20 | 27.82 | 18.08 | 0.37 | 2.56 | 33.69 | 13.30 | 1.77 | 0.97 | 0.68 | 0.02 | 0.51 | 0.01 | 0.03 |
| 3863-2 | 0.00 | 0.00 | 0.13 | 20.71 | 17.03 | 0.29 | 2.72 | 37.93 | 16.70 | 1.84 | 1.13 | 0.80 | 0.01 | 0.68 | 0.01 | 0.01 |
| 3863-2 | 0.00 | 0.00 | 0.17 | 26.25 | 17.87 | 0.22 | 2.26 | 37.01 | 12.61 | 1.48 | 0.85 | 0.82 | 0.05 | 0.41 | 0.01 | 0.00 |
| 3863-2 | 0.00 | 0.00 | 0.14 | 22.96 | 16.51 | 0.28 | 2.58 | 38.26 | 15.70 | 1.91 | 0.80 | 0.76 | 0.03 | 0.06 | 0.01 | 0.01 |
| 3863-2 | 0.00 | 0.00 | 0.15 | 22.04 | 16.77 | 0.20 | 2.61 | 40.01 | 14.57 | 1.96 | 0.81 | 0.71 | 0.04 | 0.11 | 0.02 | 0.01 |
| 3863-2 | 0.00 | 0.00 | 0.02 | 0.28 | 5.70 | 0.34 | 3.24 | 65.13 | 20.60 | 2.42 | 1.08 | 1.03 | 0.01 | 0.08 | 0.03 | 0.02 |
| 3863-5 | 0.00 | 0.00 | 0.17 | 23.40 | 16.42 | 0.41 | 2.44 | 32.08 | 21.06 | 2.40 | 0.80 | 0.61 | 0.02 | 0.14 | 0.02 | 0.02 |
| 3863-5 | 0.00 | 0.00 | 0.25 | 27.71 | 15.98 | 0.45 | 2.68 | 28.97 | 20.24 | 2.49 | 0.60 | 0.46 | 0.03 | 0.10 | 0.03 | 0.03 |
| 3863-5 | 0.00 | 0.00 | 0.20 | 28.26 | 17.16 | 0.32 | 2.23 | 31.84 | 16.72 | 1.68 | 0.74 | 0.68 | 0.03 | 0.13 | 0.01 | 0.01 |
| 3863-5 | 0.00 | 0.00 | 0.16 | 19.06 | 15.20 | 0.51 | 3.02 | 36.54 | 21.29 | 2.76 | 0.92 | 0.38 | 0.02 | 0.10 | 0.01 | 0.01 |
| 3863-5 | 0.00 | 0.00 | 0.03 | 0.29 | 6.06 | 0.37 | 3.26 | 53.48 | 31.80 | 2.74 | 0.78 | 0.88 | 0.05 | 0.18 | 0.04 | 0.03 |
| 3863-5 | 0.00 | 0.00 | 0.26 | 25.74 | 16.20 | 0.51 | 2.92 | 31.55 | 18.82 | 2.53 | 0.86 | 0.46 | 0.03 | 0.09 | 0.02 | 0.01 |
| 3863-5 | 0.00 | 0.00 | 0.19 | 20.65 | 15.48 | 0.38 | 2.76 | 35.90 | 20.56 | 2.54 | 0.78 | 0.61 | 0.06 | 0.06 | 0.01 | 0.02 |
| 3863-5 | 0.00 | 0.00 | 0.19 | 25.88 | 16.67 | 0.31 | 2.38 | 34.81 | 16.50 | 1.90 | 0.72 | 0.54 | 0.04 | 0.03 | 0.02 | 0.02 |
| 3863-5 | 0.00 | 0.00 | 0.20 | 29.58 | 16.88 | 0.31 | 2.01 | 28.68 | 18.97 | 1.82 | 0.62 | 0.69 | 0.03 | 0.17 | 0.01 | 0.02 |
| 3863-5 | 0.00 | 0.00 | 0.07 | 0.76 | 8.04 | 0.69 | 4.85 | 52.50 | 26.95 | 3.82 | 1.21 | 0.84 | 0.02 | 0.19 | 0.04 | 0.03 |
| 3863-5 | 0.00 | 0.00 | 0.14 | 16.17 | 14.15 | 0.57 | 3.81 | 37.23 | 23.14 | 3.08 | 0.98 | 0.53 | 0.03 | 0.09 | 0.02 | 0.04 |
| 3863-5 | 0.00 | 0.00 | 0.30 | 38.75 | 18.50 | 0.27 | 1.71 | 21.34 | 16.39 | 1.57 | 0.64 | 0.44 | 0.03 | 0.04 | 0.02 | 0.01 |

FIGURE 10D

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1581 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:1:

```
GCTCTAATAC  GACTCACTAT  AGGGAAAGCT  GGTACGCCTG  CAGGTACCGG  TCCGGAATTC           60

CCGGGTCGAC  CCACGCGTCC  GCTGAGTTTG  CTGGTTACCA  TTTTCCCTGC  GAACAAAC            118

ATG  GTG  GCT  GCC  GCA  GCA  AGT  GCT  GCA  TTC  TTC  TCC  GTC  GCA  ACC  CCG   166
Met  Val  Ala  Ala  Ala  Ala  Ser  Ala  Ala  Phe  Phe  Ser  Val  Ala  Thr  Pro
 1              5                        10                       15

CGA  ACA  AAC  ATT  TCG  CCA  TCG  AGC  TTG  AGC  GTC  CCC  TTC  AAG  CCC  AAA   214
Arg  Thr  Asn  Ile  Ser  Pro  Ser  Ser  Leu  Ser  Val  Pro  Phe  Lys  Pro  Lys
               20                       25                       30

TCA  AAC  CAC  AAT  GGT  GGC  TTT  CAG  GTT  AAG  GCA  AAC  GCC  AGT  GCC  CAT   262
Ser  Asn  His  Asn  Gly  Gly  Phe  Gln  Val  Lys  Ala  Asn  Ala  Ser  Ala  His
          35                       40                       45

CCT  AAG  GCT  AAC  GGT  TCT  GCA  GTA  AGT  CTA  AAG  TCT  GGC  AGC  CTC  GAG   310
Pro  Lys  Ala  Asn  Gly  Ser  Ala  Val  Ser  Leu  Lys  Ser  Gly  Ser  Leu  Glu
     50                       55                       60

ACT  CAG  GAG  GAC  AAA  ACT  TCA  TCG  TCG  TCC  CCT  CCT  CCT  CGG  ACT  TTC   358
Thr  Gln  Glu  Asp  Lys  Thr  Ser  Ser  Ser  Ser  Pro  Pro  Pro  Arg  Thr  Phe
 65                       70                       75                       80

ATT  AAC  CAG  TTG  CCC  GTC  TGG  AGT  ATG  CTT  CTG  TCT  GCA  GTC  ACG  ACT   406
Ile  Asn  Gln  Leu  Pro  Val  Trp  Ser  Met  Leu  Leu  Ser  Ala  Val  Thr  Thr
                    85                       90                       95

GTC  TTC  GGG  GTG  GCT  GAG  AAG  CAG  TGG  CCA  ATG  CTT  GAC  CGG  AAA  TCT   454
Val  Phe  Gly  Val  Ala  Glu  Lys  Gln  Trp  Pro  Met  Leu  Asp  Arg  Lys  Ser
               100                      105                      110

AAG  AGG  CCC  GAC  ATG  CTT  GTG  GAA  CCG  CTT  GGG  GTT  GAC  AGG  ATT  GTT   502
Lys  Arg  Pro  Asp  Met  Leu  Val  Glu  Pro  Leu  Gly  Val  Asp  Arg  Ile  Val
          115                      120                      125

TAT  GAT  GGG  GTT  AGT  TTC  AGA  CAG  AGT  TTT  TCG  ATT  AGA  TCT  TAC  GAA   550
Tyr  Asp  Gly  Val  Ser  Phe  Arg  Gln  Ser  Phe  Ser  Ile  Arg  Ser  Tyr  Glu
     130                      135                      140

ATA  GGC  GCT  GAT  CGA  ACA  GCC  TCG  ATA  GAG  ACC  CTG  ATG  AAC  ATG  TTC   598
Ile  Gly  Ala  Asp  Arg  Thr  Ala  Ser  Ile  Glu  Thr  Leu  Met  Asn  Met  Phe
145                      150                      155                      160

CAG  GAA  ACA  TCT  CTT  AAT  CAT  TGT  AAG  ATT  ATC  GGT  CTT  CTC  AAT  GAC   646
Gln  Glu  Thr  Ser  Leu  Asn  His  Cys  Lys  Ile  Ile  Gly  Leu  Leu  Asn  Asp
                    165                      170                      175

GGC  TTT  GGT  CGA  ACT  CCT  GAG  ATG  TGT  AAG  AGG  GAC  CTC  ATT  TGG  GTG   694
Gly  Phe  Gly  Arg  Thr  Pro  Glu  Met  Cys  Lys  Arg  Asp  Leu  Ile  Trp  Val
               180                      185                      190

GTC  ACG  AAA  ATG  CAG  ATC  GAG  GTG  AAT  CGC  TAT  CCT  ACT  TGG  GGT  GAT   742
Val  Thr  Lys  Met  Gln  Ile  Glu  Val  Asn  Arg  Tyr  Pro  Thr  Trp  Gly  Asp
          195                      200                      205
```

| | | | | | | | | | | | | | | | | |
|---|---|---|---|---|---|---|---|---|---|---|---|---|---|---|---|---|
| ACT | ATA | GAG | GTC | AAT | ACT | TGG | GTC | TCA | GCG | TCG | GGG | AAA | CAC | GGT | ATG | 790 |
| Thr | Ile | Glu | Val | Asn | Thr | Trp | Val | Ser | Ala | Ser | Gly | Lys | His | Gly | Met | |
| | 210 | | | | 215 | | | | | 220 | | | | | | |
| GGT | CGA | GAT | TGG | CTG | ATA | AGT | GAT | TGC | CAT | ACA | GGA | GAA | ATT | CTT | ATA | 838 |
| Gly | Arg | Asp | Trp | Leu | Ile | Ser | Asp | Cys | His | Thr | Gly | Glu | Ile | Leu | Ile | |
| 225 | | | | | 230 | | | | | 235 | | | | | 240 | |
| AGA | GCA | ACG | AGC | GTG | TGG | GCT | ATG | ATG | AAT | CAA | AAG | ACG | AGA | AGA | TTG | 886 |
| Arg | Ala | Thr | Ser | Val | Trp | Ala | Met | Met | Asn | Gln | Lys | Thr | Arg | Arg | Leu | |
| | | | | 245 | | | | | 250 | | | | | 255 | | |
| TCG | AAA | ATT | CCA | TAT | GAG | GTT | CGA | CAG | GAG | ATA | GAG | CCT | CAG | TTT | GTG | 934 |
| Ser | Lys | Ile | Pro | Tyr | Glu | Val | Arg | Gln | Glu | Ile | Glu | Pro | Gln | Phe | Val | |
| | | | 260 | | | | | 265 | | | | | 270 | | | |
| GAC | TCT | GCT | CCT | GTC | ATT | GTA | GAC | GAT | CGA | AAA | TTT | CAC | AAG | CTT | GAT | 982 |
| Asp | Ser | Ala | Pro | Val | Ile | Val | Asp | Asp | Arg | Lys | Phe | His | Lys | Leu | Asp | |
| | | 275 | | | | | 280 | | | | | 285 | | | | |
| TTG | AAG | ACC | GGT | GAT | TCC | ATT | TGC | AAT | GGT | CTA | ACT | CCA | AGG | TGG | ACT | 1030 |
| Leu | Lys | Thr | Gly | Asp | Ser | Ile | Cys | Asn | Gly | Leu | Thr | Pro | Arg | Trp | Thr | |
| | 290 | | | | | 295 | | | | | 300 | | | | | |
| GAC | TTG | GAT | GTC | AAT | CAG | CAC | GTT | AAC | AAT | GTG | AAA | TAC | ATC | GGG | TGG | 1078 |
| Asp | Leu | Asp | Val | Asn | Gln | His | Val | Asn | Asn | Val | Lys | Tyr | Ile | Gly | Trp | |
| 305 | | | | | 310 | | | | | 315 | | | | | 320 | |
| ATT | CTC | CAG | AGT | GTT | CCC | ACA | GAA | GTT | TTC | GAG | ACG | CAG | GAG | CTA | TGT | 1126 |
| Ile | Leu | Gln | Ser | Val | Pro | Thr | Glu | Val | Phe | Glu | Thr | Gln | Glu | Leu | Cys | |
| | | | | 325 | | | | | 330 | | | | | 335 | | |
| GGC | CTC | ACC | CTT | GAG | TAT | AGG | CGA | GAA | TGC | GGA | AGG | GAC | AGT | GTG | CTG | 1174 |
| Gly | Leu | Thr | Leu | Glu | Tyr | Arg | Arg | Glu | Cys | Gly | Arg | Asp | Ser | Val | Leu | |
| | | | 340 | | | | | 345 | | | | | 350 | | | |
| GAG | TCC | GTG | ACC | GCT | ATG | GAT | CCA | TCA | AAA | GAG | GGA | GAC | CGG | TCT | CTT | 1222 |
| Glu | Ser | Val | Thr | Ala | Met | Asp | Pro | Ser | Lys | Glu | Gly | Asp | Arg | Ser | Leu | |
| | | 355 | | | | | 360 | | | | | 365 | | | | |
| TAC | CAG | CAC | CTT | CTC | CGA | CTC | GAG | GAC | GGG | GCT | GAT | ATC | GTC | AAG | GGG | 1270 |
| Tyr | Gln | His | Leu | Leu | Arg | Leu | Glu | Asp | Gly | Ala | Asp | Ile | Val | Lys | Gly | |
| | 370 | | | | | 375 | | | | | 380 | | | | | |
| AGA | ACC | GAG | TGG | CGG | CCG | AAG | AAT | GCA | GGA | GCC | AAG | GGA | GCA | ATA | TTA | 1318 |
| Arg | Thr | Glu | Trp | Arg | Pro | Lys | Asn | Ala | Gly | Ala | Lys | Gly | Ala | Ile | Leu | |
| 385 | | | | | 390 | | | | | 395 | | | | | 400 | |
| ACC | GGA | AAG | ACC | TCA | AAT | GGA | AAC | TCT | ATA | TCT | TAGAAGGAGG | AAGGGACCTT | 1371 |
| Thr | Gly | Lys | Thr | Ser | Asn | Gly | Asn | Ser | Ile | Ser | | | |
| | | | | 405 | | | | | 410 | | | | |

| | | | | |
|---|---|---|---|---|
| TCCGAGTTGT | GTGTTTATTT | GCTTTGCTTT | GATTCACTCC | ATTGTATAAT | AATACTACGG | 1431 |
| TCAGCCGTCT | TTGTATTTGC | TAAGACAAAT | AGCACAGTCA | TTAAGTAAAA | AAAAAAAAAA | 1491 |
| AAGGGCGGCC | GCTCTAGAGG | ATCCAAGCTT | ACGTACGCGT | GCATGCACG | TCATAGCTCT | 1551 |
| TCTATAGTGT | CACCTAAATT | CAATTCACTG | | | | 1581 |

( 2 ) INFORMATION FOR SEQ ID NO:2:

( i ) SEQUENCE CHARACTERISTICS:
        ( A ) LENGTH: 1360 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:2:

| | | | | | | | | | | | | | | | | |
|---|---|---|---|---|---|---|---|---|---|---|---|---|---|---|---|---|
| CCG | GAT | TGG | AGC | ATG | CTT | CTT | GCA | GCA | ATC | ACA | ACC | ATC | TTC | TTG | GCA | 48 |
| Pro | Asp | Trp | Ser | Met | Leu | Leu | Ala | Ala | Ile | Thr | Thr | Ile | Phe | Leu | Ala | |
| 1 | | | | 5 | | | | | 10 | | | | | 15 | | |
| GCC | GAG | AAG | CAG | TGG | ACG | AAT | CTT | GAC | TGG | AAG | CCC | AGG | AGG | CCT | GAC | 96 |
| Ala | Glu | Lys | Gln | Trp | Thr | Asn | Leu | Asp | Trp | Lys | Pro | Arg | Arg | Pro | Asp | |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 20  |     |     |     | 25  |     |     |     |     |     | 30  |     |     |     |     |
| ATG | CTC | GTC | GAC | TTT | GAC | CCT | TTT | AGT | CTG | GGG | AGG | TTC | GTT | CAG | GAT | 144 |
| Met | Leu | Val | Asp | Phe | Asp | Pro | Phe | Ser | Leu | Gly | Arg | Phe | Val | Gln | Asp |     |
|     |     | 35  |     |     |     | 40  |     |     |     |     |     | 45  |     |     |     |     |
| GGG | TTG | ATT | TTC | AGG | CAG | AAT | TTC | TCC | ATC | AGG | TCT | TAT | GAG | ATT | GGC | 192 |
| Gly | Leu | Ile | Phe | Arg | Gln | Asn | Phe | Ser | Ile | Arg | Ser | Tyr | Glu | Ile | Gly |     |
|     |     | 50  |     |     |     | 55  |     |     |     |     |     | 60  |     |     |     |     |
| GCG | GAT | CGG | ACG | GCA | TCC | ATA | GAG | ACG | TTA | ATG | AAT | CAT | CTA | CAG | GAA | 240 |
| Ala | Asp | Arg | Thr | Ala | Ser | Ile | Glu | Thr | Leu | Met | Asn | His | Leu | Gln | Glu |     |
| 65  |     |     |     |     | 70  |     |     |     |     | 75  |     |     |     |     | 80  |     |
| ACG | GCC | CTA | AAC | CAT | GTA | AGG | TGT | ATA | GGG | CTC | CTC | GAT | GAT | GGT | TTT | 288 |
| Thr | Ala | Leu | Asn | His | Val | Arg | Cys | Ile | Gly | Leu | Leu | Asp | Asp | Gly | Phe |     |
|     |     |     |     | 85  |     |     |     |     | 90  |     |     |     |     | 95  |     |     |
| GGT | TCG | ACG | CCT | GAG | ATG | ACT | AGG | AGA | GAT | CTG | ATA | TGG | GTG | GTT | ACA | 336 |
| Gly | Ser | Thr | Pro | Glu | Met | Thr | Arg | Arg | Asp | Leu | Ile | Trp | Val | Val | Thr |     |
|     |     |     | 100 |     |     |     |     |     | 105 |     |     |     |     |     | 110 |     |
| AGG | ATG | CAG | GTT | CTG | GTG | GAT | CGC | TAT | CCT | TCC | TGG | GGG | GAT | GTC | ATT | 384 |
| Arg | Met | Gln | Val | Leu | Val | Asp | Arg | Tyr | Pro | Ser | Trp | Gly | Asp | Val | Ile |     |
|     |     | 115 |     |     |     |     |     | 120 |     |     |     |     |     | 125 |     |     |
| GAA | GTA | GAC | TCC | TGG | GTT | ACT | CCA | TCT | GGA | AAG | AAT | GGG | ATG | AAA | CGT | 432 |
| Glu | Val | Asp | Ser | Trp | Val | Thr | Pro | Ser | Gly | Lys | Asn | Gly | Met | Lys | Arg |     |
|     | 130 |     |     |     |     |     | 135 |     |     |     |     |     | 140 |     |     |     |
| GAA | TGG | TTT | CTC | CGT | GAT | TGC | AAG | ACA | GGC | GAA | ATC | CTG | ACA | CGA | GCT | 480 |
| Glu | Trp | Phe | Leu | Arg | Asp | Cys | Lys | Thr | Gly | Glu | Ile | Leu | Thr | Arg | Ala |     |
| 145 |     |     |     |     | 150 |     |     |     |     | 155 |     |     |     |     | 160 |     |
| ACC | AGT | GTT | TGG | GTG | ATG | ATG | AAT | AAA | CGG | ACA | CGG | AGG | TTG | TCC | AAA | 528 |
| Thr | Ser | Val | Trp | Val | Met | Met | Asn | Lys | Arg | Thr | Arg | Arg | Leu | Ser | Lys |     |
|     |     |     |     | 165 |     |     |     |     | 170 |     |     |     |     | 175 |     |     |
| ATC | CCT | GAA | GAA | GTT | AGA | GTC | GAA | ATA | GAG | CCT | TAT | TTT | GTG | GAG | CAT | 576 |
| Ile | Pro | Glu | Glu | Val | Arg | Val | Glu | Ile | Glu | Pro | Tyr | Phe | Val | Glu | His |     |
|     |     |     | 180 |     |     |     |     |     | 185 |     |     |     |     |     | 190 |     |
| GGA | GTC | TTG | GAT | GAG | GAC | AGC | AGA | AAA | CTA | CCA | AAG | CTC | AAT | GAC | AAC | 624 |
| Gly | Val | Leu | Asp | Glu | Asp | Ser | Arg | Lys | Leu | Pro | Lys | Leu | Asn | Asp | Asn |     |
|     |     | 195 |     |     |     |     |     | 200 |     |     |     |     |     | 205 |     |     |
| ACT | GCA | AAT | TAC | ATC | AGA | AGA | GGC | CTA | GCT | CCT | CGG | TGG | AGT | GAT | TTA | 672 |
| Thr | Ala | Asn | Tyr | Ile | Arg | Arg | Gly | Leu | Ala | Pro | Arg | Trp | Ser | Asp | Leu |     |
|     | 210 |     |     |     |     |     | 215 |     |     |     |     |     | 220 |     |     |     |
| GAT | GTC | AAT | CAG | CAT | GTG | AAC | AAT | GTC | AAA | TAC | ATT | GGC | TGG | ATT | CTT | 720 |
| Asp | Val | Asn | Gln | His | Val | Asn | Asn | Val | Lys | Tyr | Ile | Gly | Trp | Ile | Leu |     |
| 225 |     |     |     |     | 230 |     |     |     |     | 235 |     |     |     |     | 240 |     |
| GAG | AGC | GTG | CCA | TCT | TCA | CTG | TTG | GAG | AGT | CAT | GAG | CTG | TAT | GGG | ATG | 768 |
| Glu | Ser | Val | Pro | Ser | Ser | Leu | Leu | Glu | Ser | His | Glu | Leu | Tyr | Gly | Met |     |
|     |     |     |     | 245 |     |     |     |     | 250 |     |     |     |     | 255 |     |     |
| ACA | CTT | GAG | TAT | AGG | AAG | GAG | TGT | GGA | AAG | GAC | GGT | TTG | CTG | CAA | TCC | 816 |
| Leu | Glu | Tyr | Arg | Lys | Glu | Cys | Gly | Lys | Asp | Gly | Leu | Leu | Gln | Ser |     |     |
|     |     |     | 260 |     |     |     |     |     | 265 |     |     |     |     | 270 |     |     |
| CTG | ACT | GCT | GTT | GCC | AGT | GAT | TAT | GGG | GGT | GGA | TCC | CTT | GAA | GCT | GGC | 864 |
| Leu | Thr | Ala | Val | Ala | Ser | Asp | Tyr | Gly | Gly | Gly | Ser | Leu | Glu | Ala | Gly |     |
|     |     | 275 |     |     |     |     |     | 280 |     |     |     |     |     | 285 |     |     |
| GTT | GAG | TGT | GAC | CAC | CTT | CTT | CGC | CTT | GAA | GAT | GGG | AGT | GAG | ATT | ATG | 912 |
| Val | Glu | Cys | Asp | His | Leu | Leu | Arg | Leu | Glu | Asp | Gly | Ser | Glu | Ile | Met |     |
|     | 290 |     |     |     |     |     | 295 |     |     |     |     |     | 300 |     |     |     |
| AGG | GGA | AAG | ACG | GAA | TGG | AGG | CCC | AAG | CGT | GCC | GCC | AAC | ACT | ACC | TAC | 960 |
| Arg | Gly | Lys | Thr | Glu | Trp | Arg | Pro | Lys | Arg | Ala | Ala | Asn | Thr | Thr | Tyr |     |
| 305 |     |     |     |     | 310 |     |     |     |     | 315 |     |     |     |     | 320 |     |
| TTT | GGA | AGC | GTT | GAT | GAT | ATT | CCT | CCC | CAC | CCA | ATA | TAT | ATA | TAT | ATA | 1008 |
| Phe | Gly | Ser | Val | Asp | Asp | Ile | Pro | Pro | His | Pro | Ile | Tyr | Ile | Tyr | Ile |     |
|     |     |     |     | 325 |     |     |     |     | 330 |     |     |     |     | 335 |     |     |
| TAT | ATA | TAT | ATA | TAT | ATA | TAT | ATA | TAT | TGG | GTG | GGG | AGC | AGC | TGC | AGC | 1056 |
| Tyr | Ile | Tyr | Ile | Tyr | Ile | Tyr | Ile | Tyr | Trp | Val | Gly | Ser | Ser | Cys | Ser |     |

|   | 340 | | | | 345 | | | | 350 | | |
|---|---|---|---|---|---|---|---|---|---|---|---|
| GGC | AGC | AGC | ACG | ACA | ATG | TCG | AGG | ACA | CGA | TGACGATCAG TATGTTTCGT | 1106 |
| Gly | Ser | Ser | Thr | Thr | Met | Ser | Arg | Thr | Arg | | |
| | | 355 | | | | | 360 | | | | |

GCGGTATTTA GCAATTCCGT ATGTAGAATC CTGCGTGTAC TGGCAGATAA TTTTTTGATT 1166

TGTTCTTTTC GTTACGAGG GGAACCCGTG TAATTAGTTC AACTGTATTT CTGTTTCTT 1226

CCTTAAGTGT TTCAACACCC CTCTCTCTCT CGCGCGCGCG CGTGCGCTCA CATTTTCCAT 1286

TCCTTTTCTT TTTATTCTAG TTGTACGAGT GGGAGTTCAT TTGCACTAAA TTGTTGAAAA 1346

ATCTCGTTGC TTGG 1360

( 2 ) INFORMATION FOR SEQ ID NO:3:

( i ) SEQUENCE CHARACTERISTICS:
        ( A ) LENGTH: 1983 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:3:

GGAGAGCCGC CTCTTCAGCC CACCACCACC TCTAAAACAA CAGGCCCAAA ACTCCCTCCT 60

TTCTCTGTCC CTTTCCGGTG CTTCCCCCTC TATTTTAGAC CTCCTCCTTT ATATTTCCCA 120

ACGTAGAATA ATACCAAAAC CCTAAACCGA GAAGAAGATA AAGAAAGAG GAGAGAGAAA 180

CAGAAAGAGA TAGAGAGAGA AAAAAAATCG GTCTTCTCTC TCTTTCTCTG TCGCTGCGAA 240

GGAGCGGCCG TGAAATTTGG TCATTTGCTA TGAGAAATAT TCCTTCTGTG ATGCTTGATT 300

TCTAATTTAA CGAGTCTGTA TCGTAATTTT CTCATC ATG GTT GCC ACA TCT GCT 354
                                                Met Val Ala Thr Ser Ala
                                                 1               5

| GCC | TCC | GCT | TTC | TTC | CCG | GTT | GCC | TCT | CCG | TCT | CCA | GTG | AAG | CCT | TCG | 402 |
|---|---|---|---|---|---|---|---|---|---|---|---|---|---|---|---|---|
| Ala | Ser | Ala | Phe | Phe | Pro | Val | Ala | Ser | Pro | Ser | Pro | Val | Lys | Pro | Ser | |
| | | | 10 | | | | | 15 | | | | | 20 | | | |

| ATG | ATG | CTC | GGT | GGT | GGA | GGA | GGT | TCG | GAT | AAT | CTC | GAC | GCC | CGT | GGG | 450 |
|---|---|---|---|---|---|---|---|---|---|---|---|---|---|---|---|---|
| Met | Met | Leu | Gly | Gly | Gly | Gly | Gly | Ser | Asp | Asn | Leu | Asp | Ala | Arg | Gly | |
| | | 25 | | | | | 30 | | | | | 35 | | | | |

| ATC | AAA | TCC | CGC | CCT | GCC | TCC | TCT | GGT | GGC | CTT | CAA | GTA | AAG | GCC | AAT | 498 |
|---|---|---|---|---|---|---|---|---|---|---|---|---|---|---|---|---|
| Ile | Lys | Ser | Arg | Pro | Ala | Ser | Ser | Gly | Gly | Leu | Gln | Val | Lys | Ala | Asn | |
| | 40 | | | | | 45 | | | | | 50 | | | | | |

| GCT | CAT | ACT | GTT | CCC | AAG | ATC | AAT | GGT | AAC | AAG | GCG | GGC | CTT | TTG | ACG | 546 |
|---|---|---|---|---|---|---|---|---|---|---|---|---|---|---|---|---|
| Ala | His | Thr | Val | Pro | Lys | Ile | Asn | Gly | Asn | Lys | Ala | Gly | Leu | Leu | Thr | |
| 55 | | | | | 60 | | | | | 65 | | | | | 70 | |

| CCT | ATG | GAG | AGC | ACT | AAG | GAC | GAG | GAC | ATC | GTG | GCT | GCC | CCA | ACG | GTT | 594 |
|---|---|---|---|---|---|---|---|---|---|---|---|---|---|---|---|---|
| Pro | Met | Glu | Ser | Thr | Lys | Asp | Glu | Asp | Ile | Val | Ala | Ala | Pro | Thr | Val | |
| | | | | 75 | | | | | 80 | | | | | 85 | | |

| GCT | CCT | AAG | AGG | ACT | TTC | ATC | AAC | CAG | CTG | CCG | GAT | TGG | AGC | ATG | CTT | 642 |
|---|---|---|---|---|---|---|---|---|---|---|---|---|---|---|---|---|
| Ala | Pro | Lys | Arg | Thr | Phe | Ile | Asn | Gln | Leu | Pro | Asp | Trp | Ser | Met | Leu | |
| | | | 90 | | | | | 95 | | | | | 100 | | | |

| CTT | GCA | GCA | ATC | ACA | ACC | ATC | TTC | TTG | GCA | GCC | GAG | AAG | CAG | TGG | ACG | 690 |
|---|---|---|---|---|---|---|---|---|---|---|---|---|---|---|---|---|
| Leu | Ala | Ala | Ile | Thr | Thr | Ile | Phe | Leu | Ala | Ala | Glu | Lys | Gln | Trp | Thr | |
| | | 105 | | | | | 110 | | | | | 115 | | | | |

| AAT | CTT | GAC | TGG | AAG | CCC | AGG | AGG | CCT | GAC | ATG | CTC | GTC | GAC | TTT | GAC | 738 |
|---|---|---|---|---|---|---|---|---|---|---|---|---|---|---|---|---|
| Asn | Leu | Asp | Trp | Lys | Pro | Arg | Arg | Pro | Asp | Met | Leu | Val | Asp | Phe | Asp | |
| | 120 | | | | | 125 | | | | | 130 | | | | | |

| CCT | TTT | AGT | CTG | GGG | AGG | TTC | GTT | CAG | GAT | GGG | TTG | ATT | TTC | AGG | CAG | 786 |
|---|---|---|---|---|---|---|---|---|---|---|---|---|---|---|---|---|
| Pro | Phe | Ser | Leu | Gly | Arg | Phe | Val | Gln | Asp | Gly | Leu | Ile | Phe | Arg | Gln | |
| 135 | | | | | 140 | | | | | 145 | | | | | 150 | |

AAT TTC TCC ATC AGG TCT TAT GAG ATT GGC GCG GAT CGG ACG GCA TCC    834

```
        Asn  Phe  Ser  Ile  Arg  Ser  Tyr  Glu  Ile  Gly  Ala  Asp  Arg  Thr  Ala  Ser
                       155                 160                           165

ATA  GAG  ACG  TTA  ATG  AAT  CAT  CTA  CAG  GAA  ACG  GCC  CTA  AAC  CAT  GTA    882
        Ile  Glu  Thr  Leu  Met  Asn  His  Leu  Gln  Glu  Thr  Ala  Leu  Asn  His  Val
                       170                 175                           180

AGG  TGT  ATA  GGG  CTC  CTC  GAT  GAT  GGT  TTT  GGT  TCG  ACG  CCT  GAG  ATG    930
        Arg  Cys  Ile  Gly  Leu  Leu  Asp  Asp  Gly  Phe  Gly  Ser  Thr  Pro  Glu  Met
                       185                 190                           195

ACT  AGG  AGA  GAT  CTG  ATA  TGG  GTG  GTT  ACA  AGG  ATG  CAG  GTT  CTG  GTG    978
        Thr  Arg  Arg  Asp  Leu  Ile  Trp  Val  Val  Thr  Arg  Met  Gln  Val  Leu  Val
                       200                 205                           210

GAT  CGC  TAT  CCT  TCC  TGG  GGG  GAT  GTC  ATT  GAA  GTA  GAC  TCC  TGG  GTT   1026
        Asp  Arg  Tyr  Pro  Ser  Trp  Gly  Asp  Val  Ile  Glu  Val  Asp  Ser  Trp  Val
        215                 220                 225                           230

ACT  CCA  TCT  GGA  AAG  AAT  GGG  ATG  AAA  CGT  GAA  TGG  TTT  CTC  CGT  GAT   1074
        Thr  Pro  Ser  Gly  Lys  Asn  Gly  Met  Lys  Arg  Glu  Trp  Phe  Leu  Arg  Asp
                       235                 240                           245

TGC  AAG  ACA  GGC  GAA  ATC  CTG  ACA  CGA  GCT  ACC  AGT  GTT  TGG  GTG  ATG   1122
        Cys  Lys  Thr  Gly  Glu  Ile  Leu  Thr  Arg  Ala  Thr  Ser  Val  Trp  Val  Met
                       250                 255                           260

ATG  AAT  AAA  CGG  ACA  CGG  AGG  TTG  TCC  AAA  ATC  CCT  GAA  GAA  GTT  AGA   1170
        Met  Asn  Lys  Arg  Thr  Arg  Arg  Leu  Ser  Lys  Ile  Pro  Glu  Glu  Val  Arg
                       265                 270                           275

GTC  GAA  ATA  GAG  CCT  TAT  TTT  GTG  GAG  CAT  GGA  GTC  TTG  GAT  GAG  GAC   1218
        Val  Glu  Ile  Glu  Pro  Tyr  Phe  Val  Glu  His  Gly  Val  Leu  Asp  Glu  Asp
                       280                 285                           290

AGC  AGA  AAA  CTA  CCA  AAG  CTC  AAT  GAC  AAC  ACT  GCA  AAT  TAC  ATC  AGA   1266
        Ser  Arg  Lys  Leu  Pro  Lys  Leu  Asn  Asp  Asn  Thr  Ala  Asn  Tyr  Ile  Arg
        295                 300                 305                           310

AGA  GGC  CTA  GCT  CCT  CGG  TGG  AGT  GAT  TTA  GAT  GTC  AAT  CAG  CAT  GTG   1314
        Arg  Gly  Leu  Ala  Pro  Arg  Trp  Ser  Asp  Leu  Asp  Val  Asn  Gln  His  Val
                       315                 320                           325

AAC  AAT  GTC  AAA  TAC  ATT  GGC  TGG  ATT  CTT  GAG  AGC  GTG  CCA  TCT  TCA   1362
        Asn  Asn  Val  Lys  Tyr  Ile  Gly  Trp  Ile  Leu  Glu  Ser  Val  Pro  Ser  Ser
                       330                 335                           340

CTG  TTG  GAG  AGT  CAT  GAG  CTG  TAT  GGG  ATG  ACA  CTT  GAG  TAT  AGG  AAG   1410
        Leu  Leu  Glu  Ser  His  Glu  Leu  Tyr  Gly  Met  Thr  Leu  Glu  Tyr  Arg  Lys
                       345                 350                           355

GAG  TGT  GGA  AAG  GAC  GGT  TTG  CTG  CAA  TCC  CTG  ACT  GCT  GTT  GCC  AGT   1458
        Glu  Cys  Gly  Lys  Asp  Gly  Leu  Leu  Gln  Ser  Leu  Thr  Ala  Val  Ala  Ser
                       360                 365                           370

GAT  TAT  GGG  GGT  GGA  TCC  CTT  GAA  GCT  GGC  GTT  GAG  TGT  GAC  CAC  CTT   1506
        Asp  Tyr  Gly  Gly  Gly  Ser  Leu  Glu  Ala  Gly  Val  Glu  Cys  Asp  His  Leu
        375                 380                 385                           390

CTT  CGC  CTT  GAA  GAT  GGG  AGT  GAG  ATT  ATG  AGG  GGA  AAG  ACG  GAA  TGG   1554
        Leu  Arg  Leu  Glu  Asp  Gly  Ser  Glu  Ile  Met  Arg  Gly  Lys  Thr  Glu  Trp
                       395                 400                           405

AGG  CCC  AAG  CGT  GCC  GCC  AAC  ACT  ACC  TAC  TTT  GGA  AGC  GTT  GAT  GAT   1602
        Arg  Pro  Lys  Arg  Ala  Ala  Asn  Thr  Thr  Tyr  Phe  Gly  Ser  Val  Asp  Asp
                       410                 415                           420

ATT  CCT  CCA  GCA  AAT  AAT  GCA  TAGCCAAAAT  GTATATATAT  ATATATATAT            1653
        Ile  Pro  Pro  Ala  Asn  Asn  Ala
                       425

ATATATATAT  ATATATATAT  ATATATATAT  ATTGGGTGGG  GAGCAGCTGC  AGCGGCAGCA           1713

GCACGACAAT  GTCGAGGACA  CGATGACGAT  CAGTATGTTT  CGTGCGGTAT  TTAGCAATTC           1773

CGTATGTAGA  ATCCTGCGTG  TACTGGCAGA  TAATTTTTTG  ATTTGTTCTT  TTCGTTTACG           1833

AGGGGAACCC  GTGTAATTAG  TTCAACTGTA  TTTTCTGTTT  CTTCCTTAAG  TGTTTCAACA           1893

CCCCTCTCTC  TCTCGCGCGC  GCGCGTGCGC  TCACATTTTC  CATTCCTTTT  CTTTTTATTC           1953
```

```
TAGTTGTACG AGTGGGAGTT CATTTGCACT                                                      1983
```

( 2 ) INFORMATION FOR SEQ ID NO:4:

( i ) SEQUENCE CHARACTERISTICS:
        ( A ) LENGTH: 1157 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:4:

```
T   CTA  GAG  TGG  AAG  CCG  AAG  CCG  AAT  CCA  CCC  CAG  TTG  CTT  GAT  GAC  CAT       49
    Leu  Glu  Trp  Lys  Pro  Lys  Pro  Asn  Pro  Pro  Gln  Leu  Leu  Asp  Asp  His
    1              5                        10                       15

TTT  GGG  CCG  CAT  GGG  TTA  GTT  TTC  AGG  CGC  ACC  TTT  GCC  ATC  AGA  TCG           97
Phe  Gly  Pro  His  Gly  Leu  Val  Phe  Arg  Arg  Thr  Phe  Ala  Ile  Arg  Ser
                   20                      25                      30

TAT  GAG  GTG  GGA  CCT  GAC  CGC  TCC  ACA  TCT  ATA  GTG  GCT  GTT  ATG  AAT          145
Tyr  Glu  Val  Gly  Pro  Asp  Arg  Ser  Thr  Ser  Ile  Val  Ala  Val  Met  Asn
               35                      40                      45

CAC  TTG  CAG  GAG  GCT  GCA  CTT  AAT  CAT  GCG  AAG  AGT  GTG  GGA  ATT  CTA          193
His  Leu  Gln  Glu  Ala  Ala  Leu  Asn  His  Ala  Lys  Ser  Val  Gly  Ile  Leu
          50                      55                      60

GGA  GAT  GGA  TTC  GGT  ACG  ACG  CTA  GAG  ATG  AGT  AAG  AGA  GAT  CTG  ATA          241
Gly  Asp  Gly  Phe  Gly  Thr  Thr  Leu  Glu  Met  Ser  Lys  Arg  Asp  Leu  Ile
65                      70                      75                      80

TGG  GTT  GTG  AAA  CGC  ACG  CAT  GTT  GCT  GTG  GAA  CGG  TAC  CCT  GCT  TGG          289
Trp  Val  Val  Lys  Arg  Thr  His  Val  Ala  Val  Glu  Arg  Tyr  Pro  Ala  Trp
                    85                      90                      95

GGT  GAT  ACT  GTT  GAA  GTA  GAG  TGC  TGG  GTT  GGT  GCA  TCG  GGA  AAT  AAT          337
Gly  Asp  Thr  Val  Glu  Val  Glu  Cys  Trp  Val  Gly  Ala  Ser  Gly  Asn  Asn
               100                     105                     110

GGC  AGG  CGC  CAT  GAT  TTC  CTT  GTC  CGG  GAC  TGC  AAA  ACA  GGC  GAA  ATT          385
Gly  Arg  Arg  His  Asp  Phe  Leu  Val  Arg  Asp  Cys  Lys  Thr  Gly  Glu  Ile
          115                     120                     125

CTT  ACA  AGA  TGT  ACC  AGT  CTT  TCG  GTG  ATG  ATG  AAT  ACA  AGG  ACA  AGG          433
Leu  Thr  Arg  Cys  Thr  Ser  Leu  Ser  Val  Met  Met  Asn  Thr  Arg  Thr  Arg
     130                     135                     140

AGG  TTG  TCC  AAA  ATC  CCT  GAA  GAA  GTT  AGA  GGG  GAG  ATA  GGG  CCT  GCA          481
Arg  Leu  Ser  Lys  Ile  Pro  Glu  Glu  Val  Arg  Gly  Glu  Ile  Gly  Pro  Ala
145                     150                     155                     160

TTC  ATT  GAT  AAT  GTG  GCT  GTC  AAA  GAC  GAG  GAA  ATT  AAG  AAA  CCA  CAG          529
Phe  Ile  Asp  Asn  Val  Ala  Val  Lys  Asp  Glu  Glu  Ile  Lys  Lys  Pro  Gln
               165                     170                     175

AAG  CTC  AAT  GAC  AGC  ACT  GCA  GAT  TAC  ATC  CAA  GGA  GGA  TTG  ACT  CCT          577
Lys  Leu  Asn  Asp  Ser  Thr  Ala  Asp  Tyr  Ile  Gln  Gly  Gly  Leu  Thr  Pro
          180                     185                     190

CGA  TGG  AAT  GAT  TTG  GAT  ATC  AAT  CAG  CAC  GTT  AAC  AAC  ATC  AAA  TAC          625
Arg  Trp  Asn  Asp  Leu  Asp  Ile  Asn  Gln  His  Val  Asn  Asn  Ile  Lys  Tyr
     195                     200                     205

GTT  GAC  TGG  ATT  CTT  GAG  ACT  GTC  CCA  GAC  TCA  ATC  TTT  GAG  AGT  CAT          673
Val  Asp  Trp  Ile  Leu  Glu  Thr  Val  Pro  Asp  Ser  Ile  Phe  Glu  Ser  His
          210                     215                     220

CAT  ATT  TCC  AGC  TTC  ACT  ATT  GAA  TAC  AGG  AGA  GAG  TGC  ACG  AGG  GAT          721
His  Ile  Ser  Ser  Phe  Thr  Ile  Glu  Tyr  Arg  Arg  Glu  Cys  Thr  Arg  Asp
225                     230                     235                     240

AGC  GTG  CTG  CAG  TCC  CTG  ACC  ACT  GTC  TCC  GGT  GGC  TCG  TCG  GAA  GCT          769
Ser  Val  Leu  Gln  Ser  Leu  Thr  Thr  Val  Ser  Gly  Gly  Ser  Ser  Glu  Ala
               245                     250                     255
```

| | | | | | | | | | | | | | | | | |
|---|---|---|---|---|---|---|---|---|---|---|---|---|---|---|---|---|
| GGG | TTA | GTG | TGC | GAG | CAC | TTG | CTC | CAG | CTT | GAA | GGT | GGG | TCT | GAG | GTA | 817 |
| Gly | Leu | Val | Cys<br>260 | Glu | His | Leu | Leu | Gln<br>265 | Leu | Glu | Gly | Gly | Ser<br>270 | Glu | Val | |
| TTG | AGG | GCA | AAA | ACA | GAG | TGG | AGG | CCT | AAG | CTT | ACC | GAT | AGT | TTC | AGA | 865 |
| Leu | Arg | Ala<br>275 | Lys | Thr | Glu | Trp | Arg<br>280 | Pro | Lys | Leu | Thr | Asp<br>285 | Ser | Phe | Arg | |
| GGG | ATT | AGT | GTG | ATA | CCC | GCA | GAA | TCG | AGT | GTC | TAACTAACGA | | AAGAAGCATC | | | 918 |
| Gly<br>290 | Ile | Ser | Val | Ile | Pro<br>295 | Ala | Glu | Ser | Ser | Val | | | | | | |

TGATGAAGTT TCTCCTGTGC TGTTGTTCGT GAGGATGCTT TTTAGAAGCT GCAGTTTGCA 978

TTGCTTGTGC AGAATCATGG CCTGTGGTTT TAGATATATA TTCAAAATTG TCCTATAGTC 1038

AAGAAACTTA ATATCAGAAA AATAACTCAA TGAGTCAAGG TTATCGAAGT AGTCATGTAA 1098

GCTTTGAAAT ATGTTGTGTA TTCCTCGGCT TTATGTAATC TGTAAGCTCT TTCTCTTGC 1157

( 2 ) INFORMATION FOR SEQ ID NO:5:

( i ) SEQUENCE CHARACTERISTICS:
        ( A ) LENGTH: 1433 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:5:

| | | | | | | | | | | | | | | | | |
|---|---|---|---|---|---|---|---|---|---|---|---|---|---|---|---|---|
| GAA | TTC | GGC | ACG | AGG | GGC | TCC | GGT | GCT | TTG | CAG | GTG | AAG | GCA | AGT | TCC | 48 |
| Glu | Phe | Gly | Thr | Arg<br>5 | Gly | Ser | Gly | Ala | Leu<br>10 | Gln | Val | Lys | Ala | Ser<br>15 | Ser | |
| CAA | GCT | CCA | CCA | AAG | CTC | AAT | GGT | TCC | AAT | GTG | GGT | TTG | GTT | AAA | TCT | 96 |
| Gln | Ala | Pro<br>20 | Pro | Lys | Leu | Asn | Gly<br>25 | Ser | Asn | Val | Gly | Leu<br>30 | Val | Lys | Ser | |
| AGC | CAA | ATT | GTG | AAG | AAG | GGT | GAT | GAC | ACC | ACA | TCT | CCT | CCT | GCA | AGA | 144 |
| Ser | Gln | Ile<br>35 | Val | Lys | Lys | Gly | Asp<br>40 | Asp | Thr | Thr | Ser | Pro<br>45 | Pro | Ala | Arg | |
| ACT | TTC | ATC | AAC | CAA | TTG | CCT | GAT | TGG | AGC | ATG | CTT | CTT | GCT | GCT | ATC | 192 |
| Thr | Phe<br>50 | Ile | Asn | Gln | Leu | Pro<br>55 | Asp | Trp | Ser | Met | Leu<br>60 | Leu | Ala | Ala | Ile | |
| ACA | ACC | CTG | TTC | TTG | GCT | GCA | GAG | AAG | CAG | TGG | ATG | ATG | CTT | GAT | TGG | 240 |
| Thr<br>65 | Thr | Leu | Phe | Leu | Ala<br>70 | Ala | Glu | Lys | Gln | Trp<br>75 | Met | Met | Leu | Asp | Trp<br>80 | |
| AAA | CCC | AAA | AGG | CCT | GAC | ATG | CTT | GTT | GAT | CCA | TTT | GGT | CTT | GGA | AGG | 288 |
| Lys | Pro | Lys | Arg | Pro<br>85 | Asp | Met | Leu | Val | Asp<br>90 | Pro | Phe | Gly | Leu | Gly<br>95 | Arg | |
| TTT | GTT | CAG | GAT | GGT | CTT | GTT | TTC | CGC | AAC | AAC | TTT | TCA | ATT | CGA | TCA | 336 |
| Phe | Val | Gln | Asp<br>100 | Gly | Leu | Val | Phe | Arg<br>105 | Asn | Asn | Phe | Ser | Ile<br>110 | Arg | Ser | |
| TAT | GAA | ATA | GGG | GCT | GAT | CGA | ACG | GCT | TCT | ATA | GAA | ACG | TTA | ATG | AAT | 384 |
| Tyr | Glu | Ile<br>115 | Gly | Ala | Asp | Arg | Thr<br>120 | Ala | Ser | Ile | Glu | Thr<br>125 | Leu | Met | Asn | |
| CAT | CTG | CAG | GAA | ACA | GCT | CTT | AAT | CAT | GTG | AAG | TCT | GTT | GGG | CTT | CTT | 432 |
| His | Leu<br>130 | Gln | Glu | Thr | Ala | Leu<br>135 | Asn | His | Val | Lys | Ser<br>140 | Val | Gly | Leu | Leu | |
| GAG | GAT | GGC | CTA | GGT | TCG | ACT | CGA | GAG | ATG | TCC | TTG | AGG | AAC | CTG | ATA | 480 |
| Glu | Asp<br>145 | Gly | Leu | Gly | Ser<br>150 | Thr | Arg | Glu | Met | Ser<br>155 | Leu | Arg | Asn | Leu | Ile<br>160 | |
| TGG | GTT | GTC | ACT | AAA | ATG | CAG | GTT | GCG | GTT | GAT | CGC | TAT | CCA | ACT | TGG | 528 |
| Trp | Val | Val | Thr | Lys<br>165 | Met | Gln | Val | Ala | Val<br>170 | Asp | Arg | Tyr | Pro | Thr<br>175 | Trp | |
| GGA | GAT | GAA | GTT | CAG | GTA | TCC | TCT | TGG | GCT | ACT | GCA | ATT | GGA | AAG | AAT | 576 |
| Gly | Asp | Glu | Val<br>180 | Gln | Val | Ser | Ser | Trp<br>185 | Ala | Thr | Ala | Ile | Gly<br>190 | Lys | Asn | |

```
GGA ATG CGT CGC GAA TGG ATA GTC ACT GAT TTT AGA ACT GGT GAA ACT        624
Gly Met Arg Arg Glu Trp Ile Val Thr Asp Phe Arg Thr Gly Glu Thr
    195                 200                 205

CTA TTA AGA GCC ACC AGT GTT TGG GTG ATG ATG AAT AAA CTG ACG AGG        672
Leu Leu Arg Ala Thr Ser Val Trp Val Met Met Asn Lys Leu Thr Arg
210                 215                 220

AGG ATA TCC AAA ATC CCA GAA GAG GTT TGG CAC GAA ATA GGC CCC TCT        720
Arg Ile Ser Lys Ile Pro Glu Glu Val Trp His Glu Ile Gly Pro Ser
225                 230                 235                 240

TTC ATT GAT GCT CCT CCT CTT CCC ACC GTG GAA GAT GAT GGT AGA AAG        768
Phe Ile Asp Ala Pro Pro Leu Pro Thr Val Glu Asp Asp Gly Arg Lys
                245                 250                 255

CTG ACA AGG TTT GAT GAA AGT TCT GCA GAC TTT ATC CGC NCT GGT TTA        816
Leu Thr Arg Phe Asp Glu Ser Ser Ala Asp Phe Ile Arg Xxx Gly Leu
                260                 265                 270

ACT CCT AGG TGG AGT GAT TTG GAC ATC AAC CAG CAT GTC AAC AAT GTG        864
Thr Pro Arg Trp Ser Asp Leu Asp Ile Asn Gln His Val Asn Asn Val
            275                 280                 285

AAG TAC ATT GGC TGG CTC CTT GAG AGT GCT CCG CCG GAG ATC CAC GAG        912
Lys Tyr Ile Gly Trp Leu Leu Glu Ser Ala Pro Pro Glu Ile His Glu
        290                 295                 300

AGT CAC GAG ATA GCG TCT CTG ACT CTG GAG TAC AGG AGG GAG TGT GGA        960
Ser His Glu Ile Ala Ser Leu Thr Leu Glu Tyr Arg Arg Glu Cys Gly
305                 310                 315                 320

AGG GAC AGC GTG CTG AAC TCC GCG ACC AAG GTC TCT GAC TCC TCT CAA       1008
Arg Asp Ser Val Leu Asn Ser Ala Thr Lys Val Ser Asp Ser Ser Gln
                325                 330                 335

CTG GGA AAG TCT GCT GTG GAG TGT AAC CAC TTG GTT CGT CTC CAG AAT       1056
Leu Gly Lys Ser Ala Val Glu Cys Asn His Leu Val Arg Leu Gln Asn
                340                 345                 350

GGT GGG GAG ATT GTG AAG GGA AGG ACT GTG TGG AGG CCC AAA CGT CCT       1104
Gly Gly Glu Ile Val Lys Gly Arg Thr Val Trp Arg Pro Lys Arg Pro
            355                 360                 365

CTT TAC AAT GAT GGT GCT GTT GTG GAC GTG NAA GCT AAA ACC TCT           1149
Leu Tyr Asn Asp Gly Ala Val Val Asp Val Xxx Ala Lys Thr Ser
        370                 375                 380

TAAGTCTTAT AGTCCAAGTG AGGAGGAGTT CTATGTATCA GGAAGTTGCT AGGATTCTCA     1209

ATCGCATGTG TCCATTTCTT GTGTGGAATA CTGCTCGTGT TCTAGACTC GCTATATGTT      1269

TGTTCTTTTA TATATATATA TATATATATA TCTCTCTCTT CCCCCCACCT CTCTCTCTCT     1329

CTCTATATAT ATATATGTTT TATGTAAGTT TTCCCCTTAG TTTCCTTTCC TAAGTAATGC     1389

CATTGTAAAT TACTTCAAAA AAAAAAAAAA AAAAAAACT CGAG                       1433
```

( 2 ) INFORMATION FOR SEQ ID NO:6:

( i ) SEQUENCE CHARACTERISTICS:
        ( A ) LENGTH: 976 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:6:

```
GGCACGAGAA ACATGGTGGC TGCCGCAGCA AGTTCTGCAT TCTTCTCCGT TCCAACCCCG      60

GGAATCTCCC CTAAACCCGG GAAGTTCGGT AATGGTGGCT TTCAGGTTAA GGCAAACGCC     120

AATGCCCATC CTAGTCTAAA GTCTGGCAGC CTCGAGACTG AAGATGACAC TTCATCGTCG     180

TCCCCTCCTC CTCGGACTTT CATTAACCAG TTGCCCGACT GGAGTATGCT TCTGTCCGCA     240
```

| | | | | | | |
|---|---|---|---|---|---|---|
| ATCACGACTA | TCTTCGGGGC | AGCTGAGAAG | CAGTGGATGA | TGCTTGATAG | GAAATCTAAG | 300 |
| NAGACCCGAC | ATGCTCATGG | CAACCGTTTG | GGGTTGACAG | TATTGTTCAG | GATGGGGTTT | 360 |
| TTTTCAGACA | GAGTTTTTCG | ATTAGATCTT | ACGAAATAGG | CGCTGATCGA | ACAACCTCAA | 420 |
| TAGAGACGCT | GATGAACATG | TTCCAGGAAA | CGTCTTTGAA | TCATTGTAAG | AGTAACGGTC | 480 |
| TTCTCAATGA | CGGCTTTGGT | CGCACTCCTG | AGATGTGTAA | GAAGGGCCTC | ATTTGGGTGG | 540 |
| TTACGAAAAT | GCAGGTCGAG | GTGAATCGCT | ATCCTATTTG | GSGTGATTCT | ATCGAAGTCA | 600 |
| ATACTTGGGT | CTCCGAGTCG | GGGNAAAANC | GGTATGGGTC | GTGATTGGCT | GATAAGTGAT | 660 |
| TGCAGTACAG | GAGNAAATTC | TTGTAAGAGC | AACGAGCGTG | TGGGCTATGA | TGAATCAAAA | 720 |
| GACGAGAAGA | TTGTCAAAAT | TTCCATTTGA | GGTTCGACAA | GAGATAGCGC | CTAATTTTGT | 780 |
| CGACTCTGTT | CCTGTCATTG | AAGACGATCG | AAAATTACAC | AAGCTTGATG | TGAAGACGGG | 840 |
| TGATTCCATT | CACAATGGTC | TAACTCCAAG | GTGGAATGAC | TTGGATGTCA | ATCAGCACGT | 900 |
| TAACAATGTG | AAATACATTG | GGTGGATTCT | CAAGAGTGTT | CCAACAGATG | TTTTGGGGC | 960 |
| CCAGGAGCTA | TGTGGA | | | | | 976 |

( 2 ) INFORMATION FOR SEQ ID NO:7:

( i ) SEQUENCE CHARACTERISTICS:
        ( A ) LENGTH: 1647 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:7:

| | | | | | | |
|---|---|---|---|---|---|---|
| GGCGCGCCGG | TACCTCTAGA | CCTGGCGATT | CAACGTGGTC | GGATCATGAC | GCTTCCAGAA | 60 |
| AACATCGAGC | AAGCTCTCAA | AGCTGACCTC | TTTCGGATCG | TACTGAACCC | GAACAATCTC | 120 |
| GTTATGTCCC | GTCGTCTCCG | AACAGACATC | CTCGTAGCTC | GGATTATCGA | CGAATCCATG | 180 |
| GCTATACCCA | ACCTCCGTCT | TCGTCACGCC | TGGAACCCTC | TGGTACGCCA | ATTCCGCTCC | 240 |
| CCAGAAGCAA | CCGGCGCCGA | ATTGCGCGAA | TTGCTGACCT | GGAGACGGAA | CATCGTCGTC | 300 |
| GGGTCCTTGC | GCGATTGCGG | CGGAAGCCGG | GTCGGGTTGG | GGACGAGACC | CGAATCCGAG | 360 |
| CCTGGTGAAG | AGGTTGTTCA | TCGGAGATTT | ATAGACGGAG | ATGGATCGAG | CGGTTTTGGG | 420 |
| GAAAGGGGAA | GTGGGTTTGG | CTCTTTTGGA | TAGAGAGAGT | GCAGCTTTGG | AGAGAGACTG | 480 |
| GAGAGGTTTA | GAGAGAGACG | CGGCGGATAT | TACCGGAGGA | GAGGCGACGA | GAGATAGCAT | 540 |
| TATCGAAGGG | GAGGGAGAAA | GAGTGACGTG | GAGAAATAAG | AAACCGTTAA | GAGTCGGATA | 600 |
| TTTATCATAT | TAAAAGCCCA | ATGGGCCTGA | ACCCATTTAA | ACAAGACAGA | TAAATGGGCC | 660 |
| GTGTGTTAAG | TTAACAGAGT | GTTAACGTTC | GGTTTCAAAT | GCCAACGCCA | TAGGAACAAA | 720 |
| ACAAACGTGT | CCTCAAGTAA | ACCCCTGCCG | TTTACACCTC | AATGGCTGCA | TGGTGAAGCC | 780 |
| ATTAACACGT | GGCGTAGGAT | GCATGACGAC | GCCATTGACA | CCTGACTCTC | TTCCCTTCTC | 840 |
| TTCATATATC | TCTAATCAAT | TCAACTACTC | ATTGTCATAG | CTATTCGGAA | AATACATACA | 900 |
| CATCCTTTTC | TCTTCGATCT | CTCTCAATTC | ACAAGAAGCA | AAGTCGACGG | ATCCCTGCAG | 960 |
| TAAATTACGC | CATGACTATT | TTCATAGTCC | AATAAGGCTG | ATGTCGGGAG | TCCAGTTTAT | 1020 |
| GAGCAATAAG | GTGTTTAGAA | TTTGATCAAT | GTTTATAATA | AAGGGGGAA | GATGATATCA | 1080 |
| CAGTCTTTTG | TTCTTTTTGG | CTTTTGTTAA | ATTTGTGTGT | TTCTATTTGT | AAACCTCCTG | 1140 |
| TATATGTTGT | ACTTCTTTCC | CTTTTTAAGT | GGTATCGTCT | ATATGGTAAA | ACGTTATGTT | 1200 |
| TGGTCTTTCC | TTTTCTCTGT | TTAGGATAAA | AAGACTGCAT | GTTTTATCTT | TAGTTATATT | 1260 |

```
ATGTTGAGTA  AATGAACTTT  CATAGATCTG  GTTCCGTAGA  GTAGACTAGC  AGCCGAGCTG   1320

AGCTGAACTG  AACAGCTGGC  AATGTGAACA  CTGGATGCAA  GATCAGATGT  GAAGATCTCT   1380

AATATGGTGG  TGGGATTGAA  CATATCGTGT  CTATATTTTT  GTTGGCATTA  AGCTCTTAAC   1440

ATAGATATAA  CTGATGCAGT  CATTGGTTCA  TACACATATA  TAGTAAGGAA  TTACAATGGC   1500

AACCCAAACT  TCAAAAACAG  TAGGCCACCT  GAATTGCCTT  ATCGAATAAG  AGTTTGTTTC   1560

CCCCCACTTC  ATGGGATGTA  ATACATGGGA  TTTGGGAGTT  TGAATGAACG  TTGAGACATG   1620

GCAGAACCTC  TAGAGGTACC  GGCGCGC                                         1647
```

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO:8:

```
CUACUACUAC  UAUCGAUACC  AUCUUUUCGG  CUGCUGA                              37
```

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO:9:

```
CAUCAUCAUC  AUGAGCUCGC  AAGAGAAAGA  GCUUACAG                             38
```

( 2 ) INFORMATION FOR SEQ ID NO:10:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO:10:

```
CUACUACUAC  UAGAAUUCGC  AUGCAGGCCU  AUGCUUGACC  GGAAAUCU                 48
```

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO:11:

```
GTTTTCCCAG  TCACGAC                                                     17
```

( 2 ) INFORMATION FOR SEQ ID NO:12:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: synthetic oligonucleotide ( x i ) SEQUENCE DESCRIPTION: SEQ ID NO:12:

CAUCAUCAUC AUGTCGACAA ACATGGTGGC TGCCGCAG                                          38

( 2 ) INFORMATION FOR SEQ ID NO:13:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: synthetic oligonucleotide ( x i ) SEQUENCE DESCRIPTION: SEQ ID NO:13:

CUACUACUAC UAATGCATTA CTAAGATATA GAGTTTCCAT TTG                                    43

( 2 ) INFORMATION FOR SEQ ID NO:14:

( i ) SEQUENCE CHARACTERISTICS:
    ( A ) LENGTH: 100 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: synthetic oligonucleotide ( x i ) SEQUENCE DESCRIPTION: SEQ ID NO:14:

CGGTCTAGAT AACAATCAAT GCAAGACTAT TGCACACGTG TTGCGTGTGA ACAATGGTCA                  60

GGAGCTTCAC GTCTGGGAAA CGCCCCCAAA AGAAAACGTG                                        100

( 2 ) INFORMATION FOR SEQ ID NO:15:

( i ) SEQUENCE CHARACTERISTICS:
    ( A ) LENGTH: 100 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: synthetic oligonucleotide ( x i ) SEQUENCE DESCRIPTION: SEQ ID NO:15:

ATACTCGGCC AATCCAGCGA AGTGGTCCAT TCTTCTGGCG AAACCAGAAG CAATCAAAAT                  60

GGTGTTGTTT TTAAAAGGCA CGTTTTCTTT TGGGGGCGTT                                        100

( 2 ) INFORMATION FOR SEQ ID NO:16:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: synthetic oligonucleotide ( x i ) SEQUENCE DESCRIPTION: SEQ ID NO:16:

```
CAUCAUCAUC AUGGATCCCT CATCATGGTT GCCACATCTG C                                    4 1
```

( 2 ) INFORMATION FOR SEQ ID NO:17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO:17:

```
CUACUACUAC UACUCGAGTT ACATTTTGGC TATGC                                           3 5
```

PRODUCTION OF MYRISTATE IN PLANT CELLS

This application is a continuation-in-part of U.S. Ser. No. 08/383,756 filed Feb. 2, 1995, issued as U.S. Pat. No. 5,654,495, and a continuation-in-part of U.S. Ser. No. 07/968,971 filed Oct. 30, 1992, issued as U.S. Pat. No. 5,455,167, and a continuation-in-part of PCT/US93/10814 filed Oct. 29, 1993, and a continuation-in-part of U.S. Ser. No. 08/261,695, filed Jun. 16, 1994 now abandoned.

TECHNICAL FIELD OF THE INVENTION

The present invention is directed to nucleic acid sequences and constructs, and methods related thereto.

INTRODUCTION

BACKGROUND OF THE INVENTION

Members of several plant families synthesize large amounts of predominantly medium-chain (C8–C14) triglycerides in specialized storage tissues, some of which are harvested for production of important dietary or industrial medium-chain fatty acids containing oils (F. D. Gunstone, *The Lipid Handbook* (Chapman & Hall, New York, 1986) pp. 55–112). Lauric oil (those containing C12:0 fatty acyl groups) and its derivatives find widespread use, particularly in the soap, detergent and personal care industries.

Over the past several years, mildness has become increasingly important in differentiating soaps, detergents and personal care products, with an emphasis on developing surfactants that combine acceptable performance with improved mildness. Myristate (C14:0) based surfactants offer an excellent combination of cleansing and mildness. However, limitations on the supply of myristate have precluded significant use of these surfactants, despite their functional superiority in certain applications. Myristate is available only in relatively small quantities as a coproduct of the fractionation of lauric oils. Coconut oil contains approximately 48% C12:0 and 17% C14:0, and palm kernel oil contains approximately 51% C12:0 and 18% C14:0. Only a fraction of the C14:0 present in these oils, however, is available as purified C14:0 (myristate), as most commercial "lauric fatty acid/methyl ester" products contain significant amounts of myristate, in addition to the primary laurate component. Thus, myristate based derivatives currently find only limited use in the personal care product industry due to the high cost involved in their production.

LITERATURE

Pollard, et al., (*Arch. of Biochem. and Biophys.* (1991) 284:1–7) identified a medium-chain acyl-ACP thioesterase activity in developing oilseeds of California bay, *Umbellularia californica*. The bay thioesterase was subsequently purified by Davies et al., (*Arch. Biochem. Biophys.* (1991) 290:37–45) which allowed the cloning of a corresponding cDNA which has been used to modify the triglyceride composition of plants(WO 91/16421 and WO 92/20236).

BRIEF DESCRIPTION OF THE FIGURES

FIGS. 1A–1E. The nucleic acid sequence and translated amino acid sequence of *Cuphea palustris* C14:0-ACP thioesterase cDNA clone (SEQ ID NO:1) MCT34 (CpFatB2) are provided.

FIGS. 2A–2E. The nucleic acid sequence and translated amino acid sequence of a nutmeg (*Myristica fragrans*) Class II type thioesterase, MYRF-1 (MfFatB2) (SEQ ID NO:2), having preferential activity on C14:0-ACP is provided.

FIGS. 3A–3E. The nucleic acid sequence and translated amino acid sequence of a nutmeg (*Myristica fragrans*) Class II type thioesterase, MYRF-2 (MfFatB1) (SEQ ID NO:3), having preferential activity on C14:0-ACP is provided.

FIGS. 4A–4C. Nucleic acid and translated amino acid sequence (SEQ ID NO:4) of a PCR fragment containing the encoding region for the mature protein portion of a camphor Class II acyl-ACP thioesterase is provided.

FIGS. 5A–5D. The nucleic acid sequence and translated amino acid sequence of an elm acyl-ACP thioesterase partial cDNA clone (SEQ ID NO:5) are provided.

FIGS. 6A–6B. The nucleic acid sequence of a *Cuphea hookeriana* CUPH-4 thioesterase cDNA clone (SEQ ID NO:6), CMT13, is provided.

FIGS. 7A–7C. Nucleic acid sequence (SEQ ID NO:7) of an oleosin expression cassette is provided.

FIG. 8. Mole % fatty acid composition data from single seeds of Brassica plants 3854-3 and 3854-11, expressing a nutmeg FatB thioesterase, are provided.

FIG. 9A–9B. Mole % fatty acid composition data from single seeds of Brassica plants 5233-5 (FIG. 9A) and 5233-6 (FIG. 9B), expressing a camphor FatB thioesterase, are provided.

FIG. 10A–10C. Mole % fatty acid composition data from single seeds of Brassica plants 3863-10, 3863-7, 3863-4, 3863-8, 3863-2 and 3863-5 expressing a *C. palustris* FatB thioesterase, are provided.

SUMMARY OF THE INVENTION

By this invention, plant genes encoding acyl-ACP thioesterases having the ability to act on C14:0-ACP substrate to form free C14:0 (myristate) are provided. The invention encompasses sequences which encode biologically active thioesterases from plants or bacteria, as well as sequences which are to be used as probes, vectors for transformation or cloning intermediates. Biologically active sequences are preferentially found in a sense orientation with respect to transcriptional regulatory regions found in various constructs. The instant invention pertains to the entire or portions of the genomic sequence or cDNA sequence and to the thioesterase protein encoded thereby, including precursor or mature plant thioesterases.

Various plant genes encoding thioesterases having the ability to hydrolyze C14:0-ACP substrate are exemplified herein, and may be obtained for example from Cuphea species, nutmeg, camphor and elm. The exemplified plant thioesterase sequences may also be used to obtain other related plant thioesterase genes.

Other sources of genes which encode proteins capable of hydrolyzing C14 acyl-ACP substrates are also considered herein, and in particular, C14 acyl-ACP thioesterase activity of a luxD gene obtainable from bioluminescent bacteria is demonstrated. Constructs and methods for producing C14:0 in host cells using a luxD gene from *Vibrio harbeyi* are provided herein.

Of special interest are recombinant DNA constructs which can provide for the transcription or transcription and translation (expression) of the disclosed protein sequences. In particular, constructs which are capable of transcription or transcription and translation in plant host cells are preferred. Such construct may contain a variety of regulatory regions including transcriptional initiation regions obtained from genes preferentially expressed in plant seed tissue.

In a second aspect, this invention relates to the presence of such constructs in host cells, especially plant host cells, and to a method for producing proteins having C14 acyl-ACP thioesterase activity in a host cell or progeny thereof via the expression of a construct in the cell. In a related aspect, this invention provides transgenic host cells which have an expressed protein having C14 acyl-ACP thioesterase activity therein.

In a different embodiment, this invention relates to methods of using a DNA sequence encoding a protein having hydrolysis activity on C14:0 acyl-ACP substrates for the modification of the proportion of fatty acids produced within a cell, especially plant cells. Plant cells having such a modified fatty acid composition are also contemplated herein.

Of particular interest is the modification of the fatty acid composition of storage triglycerides in oilseed, plants for increased proportion of C14:0 fatty acyl groups. In this manner, seeds with modified oils having novel fatty acyl compositions are produced. Such novel seeds and oils are also encompassed by the instant invention.

DETAILED DESCRIPTION OF THE INVENTION

A protein capable of hydrolyzing C14 acyl-ACP substrates for use in the instant invention includes any sequence of amino acids, peptide, polypeptide or protein which demonstrates the ability to catalyze the production of free fatty acid(s) from C14:0-ACP substrates under plant enzyme reactive conditions. By "enzyme reactive conditions" is meant that any necessary conditions are available in an environment (i.e., such factors as temperature, pH, lack of inhibiting substances) which will permit the enzyme to function. Such proteins having C14 hydrolysis activity may be acyl-ACP thioesterases obtainable from plant sources, or may be from other sources, such as bacteria.

Of particular interest in the instant application are plant acyl-ACP thioesterases which have hydrolysis activity primarily on for C14:0-ACP substrates as compared to other acyl-ACP substrates, including medium- or long-chain acyl-ACP substrates. In this regard, thioesterase encoding sequences obtainable from *Cuphea palustris* are of particular interest in the instant invention. Other plant thioesterases having C14:0-ACP activity are also of interest, so long as the thioesterase demonstrates preferential activity on C14:0-ACP substrates, as compared to other medium-chain acyl-ACP substrates, i.e. those having carbon chain lengths of C8, C10 or C12. Thus, acyl-ACP thioesterases from nutmeg and camphor, which have substantial activity on C14:0-ACP substrates, as well as some activity on longer and other medium-chain substrates, are also encompassed by the instant invention. Also considered useful for production of C14 fatty acyl groups in plant seeds is a medium-chain acyl-ACP thioesterase from elm which demonstrates hydrolysis activity mainly on C10 and C16 substrates upon expression in *E. coli*, but results in increased levels of C14:0 fatty acids when expressed in *E. coli* and increased levels of C14:0 fatty acyl groups in triglycerides when expressed in transgenic plant seeds. Thus, it is recognized that plant acyl-ACP thioesterases useful for C14 production may also demonstrate hydrolysis activity on longer chain acyl-ACP substrates, such as those having carbon chain lengths of C16 or C18.

Also of interest in the instant application are proteins from non-plant sources which may be demonstrated to have acyl-ACP thioesterase activity on C14:0 acyl-ACPs, for example bacterial proteins having a primary enzymatic activity of an acyl-transferase, but which can be demonstrated to be capable of acyl-ACP hydrolysis activity on C14:0-ACP substrates. Of particular interest as sources of bacterial genes which encode proteins having C14 acyl-ACP activity are bioluminescent bacteria. As demonstrated herein for the bacterium *Vibrio harveyi*, the luxD genes in such bacteria provide a desired C14:0-ACP thioesterase activity.

In addition to the plant C14:0-ACP thioesterase sequences exemplified herein, acyl-ACP thioesteraes from other plant species are also of interest in the instant invention. Target plant species for isolation of genes encoding thioesterase having activity on C14:0-ACP substrates include those which have been reported to accumulate significant levels of C14 fatty acids, such as Myristicaceae, Simarubaceae, Vochysiaceae, and Salvadoraceae, and rainforest species of Erisma, Picramnia and Virola. For isolating C14:0-ACP thioesterase genes, nucleic acid probes may be prepared from C14:0-ACP thioesterase sequences provided herein, or from other plant medium-chain acyl-ACP thioesterase sequences which have been described.

Plant thioesterases, including medium-chain plant thioesterases are described in WO 91/16421 (PCT/US91/02960) and WO 92/20236 (PCT/US92/04332), which are hereby incorporated by reference in their entirety. Analysis of the encoding sequences and translated amino acid sequences of a number of plant acyl-ACP thioesterases has demonstrated the existence of two evolutionary classes of plant acyl-ACP thioesterases which are designated as "Class I" or "FatA" (for fatty acyl transferase type A) and "Class II" (or "FatB"). These classes are not a simple reflection of phylogenetic relationships of the various plants from which the thioesterase encoding sequences were obtained. For example, a *Cuphea hookeriana* FatA clone (clone CLT7 in FIG. 10 of WO 94/10288) is closely related to safflower FatA clones (sequences provided in FIG. 4 of WO 92/20236). In contrast, a *Cuphea hookeriana* FatB clone (CUPH-1 clone in FIG. 6 of WO 94/10288) is equally distant in evolutionary relationship from the *Cuphea hookeriana* FatA clone and the safflower FatA clone.

Class I thioesterases have been found in mango (FIG. 1), safflower, *Brassica campestris* and *Cuphea hookeriana*, which sequences are provided in U.S. Ser. No. 07/949,102, filed Sep. 21, 1992, now pending, and in WO 92/20236 and WO 94/10288. The plant Class I type thioesterases which have been described to date have preferential activity on longer chain acyl-ACP substrates, particularly 18:1-ACP. Class II thioesterases have been discovered in California bay, elm, *Cuphea hookeriana, Arabidopsis thaliana* and camphor. The plant C14:0 acyl-ACP thioesterases described herein are also of the Class II type. All medium-chain preferring acyl-ACP thioesterases described to date, including those having activity on C14:0, are of the Class II type. Thus, additional plant acyl-ACP thioesterases having activity on C14:0 substrates may be identified through sequence homology to medium-chain acyl-ACP thioesterases.

For example, a *C. palustris* C14 acyl-ACP thioesterase exemplified herein was obtained by screening a gene library with encoding sequences for medium-chain preferring acyl-ACP thioesterases from *Cuphea hookeriana*. Although the *C. hookeriana* gene sequences encode thioesterases having preferential activity on C8, C10 or C16 fatty acids, the substantial sequence homology within thioesterase genes in various Cuphea species allowed for detectable hybridization of the *C palustris* C14 clone to the *C hookeriana* gene probes. For hybridization of C14 thioesterases from plants other than Cuphea species, direct hybridization techniques may also be successful under low stringency conditions. For example, nutmeg C14:0-ACP thioesterase clones described herein were obtained by low stringency hybridization screening using a bay C12:0-ACP thioesterase gene fragment as probe. Thus, medium-chain acyl-ACP thioesterase genes from other plant species may be used to identify C14 acyl-ACP thioesterase genes. In addition, highly conserved regions have been identified in various plant medium-chain thioesterase amino acid sequences. Such regions find particular use in identification of additional medium-chain thioesterase genes, including those having preferential activity on C14:0-ACPs, for example by PCR amplification techniques.

As noted above, plants having significant presence of C14:0 fatty acids therein are preferred candidates to obtain naturally-derived C14:0 plant thioesterases. However, it should also be recognized that other plant sources which do not have a significant presence of C14:0 fatty acids may be screened as additional enzyme sources. For example, as discussed herein, a camphor acyl-ACP thioesterase gene was discovered to have preferential hydrolysis activity on C14:0-ACP substrates, with only minor activity on C12:0-ACP substrates, although analysis of camphor seed oil composition indicates significant levels of C12:0 fatty acyl groups and only low levels of C14 fatty acids. Thus, expression of medium-chain acyl-ACP thioesterases in *E. coli* may be used to identify acyl-ACP thioesterases which find use in production of C14:0 fatty acids in transgenic plant seed oils.

Northern analysis of candidate plant acyl-ACP thioesterase genes may also be useful to identify those having activity on C14:0 fatty acids. In *Cuphea hookeriana*, a clone, CUPH-1, which is expressed at low levels in various plant tissues has been demonstrated to have hydrolytic activity primarily on 16:0 acyl-ACP substrates. A related *C. hookeriana* thioesterase clone, CUPH-2, however, was demonstrated to be highly expressed and seed specific. This CUPH-2 clone was found to have hydrolytic activity primarily on medium-chain acyl-ACP substrates, namely C8 and C10. Similarly, *C. hookeriana* CUPH-4 is highly expressed in a seed specific manner, and as demonstrated further in the Examples herein, may be used to provide for increased production of C14 fatty acids in transformed host cells.

One skilled in the art will readily recognize that antibody preparations, nucleic acid probes (DNA and RNA) and the like may be prepared and used to screen and recover "homologous" or "related" thioesterases from a variety of plant sources. For immunological screening methods, antibody preparations either monoclonal or polyclonal are utilized. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technologies, Inc., 11:1–5).

For nucleic acid screening methods, genomic or cDNA libraries prepared from a candidate plant source of interest may be probed with conserved sequences from plant thioesterase to identify homologously related sequences. Homologous sequences are found when there is an identity of sequence, which may be determined upon comparison of sequence information, nucleic acid or amino acid, or through hybridization reactions between a known thioesterase and a candidate source. Conservative changes, such as Glu/Asp, Val/Ile, Ser/Thr, Arg/Lys and Gln/Asn may also be considered in determining amino acid sequence homology. Amino acid sequences are considered homologous by as little as 25% sequence identity between the two complete mature proteins. (See generally, Doolittle, R. F., *OF URFS and ORFS* (University Science Books, Calif., 1986.)

Typically, a lengthy nucleic acid sequence may show as little as 50–60% sequence identity, and more preferably at least about 70% sequence identity, between the target sequence and the given plant thioesterase of interest excluding any deletions which may be present, and still be considered related. When longer nucleic acid fragments (>100 bp) are employed as probes, such as large cDNA fragments, one may screen with low stringencies (for example 40°–50° C. below the melting temperature of the probe) in order to obtain signal from the target sample with 20–50% deviation, i.e., homologous sequences. (See, Beltz, et al. *Methods in Enzymology* (1983) 100:266–285.).

Shorter probes are also useful in thioesterase gene isolation techniques, and find particular applications in polymerase chain reactions (PCR). As described in more details in the following examples, medium-chain thioesterase gene fragments may be obtained by PCR using primers to sequences which are highly conserved in plant medium chain acyl-ACP thioesterase protein sequences.

Using methods known to those of ordinary skill in the art, a DNA sequence encoding a protein having hydrolytic activity on C14:0-ACP substrate can be inserted into constructs which may then be introduced into a host cell of choice for expression of the enzyme, including plant cells for the production of transgenic plants. Thus, potential host cells include both prokaryotic and eukaryotic cells. A host cell may be unicellular or found in a multicellar differentiated or undifferentiated organism depending upon the intended use. Cells of this invention may be distinguished by having a protein having hydrolysis activity on C14:0 acyl-ACP substrates foreign to the wild-type cell present therein, for example, by having a recombinant nucleic acid construct encoding a plant thioesterase therein.

Also, depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli, B. subtilis, Sacchromiyces cerevisiae*, including genes such as betagalactosidase, T7 polymerase, tryptophan E and the like.

For the most part, when expression in a plant host cell is desired, the constructs will involve regulatory regions (promoters and termination regions) functional in plants. The open reading frame, coding for the protein having hydrolytic activity on C14:0-ACP substrate will be joined at its 5' end to a transcription initiation regulatory region such as the wild-type sequence naturally found 5' upstream to a plant thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for CaMV 35S and nopaline and mannopine synthases, or with napin, ACP promoters and the like. The transcription/translation initiation regions corresponding to such structural genes are found immediately 5' upstream to the respective start codons. If a particular promoter is desired, such as a promoter native to the plant host of interest or a modified promoter, i.e., having transcription initiation regions derived from one gene source and translation initiation regions derived from a different gene source, including the sequence encoding the plant thioesterase of interest, or enhanced promoters, such as double 35S CaMV promoters, the sequences may be joined together using standard techniques. For most applications desiring the expression of C14:0-ACP thioesterases in plants, the use of seed specific promoters is preferred.

When expression of the proteins of the instant invention is desired in plant cells, various plants of interest include, but are not limited to, rapeseed (Canola varieties, including low linolenic lines, and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

In any event, the method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

The C14 fatty acids produced in the transgenic host cells of this invention are useful in various commercial applications, and will find particular use, for example, in the detergent industry.

The following examples are provided by way of illustration and not by way of limitation.

EXAMPLES

Example 1 Acyl-ACP Thioesterase Sequences
A. *Cuphea hookeriana*

DNA sequences corresponding to Cuphea thioesterase peptide regions are obtained by PCR using degenerate olgonucleotides designed from peptide fragments from conserved regions of plant thioesterases described in WO 92/20236. A forward primer, TECU9, contains 17 nucleotides corresponding to all possible coding sequences for amino acids 176–181 of the bay and camphor thioesterase proteins. A reverse primer, TECU3A, contains 18 nucleotides corresponding to the complement of all possible coding sequences for amino acids 283–288 of the bay and camphor thioesterase proteins, In addition, the forward and reverse primers contain BamHI or XhoI restriction sites, respectively, at the 5' end, and the reverse primer contains an inosine nucleotide at the 3' end. The safflower, bay and camphor sequences diverge at two amino acid positions in the forward primer region, and at one amino acid residue in the reverse primer region. The degeneracy of oligonucleotide primers is such that they could encode the safflower, bay and camphor sequences.

Polymerase chain reaction samples (100 µl) are prepared using reverse transcribed *Cuphea hookeriana* RNA as template and 1 µM of each of the oligonucleotide primers. PCR products are analyzed by agarose gel electrophoresis, and an approximately 300 bp DNA fragment, the predicted size from the thioesterase peptide sequences, is observed. The DNA fragment, designated C93A (Cuphea) is isolated and cloned into a convenient plasmid vector using the PCR-inserted BamHI and XhoI restriction digest sites. DNA sequence of representative clones is obtained. Analysis of these sequences indicates that at least two different, but homologous *Cuphea hookeriana* cDNAs were amplified.

Total Cuphea RNA for cDNA library construction may be isolated from developing *Cuphea hookeriana* embryos by modifying the DNA isolation method of Webb and Knapp (Plant *Mol. Biol. Reporter* (1990) 8:180–195). Buffers include:

REC: 50 mM TrisCl pH 9, 0.7M NaCl, 10 mM EDTA pH8, 0.5% CTAB.

REC+: Add B-mercaptoethanol to 1% immediately prior to use.

RECP: 50 mM TrisCl pH9, 10 mM EDTA pH8, and 0.5% CTAB.

RECP+: Add B-mercaptoethanol to 1% immediately prior to use.

For extraction of 1 g of tissue, 10 ml of REC+ and 0.5 g of PVPP is added to tissue that has been ground in liquid nitrogen and homogenized. The homogenized material is centrifuged for 10 min at 1200 rpm. The supernatant is poured through miracloth onto 3 ml cold chloroform and homogenized again. After centrifugation, 12,000 RPM for 10 min, the upper phase is taken and its volume determined. An equal volume of RECP+ is added and the mixture is allowed to stand for 20 min. at room temperature. The material is centrifuged for 20 min. at 10,000 rpm twice and the supernatant is discarded after each spin. The pellet is dissolved in 0.4 ml of 1M NaCl (DEPC) and extracted with an equal volume of phenol/chloroform. Following ethanol preciptation, the pellet is dissolved in 1 ml of DEPC water. Poly (A) RNA may be isolated from this total RNA according to Maniatis et al. (*Molecular Cloning: A Laboratory Manual* (1982) Cold Springs Harbor, N.Y.). cDNA libraries may be constructed in commercially available plasmid or phage vectors.

Thioesterase encoding fragments obtained by PCR as described above are labeled and used to screen Cuphea cDNA libraries to isolate thioesterase cDNAs. Preliminary DNA sequence of a Cuphea cDNA clone TAA 342 is presented in FIG. X. Translated amino acid sequence of the Cuphea clone from the presumed mature N-terminus (based on homology to the bay thioesterase) is shown.

The sequence is preliminary and does not reveal a single open reading frame in the 5' region of the clone. An open reading frame believed to represent the mature protein sequence is shown below the corresponding DNA sequence. The N-terminal amino acid was selected based on homology to the bay thioesterase protein.

Additional *Cuphea hookeriana* cDNA clones were obtained by screening a cDNA library prepared using a Uni-ZAP (Stratagene) phage library cloning system. The library was screening using radiolabeled TAA 342 DNA. The library was hybridized at 42° C. uing 30% formamide, and washing was conducted at low stringency (room temperature with 1× SSC, 0.1% SDS). Numerous thioesterase clones were identified and DNA sequences determined. Three classes of Cuphea cDNA clones have been identified. The original TAA 342 clone discussed above is representative of CUPH-1 type clones which have extensive regions of homology to other plant medium-chain preferring acyl-ACP thioesterases. Nucleic acid sequence and translated amino acid sequence of a CUPH-1 clone, CMT9, is shown in FIG. 6 of WO 94/10288. The mature protein is believed to begin either at or near the leucine at amino acid position 88, or the leucine at amino acid position 112. Northern analysis of RNA isolated from various *Cuphea hookeriana* plant tissues indicates that the CUPH-1 gene is expressed at a low level in all *Cuphea hookeriana* plant tissues examined.

A second class of Cuphea thioesterase cDNAs is identified as CUPH-2. These cDNAs also demonstrate extensive homology to other plant medium-chain acyl-ACP thioesterases. Expression of a representative clone, CMT7, in *E. coli* demonstrated that CUPH-2 clones encode a medium-chain preferring acyl-ACP thioesterase protein having preferential activity towards C8 and C10 acyl-ACP substrates. DNA sequence and translated amino acid sequence of CMT7 is shown in FIG. 7 of WO 94/10288.

Preliminary DNA sequence from the 5' end of an additional *Cuphea hookeriana* clone, CMT13, is shown in FIG. 6 herein. Although CMT13 demonstrates extensive sequence identity with CMT7, DNA sequence alignment reveals several gaps, which together total approximately 48 nucleotides, where the CMT13 clone is missing sequences present in the CMT7 clone. CMT13 is also referred to as a CUPH-4 clone.

Northern analysis of RNA isolated from various *Cuphea hookeriana* plant tissues indicates that CUPH-2 and CUPH-4 genes are highly expressed in developing seed tissues. Expression of the CUPH-2 and CUPH-4 clones in other *C. hookeriana* tissues, such as leaves, was not detected.

DNA sequence of an additional clone, CMT10, is shown in FIG. 9 of WO 94/10288. CMT10 has greater than 90% sequence identity with CMT9, but less than the approximately 99% sequence identity noted in fragments from other CUPH-1 type clones. CMT10 is also referred to as a CUPH-5 type clone.

B. *Cuphea palustris*

Total RNA is isolated from developing seeds of *C. palustris* as described above for *C. hookeriana*. A lambda ZipLox (BRL; Gaithersburg, Md.) cDNA library containing approximately $6\times10^6$ pfu is constructed from total RNA. Approximately 500,000 plaques from the unamplified library are screened using a mixed probe containing the thioesterase coding regions from *Cuphea hookeriana* CUPH-1 (CMT-9), CUPH-2 (CMT-7) and CUPH-5 (CMT-10). (DNA sequences of these clones are provided in WO 94/10288). Low stringency hybridization conditions are used: hybridization is conducted at room temperature in a solution of 30% formamide and 2× SSC (1× SSC=0.15M NaCl; 0.015M Na citrate). Eighty two putative positive clones were identified, thirty of which were plaque purified.

The nucleic acid sequence and translated amino acid sequence of clone designated as MCT34 is provided in FIG. 1. The translated amino acid sequence of this clone is approximately 80% identical to the sequence of a *Cuphea hookeriana* CUPH-4 clone (CMT-13 in FIG. 8 of WO 94/10288).

C. Bacterial luxD Gene Sequences

A *Vibrio harvei* luxD gene sequence is provided in Miyamoto et al. (*J. Biol. Chem.* (1988) 262:13393–13399). Additional luxD gene sequences have been reported by Baldwin et al. (*J. Biolumin. Chemilum.* (1989) 4:326–341) and Cochrum et al. (*Nucl. Acids Res.* (1990) 18:5570).

D. Nutmeg (*Myristica fragrans*)

Total RNA is isolated from developing nutmeg seeds as described above for Cuphea species. A lambda Zap (Stratagene; La Jolla, Calif.) cDNA library is constructed from total RNA. A BamHI/PstI fragment of pCGN3822 containing approximately 900 bp of a bay thioesterase C12 preferring acyl-ACP thioesterase encoding sequence (FIG. 1 of WO 94/10288) is radiolabeled and used as a probe of the nutmeg cDNA library under the following hybridization conditions: overnight hybridization at 30° C. in 50% formamide, 2×SSC, 5% dextran sulfate. The hybridized filters are washed at 30° C. in 0.1% SSC, 0.1%SDS and autoradiographed. Five putative positive clones were identified, three of which contain the sequence shown in FIG. 3, and are designated MYRF-2 or MfFatB1, and one of which contained the sequence shown in FIG. 2, and which is designated MYRF-1 or MfFatB2. Sequence of the other putative positive clone indicated that it did not encode an acyl-ACP thioesterase.

Sequence analysis of the MYRF-1 and MYRF-2 clones indicates that MYRF-1 is substantially a truncated version of MYRF-2, the initial proline residue of MYRF-1 corresponds to amino acid 97 of the MYRF-2 sequence. Another major difference in these clones is seen at the 3' end of the thioesterase encoding regions. The MYRF-1 clone lacks the TAG stop codon at nucleotides 1624–1626 of the MYRF-2 sequence, and thus the translated amino acid sequence of MYRF-1 extends into the MYRF-2 3' untranslated region until the next available in frame stop codon is reached (TGA at nucleotides 1087–1089 of MYRF-1).

E. Camphor (*Cinnamomum camphora*)

DNA sequence and translated amino acid sequence of a Class II camphor thioesterase encoding region generated by PCR is provided in FIG. 5B of WO 92/20236. A DNA fragment containing the mature protein region of the camphor clone is obtained by PCR from reverse transcribed cDNA prepared using RNA from developing camphor embryos. Forward (sense) and reverse (antisense) PCR primers, #4164 and #4165, are prepared which contain sequences useful for cloning using the CLONEAMP™ system (GIBCO BRL; Gaithersburg, Md.). Oligonucleotide 4164 contains a 20 nucleotide region corresponding to the camphor thioesterase encoding sequence of nucleotides 119–138 of the sequence in FIG. 5B of WO 92/20236. Oligonucleotide 4165 contains a 20 nucleotide region complementary to the camphor thioesterase 3' untranslated sequence represented as nucleotides 1391–1410 of FIG. 5B in WO 92/20236. The sequences of 4164 and 4165 are as follows:

4164 (SEQ ID NO: 8)
5' CUACUACUACUAUCGATACCATCTTTTCGGCTGCTGA 3'

4165 (SEQ ID NO: 9)
5' CAUCAUCAUCAUGAGCTCGCAAGAGAAAGAGCTTACAG 3'.

DNA sequence and translated amino acid sequence of a camphor PCR fragment obtained by PCR with 4164 and 4165 are provided in FIG. 4. The sequence begins at the XbaI site located at the beginning of the mature protein encoding region of the camphor thioesterase.

F. Elm

Elm acyl-ACP thioesterase clones may also be obtained using PCR primers for plant thioesterase sequences as discussed above for Cuphea. TECU9 and TECU3A are used in PCR reactions using reverse transcribed RNA isolated from elm embryos as template. As with Cuphea, an approximately 300 nucleotide fragment, E93A, is obtained and used to probe an elm cDNA library. Nucleic acid sequence and translated amino acid sequence of an elm medium-chain preferring acyl-ACP thioesterase clone, ULM-1, are shown in FIG. 5. The clone encodes the entire mature elm thioesterase protein, but appears to be lacking some of the transit peptide encoding region. By comparison with other plant medium-chain acyl-ACP thioesterases, the mature elm protein is believed to begin either at the leucine indicated as amino acid number 54, or at the asparatate indicated as amino acid number 79.

Example 2

Expression of C14:0 Acyl-ACP Thioesterases in *E. coli*

A. *Cuphea palustris*

Constructs for expression of a *Cuphea palustris* acyl-ACP thioesterase encoding sequence in *E. coli* are prepared. cDNA clone MCT34 is used as template for a polymerase chain reaction (PCR) to insert a StuI site 5' to the presumed mature protein start site located at amino acid 108 of the sequence shown in FIG. 1. A forward primer for PCR, MCT34 F1, contains DNA sequence corresponding to nucleotides 437–454 of the *C. palustris* sequence shown in FIG. 1, as well as sequences for insertion of SphI and StuI restriction digestion sites. An M13 sequencing primer referred to as "M13 Forward" is used for priming the reverse, or antisense, reaction. Sequence of the PCR primers are as follows:

MCT34F1 (SEQ ID NO: 10)  5' CUACUACUACUAGAATTCGCATGCAGGCCTATGCTTGACCGGAAATCT 3'

M13 Forward (SEQ ID NO: 11)  5' GTTTTCCCAGTCACGAC 3'.

The resulting PCR product is cloned as a StuI/XbaI fragment into pUC118, resulting in clone MCT34LZ, which provides for expression of the *C. palustris* thioesterase in *E. coli* as a lacZ fusion protein.

An additional construct for expression of the *C. palustris* thioesterase cDNA clone MCT34 in *E. coli* is prepared using a Qiagen (Chatsworth, Calif.) pQE vector which provides for high level expression and protein purification capability through a histidine tag. The DNA product resulting from PCR using the MCT34F1 and M13 Forward primers described above, is digested with SphI and SnaBI and cloned into SphI and SmaI digested pQE30 (Qiagen), resulting in MCT34HT.

MCT34LZ is transformed into *E. coli* fadD, an *E. coli* mutant which lacks medium-chain specific acyl-CoA synthetase (Overath et al., *Eur. J. Biochem* (1969) 7:559–574) for analysis of lipid composition. Cells containing the thioesterase construct, and a similar culture of control cells are grown at 30° C. to an $OD_{600}$ of ~0.5. Induction of the thioesterase expression may be achieved by the addition of IPTG to 0.2 to 0.4 mM followed by further growth for 30 to 120 minutes. For slow growing cultures, longer growth periods may be required following addition of IPTG. A 4.5 ml sample of the *E. coli* cells is transferred into a 15 ml glass vial with a teflon-lined cap. 100 μl of a 1 mg/ml standards solution containing 1 mg/ml each of C11:0 free fatty acid, C15:0 free fatty acid, and C17:0 TAG in 1:1 chloroform/methanol is added to the sample, followed by addition of 200 μl of glacial acetic acid and 10 ml of 1:1 chloroform/methanol. The samples are vortexed to mix thoroughly and centrifuged for 5 minutes at 1000 rpm for complete phase separation. The lower (chloroform) phase is carefully removed and transferred to a clean flask appropriate for use in a rotary evaporator (Rotovap). The sample is evaporated to near dryness. As medium-chain fatty acids appear to evaporate preferrentially after solvent is removed, it is important to use just enough heat to maintain the vials at room temperature and not completely remove the chloroform. The liquid residue is measured and transferred to a 2 ml glass vial with a Teflon cap. The vial used in the rotary evaporator is washed with chloroform/methanol, and the chloroform/methanol sample is pooled with the liquid residue (total volume of 600 μl).

For analysis of total fatty acids, a 100 μl aliquot of the sample is methanolyzed by adding 1 ml of 5% sulfuric acid in methanol, transferring the samples to a 5 ml vial, and incubating the sample in a 90° C. water bath for 2 hours. The sample is allowed to cool, after which 1 ml of 0.9% NaCl and 300 μl of hexane are added. The sample is vortexed to mix thoroughly and centrifuged at 1000 rpm for 5 minutes. The top (hexane) layer is carefully removed and placed in a plastic autosampler vial with a glass cone insert, followed by capping of the vial with a crimp seal.

For analysis of free fatty acids, the following TLC procedure for separation of free fatty acids from phospholipids (Cho and Cronan (1994) *J. Bacterial.* 1793–1795) is applied prior to methanolysis as described above. A 100 μl aliquot of the rotary evaporator residue and wash solution described above is applied to two lanes (50 μl/lane) of a silica-G TLC plate. The plates are developed in petroleum ether/ether/acetic acid (70/30/2, v/v) for approximately 15–20 minutes. The phospholipids remain at the origin, while the neutral lipids migrate close to the solvent front. Lipids are stained with iodine very briefly, marked and the silica from the marked areas transfered to Teflon-capped 2 ml tubes. The respective areas from the two lanes are pooled, and the samples are methanolyzed as described above.

Samples are analyzed by gas-liquid chromatography (GC) using a temperature program to enhance the separation of components having 10 or fewer carbons. The temperature program used provides for a temperature of 140° C. for 3 minutes, followed by a temperature increase of 5° C./minute until 230° C. is reached, and 230° C. is maintained for 11 minutes. Samples are analyzed on a Hewlett-Packard 5890 (Palo Alto, Calif.) gas chromatograph. Fatty acid content calculations are based on the internal standards. Results are presented in Table 1 below.

TABLE 1

| Strain | Free Fatty Acids (nmol/ml) in *E. coli* (fadD) | | | | | |
|---|---|---|---|---|---|---|
|  | 12:0 | 14:0 | 14:1 | 16:0 | 16:1 | 18:1 |
| Control | 1.87 | 0.54 | 0.0 | 1.70 | 0.0 | 0.0 |
| MCT34LZ | 2.41 | 8.83 | 19 | 2.96 | 0.0 | 0.0 |

The above results demonstrate a substantial increase in the production of 14:0 and 14:1 fatty acids in cells transformed with the *C. palustris* MCT34LZ clone.

B. *C. hookeriana* CUPH-4

A construct for expression of *C. hookeriana* CUPH-4 thioesterase in *E. coli* as a lacZ fusion is also prepared using PCR and cloning techniques such as described above for preparation of *C. palustris* constructs.

C. Nutmeg

Constructs for expression of two nutmeg (*Myristica fragrans*) Class II type thioesterases, MYRF-1 (MfFatB2) and MYRF-2 (MfFatB1), in *E. coli* as lacZ fusion proteins are prepared. MfFatB1 and MfFatB2 are digested with SalI and XhoI to excise the clone fragments containing the thioesterase encoding sequence from amino acid 131 of the MfFatB1 sequence (FIG. 3), or amino acid 35 of the MfFatB2 sequence (FIG. 2), through the 3' ends of the cDNA clones. The excised thioesterase encoding fragments are inserted into SalI digested pUC8 resulting in pCGN3856 (MfFatB1) and pCGN3855 (MfFatB2). These constructs encode lacZ fusions of the approximate mature thioesterase protein sequence (amino acid 130 of the MfFatB1 preprotein was selected as the mature protein N-terminus by homology to bay thioesterase protein).

The fusion proteins are expressed in fad+ and fadD strains of *E. coli* K12. Analysis of total fatty acids in liquid cultures of MYRF-1 and MYRF-2 transformed K27 (fadD) after overnight growth at 30° C. are provided in Table 2 below.

D. Camphor

The camphor PCR fragment described above is cloned into a pAMP vector resulting in pCGN5219. pCGN5219 is digested with XbaI and SalI and the resulting camphor thioesterase fragemnt is cloned into XbaI and SalI digested pBCSK+ (Stratagene), resulting in pCGN5220. pCGN5220 is used to transform *E. coli* fadD for analysis of lipid composition as described above. Results of these analyses are provided in Table 2 below.

TABLE 2

Total Fatty Acids (nmol/ml) in *E. coli* (fadD)

| Strain   | 12:0 | 14:0 | 14:1 | 16:0 | 16:1 | 18:1 |
|----------|------|------|------|------|------|------|
| Control  | 3    | 19   | 2    | 141  | 59   | 42   |
| MYRF-1   | 19   | 277  | 19   | 121  | 299  | 54   |
| MYRF-2   | 32   | 240  | 31   | 47   | 296  | 17   |
| CINC-1   | 99   | 195  | 204  | 43   | 102  | 26   |
| CUPH-4   | 3    | 217  | 0    | 277  | 107  | 112  |

In comparison to the control, 14:0 and 16:1 fatty acids are drastically elevated for the nutmeg, camphor and *C. hookeriana* clones. Increases in 12:0 and 14:1 are also observed with the nutmeg and camphor clones, and increases in 16:0 and 18:1 are also seen with the *C. hookeriana* CUPH-4 clone.

E. Elm

An elm acyl-ACP thioesterase cDNA clone is expressed in *E. coli* as a lacZ fusion. The ULM1 cDNA clone, KA10, represented in FIG. 5 is digested with StuI and XbaI to produce an approximately 1000 base pair fragment containing the majority of the mature elm thioesterase encoding sequence. The StuI site is located at nucleotides 250–255 of the sequence shown in FIG. 5, and the XbaI site is located at nucleotides 1251–1256, 3' to the stop codon. As discussed above, the N-terminus for the mature elm thioesterase is believed to be either the leucine residue encoded by nucleotides 160–162 or the aspartate residue encoded by nucleotides 235–237. The StuI/XbaI fragment is inserted into StuI/XbaI digested pUC118 resulting in construct KA11. For expression analysis, KA11 is used to transform *E. coli* strain DH5å or fadD.

As has been observed with bay thioesterase expression constructs WO 92/20236), *E. coli* clones expressing elm thioesterase exhibited abnormal growth rate and morphology phenotypes. The growth rate of *E. coli* DH5å (fadD$_+$) or fadD mutant cells expressing the elm thioesterase is initially much slower than growth of control cells at either 25° C. or 30° C. At 37° C., the elm thioesterase plasmid appears to be toxic to the *E. coli* cells. After growing the transformed cultures for several generations, variants may be selected which grow at the same rate as control cells at 25° C. or 30° C. A similar result was seen with fadD cells comprising bay thioesterase expression constructs. A fadD mutant strain selected as having a normal growth rate when expressing the bay thioesterase was cured of the bay thioesterase construct and transformed with the elm thioesterase construct. This strain exhibits a normal growth phenotype in the first generation of cells comprising the elm thioesterase construct.

The activity assays from normal growth phenotype KA11 cells reproducibly demonstrate differentially elevated C10:0-ACP and C16:0-ACP hydrolysis activities. Upon induction with IPTG, the C10:0-ACP and C16:-ACP activities are affected differently. The specific activity of the C16:0-ACP hydrolysis decreases slightly, while that of the C10:0-ACP hydrolase increases by approximately 44%. This data suggests the possibility that C16:0-ACP hydrolysis activity is derived from the *E. coli* cells, rather than the elm thioesterase. However, lipid analysis of transgenic plant seeds expressing the elm thioesterase (Example 5) demonstrates increased production of C16:0 resulting from C16:0-ACP hydrolysis activity of the elm thioesterase.

Results of GC analysis of total fatty acids in overnight cultures transformed with elm thioesterase construct KA11 are provided in Table 3 below.

TABLE 3

Total Fatty Acids (nmol/ml) in *E. coli* (fadD)

| Strain  | 8:0 | 10:0 | 12:0 | 14:0 | 14:1 | 16:0 | 16:1 | 18:1 |
|---------|-----|------|------|------|------|------|------|------|
| Control | 5   | 7    | 3    | 21   | 2    | 127  | 44   | 27   |
| KA11    | 96  | 161  | 32   | 109  | 16   | 17   | 91   | 17   |

Substantial increases in C8, C10, C12 and C14 fatty acids were observed. Subsequence studies of free fatty acids in overnight cultures of KA11 demosntrate that the observed increases are due to the free fatty acid compositions. In addition, an increase in 16:0 free fatty acids in KA11 versus the control culture was also observed.

F. Assay for Thioesterase Activity

For thioesterase activity assays, *E. coli* cells containing the acyl-ACP thioesterase constructs, and a similar culture of control cells are grown at 30° C. to an OD$_{600}$ of ~0.5. Induction of thioesterase expression in lacZ fusion constructs may be achieved by the addition of IPTG to 0.4 mM followed by 1 or 2 hours further growth. For slow growing cultures, longer growth periods may be required following addition of IPTG.

A ten-ml aliquot of each culture (containing cells plus the culture medium) is assayed for specific activity towards various carbon chain length acyl-ACP substrates as follows. Cells are harvested by centrifugation, resuspended in 0.5 ml assay buffer and lysed by sonication. Cell debris may be removed by further centrifugation. The supernatant is then used in thioesterase activity assays as per Pollard et al., *Arch. Biochem & Biophys.* (1991) 281:306–312. Results of thioesterase activity assays on Cuphea, nutmeg, elm and camphor thioesterase clones using 8:0, 10:0, 12:0, 14:0, 16:0, 18:0 and 18:1 acyl-ACP substrates are provided in Table 4 below. Results are presented as relative activity of the thioesterase expressing cells compared to control cells.

TABLE 4

Relative Activity (TE/Control)

| Strain  | 8:0 | 10:0 | 12:0 | 14:0 | 16:0 | 18:0 | 18:1 |
|---------|-----|------|------|------|------|------|------|
| MCT34HT | 0.9 | 0.8  | 1.0  | 42.8 | 21.8 | 1.5  |      |
| MYRF-1  | 1.1 | 1.4  | 1.8  | 13.6 | 13.3 | 5.5  | 13.6 |
| MYRF-2  | 0.9 | 0.9  | 0.8  | 4.2  | 6.6  | 2.8  | 10.9 |
| CINC-1  |     | 1.3  | 1.9  | 8.9  | 2.0  | 1.1  | 1.1  |
| ULM-1   |     | 5.4  | 1.5  |      | 6.9  |      | 1.7  |

Substantial increases in the hydrolysis activity on 14:0 and 16:0 relative to the control cells are observed with *C. palustris* MCT34HT transformed cells. Cells transformed with the nutmeg MYRF-1 and MYRF-2 clones also demonstrate substantial increases in activity on 14:0 and 16:0 substrates, as well as less substantial increases with 18:0 and 18:1. Expression of the camphor CINC-1 clone results mainly in increased activity on 14:0, although a lesser increase in 16:0 hydrolysis activity is also observed.

G. Bacterial luxD Gene

A *Vibrio* harvei myristoyl ACP thioesterase (luxD) encoding sequence (Miyamoto et al., *J. Biol. Chem.* (1988) 262:13393–13399) lacking the initial ATG codon is prepared by PCR. The gene is expressed in *E. coli* as a lacZ fusion and *E. coli* extracts are assayed to confirm myristoyl ACP thioesterase activity. The C14 thioesterase construct is used to transform an *E. coli* fadD strain. The cells transformed in this manner deposit large quantities of crystals which are identified as potasssium myristate by mass spectrometry. Fatty acid analysis of the *E. coli* extracts reveals that greater than 50% (on a mole basis) of the fatty acids are C14:0, as compared to control *E. coli* fadD cells which contain approximately 11.5 mole percent C14:0.

Example 3

Constructs for Plant Transformation

A. Napin Expression Cassette

A napin expression cassette, pCGN1808, is described in copending U.S. patent application Ser. No. 07/742,834 which is incorporated herein by reference. pCGN1808 is modified to contain flanking restriction sites to allow movement of only the expression sequences and not the antibiotic resistance marker to binary vectors. Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HincII to give pCGN3217. Sequenced of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XbaI cloning sites are located between the 5' and 3' noncoding regions.

B. Oleosin Expression Cassette

A cassette for cloning of sequences for transcription under the regulation of 5' and 3' regions from an oleosin gene may be prepared. Sequence of a *Brassica napus* oleosin gene is provided by Lee and Huang (Plant Phys. (1991) 96:1395–1397). Primers to the published sequence are used in PCR reactions to obtain the 5' and 3' regulatory regions of an oleosin gene from *Brassica napus* cv. Westar. Two PCR reactions were performed, one to amplify approximately 950 nucleotides immediately upstream of the ATG start codon for the oleosin gene, and one to PCR amplify approximately 600 bp including and downstream of the TAA stop codon for the oleosin gene. The PCR products were cloned into plasmid vector pAMP1 (BRL) according to manufacturer's protocols to yield plasmids pCGN7629 which contains the oleosin 5' flanking region and pCGN7630 which contains the 3' flanking region. The PCR primers included convenient restriction sites for cloning the 5' and 3' flanking regions together into an expression cassette. A PstI fragment containing the 5' flanking region from pCGN7629 was cloned into PstI digested pCGN7630 to yield plasmid pCGN7634. The BssHII (New England BioLabs) fragment from pCGN7634, which contains the entire oleosin expression cassette was cloned into BssHII digested pBCSK+ (Stratagene) to provide the oleosin cassette in a plasmid, pCGN7636. Sequence of the oleosin cassette in pCGN7636 is provided in FIG. 7. The oleosin cassette is flanked by BssHII, KpnI and XbaI restriction sites, and contains SalI, BamHI and PstI sites for insertion of wax synthase, reductase, or other DNA sequences of interest between the 5' and 3' oleosin regions.

C. *C. palustris* Acyl-ACP Thioesterase Expression Constructs

Constructs for expression of *C. palustris* thioesterase cDNA clone MCT34 in plant seeds under the regulatory control of napin and oleosin regulatory regions are prepared as follows. The thioesterase encoding region from MCT34 is obtained by PCR amplification using oligonucleotides for insertion of a SalI site 5' to the ATG start codon, and an NsiI site immediately 3' to the MCT34 translation stop codon. The oligonucleotide primers for PCR contained the SalI site (CpMet-1 forward primer) and the NsiI site (CpStop-1 reverse primer). In addition, the primers contain "CAU" (forward primer) and "CUA" (reverse primer) repeat sequences for cloning using the CLONEAMP™ system. Sequence of the PCR primers is as follows:

CpMet-1 (SEQ ID NO: 12)  5' CAUCAUCAUCAUGTCGACAAACATGGTGGCTGCCGCAG 3'

CpStop-1 (SEQ ID NO: 13)  5' CUACUACUACUAATGCATTACTAAGATATAGAGTTTCCATTTG 3'.

The resulting PCR product is cloned into pAMP and the DNA sequence determined to verify the PCR products.

The *C. palustris* thioesterase pAMP clone (pCGN3860) is digested with SalI and NsiI and the thioesterase encoding fragment isolated and cloned into SalI/PstI digested pCGN3223 (napin expression cassette) or pCGN7636 (oleosin expression cassette), resulting in pCGN3861 and pCGN3862, respectively.

Binary vectors for plant transformation with the *C. palustris* expression constructs are prepared by digestion of pCGN3861 and pCGN3862 with Asp718 and insertion of the resulting fragments into Asp718 digested pCGN1578 (McBride et al. (1990) *Plant Mol. Biol.* 14:269–276), resulting in pCGN3863 and pCGN3864, respectively.

D. luxD Expression Construct

Constructs for expression of the *Vibrio harvei* myristoyl ACP thioesterase in plant cells which utilize napin promoter regions are prepared as follows. Two 100 base oligos are synthesized:

HARV-S (SEQ ID NO: 14):

5' CGG TCT AGA TAA CAA TCA ATG CAA GAC TAT GC

ACA CGT GTT GCG TGT GAA CAA TGG TCA GGA GCT

TCA CGT CTG GGA <u>AAC GCC CCC AAA AGA AAA CGT G</u> 3'

HARV-A (SEQ ID NO: 15):

5' ATA CTC GGC CAA TCC AGC GAA GTG GTC CAT TCT

TCT GGC GAA ACC AGA AGC AAT CAA AAT GGT GTT

GTT TTT AAA AGG <u>CAC GTT TTC TTT TGG GGG CGT T</u> 3'

The two oligos contain a region of complementary sequence for annealing (underlined region). A TAQ polymerase extension reaction utilizing the two oligos yields a 180 bp product. The oligos consisted essentially of luxD sequence with sequence changes introduced to remove the 3 potential poly(A) addition sites and to alter 5 bases to change the codon preference from bacteria to plants. All changes were conservative; i.e. the amino acid sequence was not altered.

The 180 bp TAQ polymerase extension product is blunted and cloned into Bluescript. The approximately 180 bp luxD fragment is then removed from Bluescript by digestion with XbaI and EaeI and cloned in frame with the EaeI/XbaI fragment from the Vibrio cDNA clone, containing the remainder of the luxD gene, by 3-way ligation into XbaI/XhoI digested Bluescript SK. The luxD gene is removed by digestion with XbaI and partial digestion with PstI and cloned in frame with the safflower thioesterase transit peptide encoding region into a napin expression casette. The napin 5'/safflower transit:myristoyl ACP thioesterase/napin 3' fragment is cloned into KpnI/BamHI digested pCGN1557 (McBride and Summerfelt, supra) resulting in pCGN3845, a binary expression vector for plant transformation.

E. Nutmeg Acyl-ACP Thioesterase Expression Construct

Constructs for expression of nutmeg thioesterase cDNA clone MfFatB1 (pCGN3856 or MYRF-2) in plant seeds under the regulatory control of napin and oleosin regulatory regions are prepared as follows. The thioesterase encoding region from MfFatB1 is obtained by PCR amplification using oligonucleotides for insertion of a BamHI site 5' to the ATG start codon, and an XhoI site 3' to the MfFatB1 translation stop codon. The oligonucleotide primers for PCR contained the BamHI site (forward or sense primer) and the XhoI site (reverse or antisense primer). In addition, the primers contain "CAU" (forward primer) and "CUA" (reverse primer) repeat sequences for cloning using the CLONEAMP™ system.

Sequence of the PCR primers is as follows:

Sense (SEQ ID NO: 16)
5' CAUCAUCAUCAUGGATCCCTCATCATGTTGCCACATCTGC 3'

Antisense (SEQ ID NO: 17)
5' CUACUACUACUACTCGAGTTACATTTTGGCTATGC 3'.

The resulting PCR product is cloned into pAMP and the DNA sequence determined to verify the PCR products.

The nutmeg thioesterase pAMP clone (TA431) is digested with XhoI and partially digested with BamHI. The thioesterase encoding fragment is isolated (1.3 kb band) and cloned into BglII/Xho digested pCGN3223 (napin expression cassette), resulting in pCGN3868. A binary vector for plant transformation with the nutmeg expression construct is prepared by digestion of pCGN3868 with Asp718, and insertion of the resulting napin 5'/nutmeg TE/napin 3' fragment (4.2 kb) into pCGN1578PASS at the Asp718 site.

[pCGN1578PASS is prepared from pCGN1578 (McBride et al., supra) by substitution of the pCGN1578 polylinker region with a polylinker region containing the following restriction sites: Asp718, Asc, Pac, Swa, Sse and HindIII.] The resulting construct, pCGN3854, is used for plant transformation for production of C14 fatty acids.

A construct for expression of the nutmeg thioesterase under the regulatory control of an oleosin promoter is prepared as follows. pCGN3868 (napin 5'/nutmeg TE/napin 3' expression construct described above) is digested with SalI and EcoRV, and the resulting fragment, containing the nutmeg thioesterase encoding region joined in the 5' to 3' orientation to the napin 3' regulatory region, is inserted into SalI and EcoRV digested pCGN7636 (oleosin expression cassette described above). The resulting construct, pCGN3858, contains an oleosin 5'/nutmeg TE/napin 3'/oleosin 3' construct. pCGN3858 is digested with Asp718 and partially digested with BamHI to produce an ~2.6 kb fragment containing the oleosin 5', nutmeg thioesterase encoding region, and ~320 nucleotides of the napin 3' regulatory region. The 2.6 kb fragment is cloned into Asp718/BamHI digested pCGN1578, resulting in pCGN3857, a binary vector for plant transformation and expression of the nutmeg thioesterase.

F. Camphor Acyl-ACP Thioesterase Expression Construct

A construct for expression of camphor thioesterase under the regulatory control of a napin promoter is described. A transit peptide encoding sequence for bay thioesterase is obtained by digestion of pCGN3826 (bay C12 preferring acyl-ACP thioesterase clone described in WO 92/20236) with XbaI and SalI generating a DNA fragment having a plasmid vector backbone and the bay transit peptide encoding sequence (XbaI site is at beginning of mature bay protein encoding region). pCGN5220 (Example 2D) is digested with XbaI and Sal' to obtain the camphor mature TE encoding region. The pCGN5220 and pCGN3826 SalI/XbaI fragments are ligated to produce pCGN5231. pCGN5231 is digested with BamHI and SalI, and the resulting bay transit::camphor mature encoding fragment is inserted into BglII/XhoI digested pCGN3223 (napin expression cassette), resulting in pCGN5232. pCGN5232 was digested with NotI and, with Klenow to produce blunt ends, and the resulting napin 5'/bay transit::camphor mature/napin 3' fragment is inserted into HindIII digested and Klenow-blunted pCGN1578. The resulting construct, pCGN5233, is a binary vector for plant transformation and expression of camphor thioesterase.

G. Elm Acyl-ACP Thioesterase Expression Construct

A construct for expression of an elm acyl-ACP thioesterase in plant seed cells using a napin expression cassette is prepared as follows. The elm ULM-1 medium-chain acyl-ACP thioesterase cDNA does not appear to encode the entire thioesterase transit peptide. Thus, the elm thioesterase coding region was fused to the transit peptide encoding region from the Cuphea CUPH-1 clone as follows. pCGN4800 (CUPH-1 in napin cassette) was digested with XbaI, blunted and digested with StuI to remove the mature protein coding portion of the CUPH-1 construct. The StuI site is located at nucleotides 496–501 of the CUPH-1 sequence shown in FIG. 5 of WO 94/10288. The XbaI site is located between the end of the Cuphea thioesterase cDNA sequence and the napin 3' regulatory region. The ULM-1 mature protein encoding region is inserted into the napin/Cuphea transit peptide backbone resulting from removal of the Cuphea mature protein endoding region as follows. The ULM-1 clone is digested with XbaI, blunted and digested with StuI to obtain the elm thioesterase mature protein encoding region. The StuI site is located at nucleotides 250–255 of the sequence shown in FIG. 2 of WO 94/10288, and the XbaI site is located at nucleotides 1251–1256, 3' to the stop codon. Ligation of the elm StuI/XbaI fragment into the napin/Cuphea transit peptide backbone results in pCGN4802, having the napin 5'/Cuphea transit:elm mature/napin 3' expression construct. pCGN4802 is transferred to pCGN1557 as a HindIII fragment resulting in pCGN4803, a binary construct for plant transformation.

Example 4

Plant Transformation

A. Brassica Transformation

Brassica species may be transformed as reported by Radke et al. (*Plant Cell Reports* (1992) 11:499–505; *Theor. Appl. Genet.* (1988) 75:685–694), or as described in detail below.

*Brassica napus* seeds are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 μg/l), nicotinic acid (50 μg/l), glycine (200 μ/l), and 0.6% Phytagar (Gibco) pH 5.8. Seeds are germinated in a Percival chamber at 22° C. in a 16 h photoperiod with cool fluorescent and red light of intensity approximately 65 μg Einsteins per square meter per second ($\mu Em^{-2}S^{-1}$).

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA 101 containing a binary plasmid are transferred to 5 ml MG/L broth and grown overnight at 30° C. Hypocotyl explants are immersed in 7–12 ml MG/L broth with bacteria diluted to 1×10⁸ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4.7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

B. Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

C. Peanut Transformation

DNA sequences of interest may be introduced as expression cassettes, comprising at least a promoter region, a gene of interest, and a termination region, into a plant genome via particle bombardment as described in European Patent Application 332 855 and in co-pending application U.S. Ser. No. 07/225,332, filed Jul. 27, 1988.

Briefly, tungsten or gold particles of a size ranging from 0.5 $\mu M$–3 $\mu M$ are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 $\mu M$ to 300 $\mu M$.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25°±2° C. and are subsequently transferred to continuous cool white fluorescent light (6.8 W/m²). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

Example 5

Analysis of Transgenic Plants

A. *V. harveyi* luxD Expression Construct

Transgenic plants comprising a construct for expression of the *V. harveyi* luxD gene under the regulatory control of a napin promoter (pCGN3845) are grown to seed and analyzed to determine the percentage of C14 fatty acids produced as the result of insertion of the bacterial acyl transferase gene. Analysis of pooled seed samples from 24 segregating transgenic (T1) *Brassica napus* plants indicates C14 fatty acid levels ranging from 0.12 to 1.13 mole %. Two plants, 3845-1 and 3845-18, contain greater than 1 mole % C14:0 fatty acids in their seed oils. Similar analysis of non-transgenic *B. napus* seeds reveals C14:0 levels of approximately 0.1 mole %. Analysis of single seeds from 3845-18 reveals individual seeds having greater than 2 mole % C14:0 in the oil. Western analysis is conducted to determine amounts of the C14:0 thioesterase present in transgenic plants. A comparison of protein amount to mole % C14:0 (myristate) produced indicates that myristate levels increase with increasing amounts of the thioesterase protein.

B. Nutmeg (MYRF-2) Expression Construct

Mature seeds were harvested from transgenic *Brassica napus* plants (a QL01 derived low linolenic variety) containing pCGN3854, a construct for expression of nutmeg thioesterase clone MYRF-2 under the regulatory control of a napin promoter, and analyzed to determine mole percent fatty acid composition. Results are presented in Table 5 below.

TABLE 5

| Plant | 8:0 | 10:0 | 12:0 | 14:0 | 16:0 | 16:1 | 18:0 | 18:1 | 18:2 | 18:3 |
|---|---|---|---|---|---|---|---|---|---|---|
| 3854-1 | 0.00 | 0.26 | 0.30 | 13.50 | 22.10 | 0.49 | 4.84 | 37.62 | 16.26 | 1.96 |
| 3854-2 | 0.00 | 0.42 | 0.26 | 14.91 | 29.05 | 0.52 | 6.87 | 25.76 | 17.73 | 1.70 |
| 3854-3 | 0.00 | 0.27 | 0.43 | 21.73 | 30.90 | 0.43 | 6.48 | 19.54 | 15.85 | 1.62 |
| 3854-4 | 0.00 | 0.33 | 0.28 | 15.24 | 26.89 | 0.51 | 6.28 | 29.61 | 16.33 | 1.84 |

C14 fatty acyl groups are present in all four transgenic plants analyzed, with levels of C14 ranging from 13.5 to 21.73 mole percent. Background levels of C14 in non-transformed control plants are approximately 0.1 mole percent. Single seeds from transformant 3854-3 are disected for half seed lipid analysis. Results from these analyses are presented in Table 6 below.

TABLE 6

| NO. | 8:0 | 10:0 | 12:0 | 14:0 | 16:0 | 16:1 | 18:0 | 18:1 | 18:2 | 18:3 |
|---|---|---|---|---|---|---|---|---|---|---|
| 1 | 0.00 | 2.31 | 0.40 | 19.11 | 29.78 | 0.36 | 6.63 | 22.69 | 14.08 | 1.46 |
| 2 | 0.00 | 1.84 | 0.37 | 20.26 | 30.45 | 0.44 | 5.76 | 19.30 | 17.49 | 1.51 |
| 3 | 0.00 | 1.53 | 0.37 | 16.87 | 29.24 | 0.49 | 8.11 | 25.66 | 13.06 | 1.44 |
| 4 | 0.00 | 2.39 | 0.44 | 20.82 | 29.96 | 0.58 | 6.02 | 18.47 | 16.78 | 1.68 |
| 5 | 0.00 | 2.91 | 0.43 | 19.66 | 30.16 | 0.62 | 6.71 | 23.12 | 12.43 | 1.48 |
| 6 | 0.00 | 2.01 | 0.40 | 18.52 | 29.50 | 0.36 | 6.99 | 23.49 | 14.01 | 1.67 |
| 7 | 0.00 | 4.02 | 0.51 | 23.04 | 29.94 | 0.25 | 5.30 | 17.16 | 16.13 | 1.75 |
| 8 | 0.00 | 3.13 | 0.38 | 18.03 | 27.87 | 0.58 | 6.09 | 25.51 | 14.31 | 1.51 |
| 9 | 0.00 | 3.00 | 0.44 | 21.23 | 29.19 | 0.63 | 5.68 | 17.58 | 18.34 | 1.85 |
| 12 | 0.00 | 2.52 | 0.34 | 17.80 | 28.93 | 0.38 | 6.73 | 23.62 | 15.11 | 1.53 |
| 13 | 0.00 | 2.56 | 0.45 | 21.48 | 30.59 | 0.49 | 6.02 | 18.43 | 16.02 | 1.48 |
| 14 | 0.00 | 2.19 | 0.39 | 18.40 | 30.48 | 0.47 | 7.44 | 23.39 | 12.68 | 1.42 |
| 15 | 0.00 | 1.88 | 0.28 | 15.17 | 28.81 | 0.44 | 7.73 | 28.03 | 12.94 | 1.35 |
| 16 | 0.00 | 2.10 | 0.38 | 19.83 | 30.34 | 0.43 | 6.23 | 20.33 | 15.95 | 1.33 |
| 17 | 0.00 | 2.44 | 0.42 | 18.73 | 28.89 | 0.60 | 7.21 | 22.26 | 14.83 | 1.68 |
| 18 | 0.00 | 2.77 | 0.45 | 20.32 | 29.55 | 0.47 | 6.55 | 21.93 | 13.93 | 1.46 |
| 19 | 0.00 | 3.37 | 0.40 | 17.72 | 27.95 | 0.48 | 6.38 | 24.22 | 14.01 | 2.01 |
| 20 | 0.00 | 2.40 | 0.36 | 19.72 | 29.92 | 0.50 | 6.72 | 19.79 | 16.10 | 1.52 |

Additional single seed fatty acid composition data from 3854-3 and 854-11 are presented in FIG. 8. These data indicate C14 levels of up to 23% are obtained by expression of nutmeg thioesterase.

C. Camphor Expression Construct

Mature seeds were harvested from transgenic *Brassica napus* plants containing pCGN5233, a construct for expression of camphor thioesterase clone CINC-1 under the regulatory control of a napin promoter, and analyzed to determine mole percent fatty acid composition. Results are presented in Table 7 below.

TABLE 7

| Plant | 8:0 | 10:0 | 12:0 | 14:0 | 16:0 | 16:1 | 18:0 | 18:1 | 18:2 | 18:3 |
|---|---|---|---|---|---|---|---|---|---|---|
| 5233-1 | 0.00 | 0.84 | 0.87 | 6.93 | 9.64 | 0.95 | 1.51 | 41.35 | 21.47 | 14.99 |
| 5233-2 | 0.00 | 0.85 | 0.38 | 3.83 | 8.41 | 0.70 | 1.43 | 46.33 | 21.71 | 14.98 |

TABLE 7-continued

| Plant | 8:0 | 10:0 | 12:0 | 14:0 | 16:0 | 16:1 | 18:0 | 18:1 | 18:2 | 18:3 |
|---|---|---|---|---|---|---|---|---|---|---|
| 5233-4 | 0.00 | 0.96 | 1.33 | 11.46 | 11.69 | 1.06 | 1.16 | 31.07 | 23.54 | 16.26 |
| 5233-5 | 0.00 | 0.69 | 0.93 | 8.77 | 10.38 | 0.90 | 1.48 | 42.22 | 19.88 | 13.41 |
| 5233-6 | 0.00 | 0.69 | 1.29 | 11.38 | 10.98 | 0.83 | 1.54 | 40.75 | 18.32 | 12.98 |
| 5233-7 | 0.00 | 0.70 | 0.36 | 4.44 | 8.57 | 0.73 | 1.22 | 45.26 | 21.29 | 16.06 |
| 5233-8 | 0.00 | 1.07 | 0.24 | 2.46 | 7.67 | 0.85 | 1.25 | 47.47 | 22.51 | 14.90 |
| 5233-9 | 0.00 | 0.94 | 0.58 | 5.37 | 9.06 | 0.68 | 1.42 | 46.70 | 20.26 | 13.95 |
| 5233-10 | 0.00 | 0.83 | 0.26 | 2.84 | 7.89 | 0.74 | 1.26 | 46.21 | 21.68 | 16.88 |
| 5233-11 | 0.00 | 1.06 | 0.19 | 1.78 | 7.43 | 0.69 | 1.16 | 49.30 | 21.79 | 15.07 |
| 5233-12 | 0.00 | 0.69 | 0.51 | 5.42 | 9.02 | 0.77 | 1.40 | 46.09 | 19.81 | 15.03 |
| 5233-13 | 0.00 | 0.65 | 0.04 | 0.11 | 5.49 | 0.46 | 1.25 | 51.21 | 22.32 | 16.82 |
| 5233-14 | 0.00 | 0.81 | 0.64 | 6.46 | 9.54 | 0.86 | 1.21 | 44.11 | 20.50 | 14.33 |
| 5233-15 | 0.00 | 0.88 | 0.24 | 2.79 | 8.16 | 0.72 | 1.40 | 47.47 | 21.50 | 15.35 |
| 5233-16 | 0.00 | 1.00 | 0.35 | 3.52 | 8.03 | 0.66 | 1.35 | 44.98 | 23.01 | 15.94 |
| 5233-17 | 0.00 | 0.86 | 0.78 | 7.89 | 10.63 | 1.01 | 1.37 | 42.11 | 20.58 | 13.17 |
| 5233-18 | 0.00 | 1.53 | 0.62 | 6.25 | 10.14 | 0.83 | 1.37 | 39.80 | 23.38 | 15.64 |
| 5233-19 | 0.00 | 1.29 | 0.27 | 2.43 | 8.46 | 1.19 | 1.72 | 45.19 | 23.78 | 13.60 |
| 5233-20 | 0.00 | 1.23 | 0.34 | 3.59 | 9.49 | 1.03 | 1.87 | 48.74 | 19.24 | 12.93 |
| 5233-21 | 0.00 | 0.82 | 0.23 | 1.97 | 7.27 | 0.77 | 1.26 | 49.20 | 22.11 | 14.91 |
| 5233-22 | 0.00 | 0.60 | 0.54 | 5.63 | 9.64 | 0.75 | 1.56 | 45.07 | 21.94 | 12.53 |
| 5233-24 | 0.00 | 0.77 | 0.54 | 6.08 | 9.67 | 0.84 | 1.27 | 42.47 | 21.15 | 15.74 |
| Control | 0.00 | 0.74 | 0.02 | 0.10 | 6.15 | 0.66 | 1.48 | 51.75 | 21.03 | 16.22 |

An increased percentage of C14 fatty acyl groups above control plant background levels is observed in all but one of the transgenic plants analyzed. The levels of C14 range from approximately 2.0 mole percent to 11.5 mole percent. Increases in 16:0, and to a lesser extent, 12:0, fatty acyl groups are also observed.

Single seed data from transformants 5233-5 and 5233-6 are presented in FIG. 9. These results demonstrate C14 levels of greater than 20% are obtained in seeds expressing a camphor FatB thioesterase.

D. Elm Expression Construct

Mature seeds were harvested from transgenic *Brassica napus* plants containing pCGN4803, a construct for expression of elm thioesterase clone ULM-1 under the regulatory control of a napin promoter, and analyzed to determine mole percent fatty acid composition. Results are presented in Table 8 below.

E. *C. palustris* Expression Construct

Analysis of pooled seeds from four 3863-transformants reveals C14 levels of approximately 25%. Data from analysis of fatty acid compositions of single seeds from transformants 3863-10, 3863-7, 3863-4, 3863-8, 3863-2, and 3863-5 are presented in FIG. 10. These data indicate C14 levels of greater than 40% are obtained by expression of *C. palustris* FatB2 thioesterase clone.

The above results demonstrate the ability to obtain DNA sequences which encode thioesterase activities, which sequences may be expressed in plant seed cells for manipulation of seed oil fatty acid composition. In this manner production of significant levels of C14 fatty acids C14 may be obtained. The novel seed oils so produced may find uses in industry as whole oils, or can be fractionated using methods known in the industry to provide sources of the C14 fatty acids incorporated into the oil.

TABLE 8

| Plant | 8:0 | 10:0 | 12:0 | 14:0 | 16:0 | 16:1 | 18:0 | 18:1 | 18:2 | 18:3 |
|---|---|---|---|---|---|---|---|---|---|---|
| 4803-8 | 0.00 | 1.60 | 0.43 | 5.13 | 24.31 | 0.97 | 3.89 | 34.00 | 19.33 | 7.75 |
| 4803-9 | 0.00 | 1.49 | 0.44 | 5.04 | 20.64 | 1.05 | 2.22 | 35.32 | 22.36 | 9.27 |
| 4803-10 | 0.00 | 3.05 | 1.19 | 10.87 | 28.97 | 0.58 | 2.52 | 25.91 | 15.19 | 9.92 |
| 4803-11 | 0.00 | 2.24 | 0.61 | 5.63 | 21.16 | 0.96 | 2.53 | 36.18 | 19.62 | 8.80 |
| 4803-12 | 0.00 | 4.06 | 1.53 | 13.44 | 32.24 | 0.67 | 3.01 | 20.80 | 14.85 | 7.21 |
| 4803-14 | 0.00 | 3.89 | 1.41 | 11.60 | 29.13 | 0.59 | 2.71 | 25.71 | 14.76 | 8.18 |
| 4803-15 | 0.00 | 2.92 | 0.85 | 7.82 | 26.29 | 0.90 | 2.98 | 27.69 | 19.99 | 8.00 |
| 4803-16 | 0.00 | 3.07 | 1.33 | 12.33 | 30.91 | 0.52 | 2.70 | 26.42 | 12.90 | 7.94 |
| 4803-17 | 0.00 | 1.63 | 0.42 | 5.51 | 24.62 | 0.77 | 2.31 | 36.23 | 16.50 | 9.79 |
| 4803-18 | 0.00 | 2.14 | 0.81 | 7.97 | 27.08 | 0.53 | 2.75 | 33.31 | 15.03 | 8.22 |
| 4803-19 | 0.00 | 2.76 | 0.63 | 4.99 | 18.58 | 0.92 | 2.61 | 39.61 | 15.55 | 11.83 |
| 4803-20 | 0.00 | 2.60 | 0.86 | 8.46 | 27.38 | 0.60 | 2.61 | 30.00 | 16.37 | 8.80 |
| 4803-21 | 0.00 | 1.27 | 0.40 | 4.95 | 20.51 | 0.55 | 2.10 | 39.72 | 16.98 | 11.38 |
| 4803-22 | 0.00 | 1.52 | 0.18 | 1.99 | 14.80 | 1.09 | 3.72 | 46.53 | 18.26 | 9.07 |
| 4803-23 | 0.00 | 2.65 | 0.45 | 3.65 | 18.78 | 0.88 | 3.17 | 41.45 | 17.37 | 8.99 |
| 4803-27 | 0.00 | 2.91 | 0.51 | 3.68 | 18.11 | 0.91 | 3.19 | 40.29 | 18.03 | 9.73 |

An increased percentage of C14 fatty acyl groups above control plant background levels is observed in all of the transgenic plants analyzed. The levels of C14 range from approximately 2.0 mole percent to 13 mole percent. Increases in 16:0, and to a lesser extent, 10:0 and 12:0, fatty acyl groups are also observed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

---

What is claimed is:

1. A method of producing C14 fatty acids in plant seed triglycerides, wherein said method comprises:

growing a plant having integrated into its genome a DNA construct, said construct comprising in the 5' to 3' direction of transcription, a promoter functional in a plant seed cell, a DNA sequence encoding a plant thioesterase protein which preferentially utilizes C14:0 acyl-ACP substrates as compared to other medium-chain acyl-ACP substrates or as compared to C16:0 acyl-ACP substrates, and a transcription termination region functional in a plant cell, wherein said DNA sequence is obtained from camphor or *Cuphea palustris*.

2. The method of claim 1 wherein said plant is an oilseed crop plant.

3. The method of claim 2 wherein said oilseed crop plant is a Brassica plant.

4. The method of claim 1, wherein said promoter is from a gene preferentially expressed in plant seed tissue.

5. The method of claim 1, wherein said plant seed triglycerides comprise at least 5 mole percent C14 fatty acyl groups.

6. The method of claim 1, wherein said plant seed triglycerides comprise at least 20 mole percent C14 fatty acyl groups.

7. The method of claim 1, wherein said plant seed triglycerides comprise at least 40 mole percent C14 fatty acyl groups.

8. A plant seed comprising a minimum of 40 mole percent myristate in total fatty acids, wherein said seed has been transformed to express a *Cuphea palustris* DNA sequence encoding a thioesterase protein which preferentially utilizes C14:0 acyl-ACP substrates as compared to other medium-chain acyl-ACP substrates or as compared to C16:0 acyl-ACP substrates, wherein said myristate is incorporated into at least one position of a triglyceride molecule and wherein wild-type seed of said plant contains less than 1.0 mole percent laurate in fatty acids.

9. Plant seed oil, wherein a minimum of 40 mole percent of the acyl groups of said oil are myristyl acyl groups, and wherein said oil is derived from a seed of claim 8.

10. A Brassica seed comprising a minimum of 40 mole percent myristate in total fatty acids, wherein said seed has been transformed to express a *Cuphea palustris* DNA sequence encoding a thioesterase protein.

11. Plant seed oil, wherein a minimum of 40 mole percent of the acyl groups of said oil are myristyl acyl groups, and wherein said oil is derived from a Brassica seed of claim 10.

12. A DNA construct comprising an encoding sequence for a plant acyl-ACP thioesterase which preferentially utilizes C14 acyl-ACP substrates as compared to other medium-chain acyl-ACP substrates or as compared to C16:0 acyl-ACP substrates, wherein said plant is *Cuphea palustris*.

13. A construct according to claim 12 wherein said thioesterase comprises the amino acid sequence shown in FIG. 1.

14. A construct according to claim 13 wherein said encoding sequence comprises the acyl-ACP thioesterase encoding sequence shown in FIG. 1.

* * * * *